(12) United States Patent
Hosogoe et al.

(10) Patent No.: US 12,023,001 B2
(45) Date of Patent: Jul. 2, 2024

(54) ENDOSCOPE CAP AND METHOD OF STERILIZING ENDOSCOPE CAP

(71) Applicant: HOYA CORPORATION, Tokyo (JP)

(72) Inventors: Yoshitsugu Hosogoe, Tokyo (JP); Keiichi Saito, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 30 days.

(21) Appl. No.: 17/696,501

(22) Filed: Mar. 16, 2022

(65) Prior Publication Data

US 2022/0202281 A1 Jun. 30, 2022

Related U.S. Application Data

(62) Division of application No. 16/334,341, filed as application No. PCT/JP2017/037178 on Oct. 13, 2017, now abandoned.

(30) Foreign Application Priority Data

Oct. 14, 2016 (JP) ................................ 2016-202919
Feb. 7, 2017 (JP) ................................ 2017-020735
Aug. 30, 2017 (JP) ................................ 2017-166126

(51) Int. Cl.
*A61B 1/00* (2006.01)
*A61B 1/018* (2006.01)
(Continued)

(52) U.S. Cl.
CPC ...... *A61B 1/00105* (2013.01); *A61B 1/00098* (2013.01); *A61B 1/00101* (2013.01);
(Continued)

(58) Field of Classification Search
CPC ............ A61B 1/00105; A61B 1/00098; A61B 1/00101; A61B 1/0014; A61B 1/018;
(Continued)

(56) References Cited

U.S. PATENT DOCUMENTS 3,084,793 A  4/1963 Pitman
5,562,600 A  10/1996 Matsuno
(Continued)

FOREIGN PATENT DOCUMENTS

CN  101061940 A  10/2007
CN  105455772 A  4/2016
(Continued)

OTHER PUBLICATIONS

English translation of "International Search Report" of PCT/JP2017/037178, dated Apr. 19, 2018.
(Continued)

*Primary Examiner* — Regina M Yoo
(74) *Attorney, Agent, or Firm* — Kilpatrick Townsend & Stockton LLP

(57) ABSTRACT

To provide an endoscope cap with a raising base or the like which is easily attached and detached to and from a distal end of an endoscope.
The endoscope cap includes: a cover that is attachable and detachable to and from a distal end of an insertion portion of an endoscope including a lever which is rotatably provided at the distal end of the insertion portion of the endoscope and a rotating portion which rotates the lever; and a raising base that has a lever connection portion connected to the lever and is rotatably provided inside the cover, and the endoscope cap is supplied in the state of being enclosed in an individual packaging member.

2 Claims, 40 Drawing Sheets

(51) Int. Cl.
*A61L 2/07* (2006.01)
*A61L 2/08* (2006.01)
*A61B 90/00* (2016.01)
*A61B 90/70* (2016.01)

(52) U.S. Cl.
CPC ............ *A61B 1/0014* (2013.01); *A61B 1/018* (2013.01); *A61L 2/07* (2013.01); *A61L 2/081* (2013.01); *A61L 2/087* (2013.01); *A61B 2090/0808* (2016.02); *A61B 2090/701* (2016.02); *A61L 2202/181* (2013.01); *A61L 2202/24* (2013.01)

(58) Field of Classification Search
CPC ...... A61B 2090/0808; A61B 2090/701; A61B 1/126; A61B 2090/0814; A61B 1/00137; A61L 2/07; A61L 2/081; A61L 2/087; A61L 2202/181; A61L 2202/24; G02B 23/24
See application file for complete search history.

(56) References Cited

U.S. PATENT DOCUMENTS

| | | | |
|---|---|---|---|
| 5,569,157 | A | 10/1996 | Nakazawa et al. |
| 5,707,344 | A | 1/1998 | Nakazawa et al. |
| 5,868,663 | A | 2/1999 | Katsurada et al. |
| 2001/0000227 | A1 | 4/2001 | Kowanko |
| 2003/0159966 | A1 | 8/2003 | Mcmichael et al. |
| 2003/0159967 | A1 | 8/2003 | Mcmichael et al. |
| 2003/0192799 | A1 | 10/2003 | Addy et al. |
| 2003/0205029 | A1 | 11/2003 | Chapolini et al. |
| 2007/0008160 | A1 | 1/2007 | Nagai et al. |
| 2007/0246506 | A1 | 10/2007 | Hamazaki et al. |
| 2007/0270638 | A1 | 11/2007 | Kitano et al. |
| 2011/0223079 | A1 | 9/2011 | Nagai et al. |
| 2016/0227988 | A1 | 8/2016 | Jiang et al. |
| 2016/0270635 | A1 | 9/2016 | Tanaka et al. |
| 2016/0270636 | A1 | 9/2016 | Iwasaka et al. |
| 2016/0270637 | A1 | 9/2016 | Tanaka et al. |
| 2017/0325666 | A1 | 11/2017 | Jiang et al. |
| 2018/0116491 | A1 | 5/2018 | Yamaya |

FOREIGN PATENT DOCUMENTS

| | | |
|---|---|---|
| CN | 105982635 A | 10/2016 |
| JP | H06-315458 | 11/1994 |
| JP | H07194513 A | 8/1995 |
| JP | 0856900 | 3/1996 |
| JP | H08-071032 | 3/1996 |
| JP | H08-126605 | 5/1996 |
| JP | H08-243071 | 9/1996 |
| JP | H08-243076 | 9/1996 |
| JP | H08-252211 | 10/1996 |
| JP | H09-253036 | 9/1997 |
| JP | H11-004804 | 1/1999 |
| JP | 2002-017655 | 1/2002 |
| JP | 2004-267596 | 9/2004 |
| JP | 2007-330756 | 12/2007 |
| JP | 2009-273665 | 11/2009 |
| JP | 2009-284939 | 12/2009 |
| JP | 2010273727 A | 12/2010 |
| JP | 2013-039358 | 2/2013 |
| JP | 2014132923 A | 7/2014 |
| JP | 2016-174821 | 10/2016 |
| JP | 2016-174822 | 10/2016 |
| WO | 2017002586 A1 | 1/2017 |

OTHER PUBLICATIONS

English translation of "International Search Report" of PCT/JP2017/037108, dated Sep. 22, 2018.
English translation of "International Search Report" of PCT/JP2017/037111, dated Apr. 19, 2018.
English translation of "International Search Report" of PCT/JP2017/037177, dated Apr. 19, 2018.
English translation of "International Search Report" of PCT/JP2017/037200, dated Apr. 19, 2018.
U.S. Appl. No. 16/334,341, "Advisory Action", Jul. 27, 2021, 5 pages.
U.S. Appl. No. 16/334,341, "Final Office Action", May 14, 2021, 11 pages.
U.S. Appl. No. 16/334,341, "Final Office Action", Jan. 27, 2022, 6 pages.
U.S. Appl. No. 16/334,341, "Non-Final Office Action", Oct. 5, 2020, 10 pages.
U.S. Appl. No. 16/334,341, "Non-Final Office Action", Oct. 1, 2021, 12 pages.
JP2017-191576, "Notice of Reasons for Refusal" with Machine Translation, Jul. 27, 2021, 10 pages.
JP2017-191576, "Notice of Reasons for Refusal" with Machine Translation, Mar. 1, 2022, 12 pages.
JP2017-191576, "Notice of Reasons for Refusal" with Machine Translation, Aug. 23, 2022, 14 pages.
PCT/ JP2017/037178, "English translation of International Search Report", Dec. 26, 2017.
PCT/JP2017/037108, "English translation of International Search Report", Dec. 26, 2017.
PCT/JP2017/037111, "English translation of International Search Report", Dec. 5, 2017.
PCT/JP2017/037177, "English translation of International Search Report", Dec. 26, 2017.
PCT/JP2017/037200, "English translation of International Search Report", Dec. 12, 2017.

FIG. 5
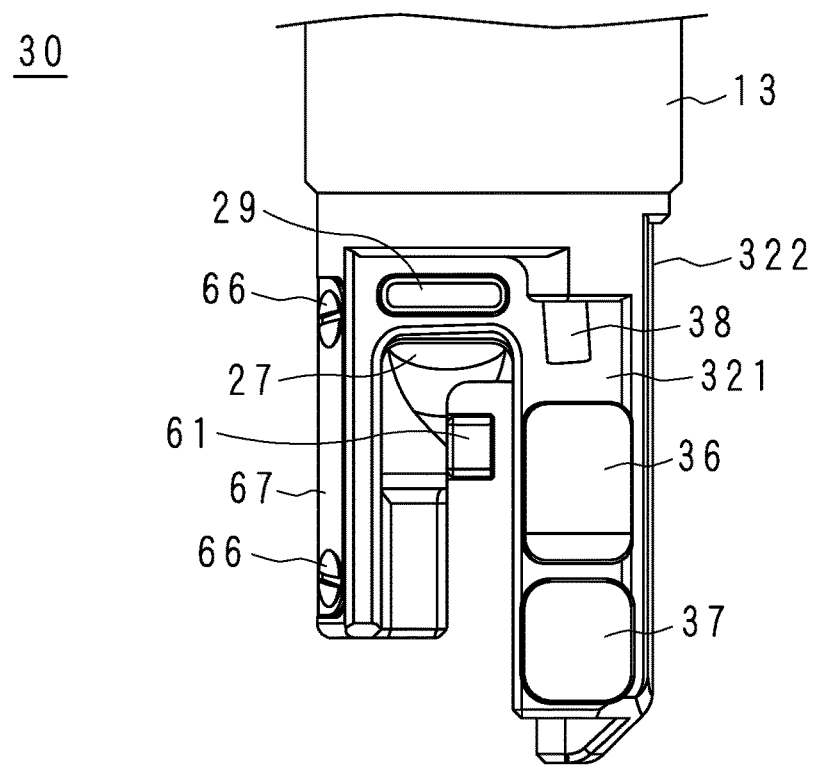
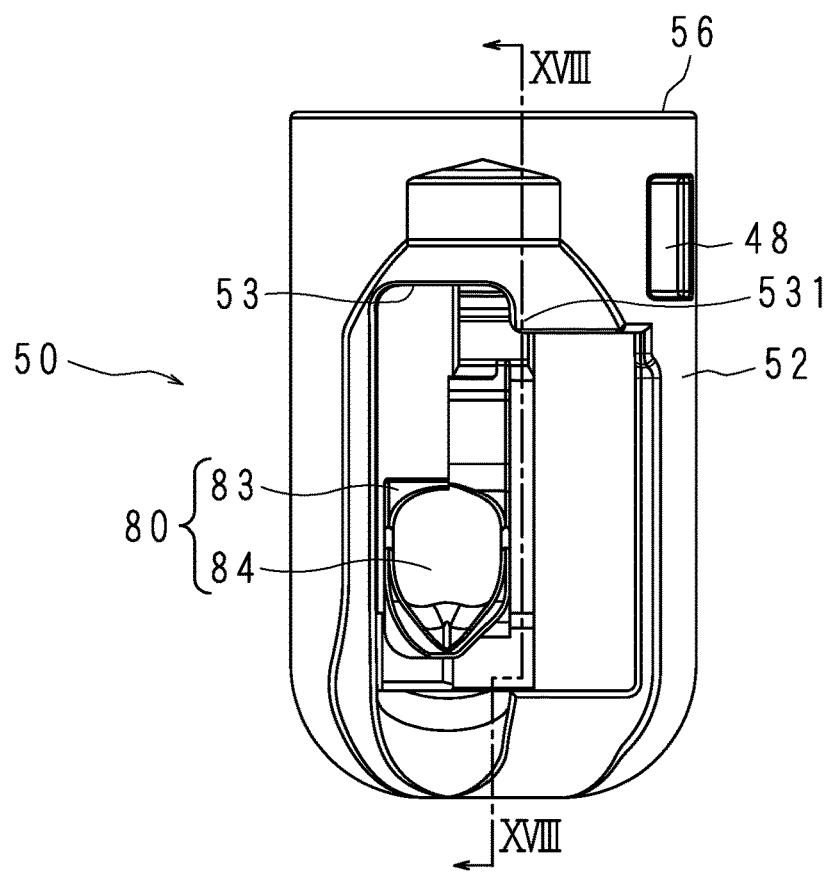

FIG. 6
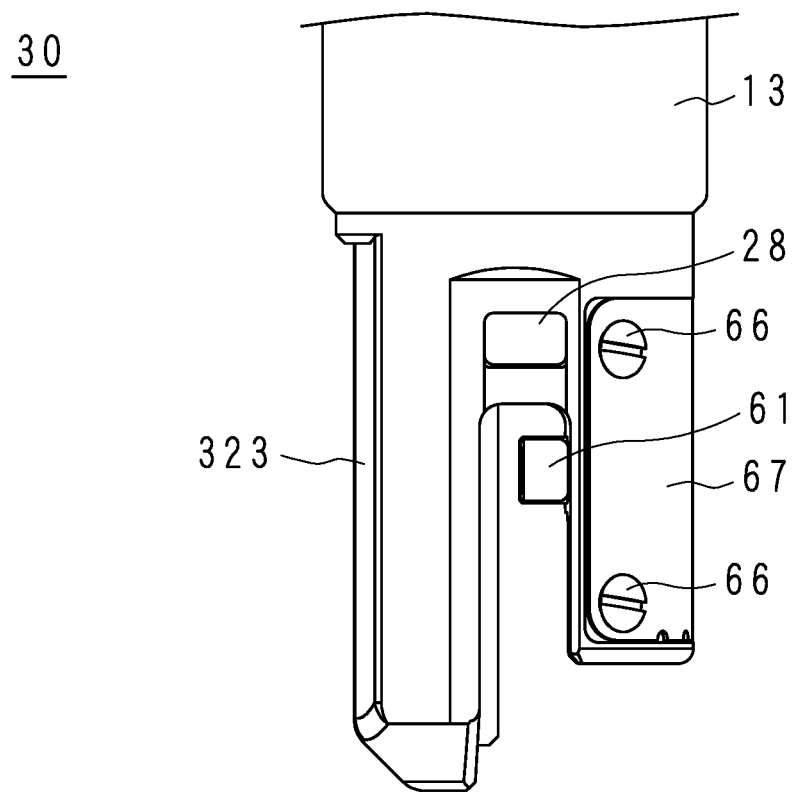
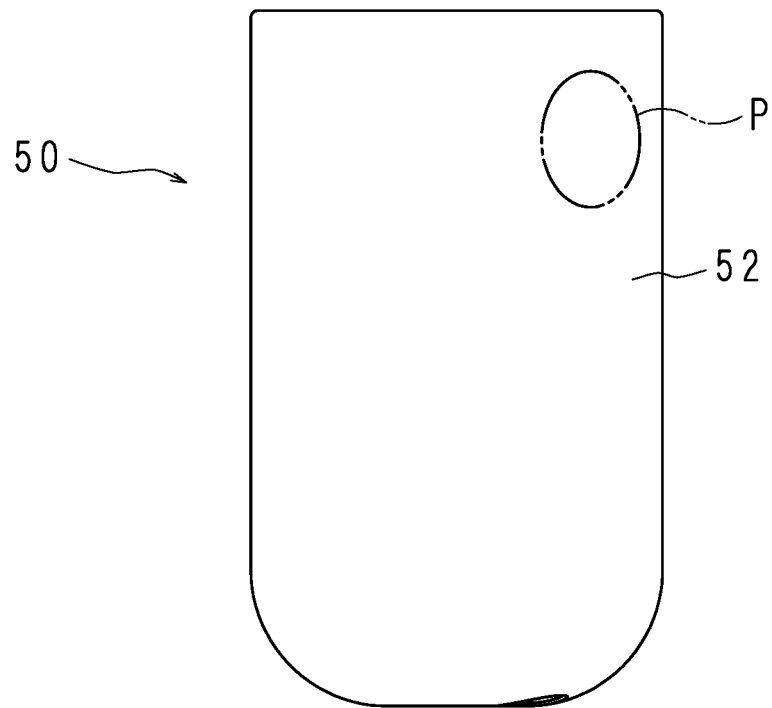

ENDOSCOPE CAP AND METHOD OF STERILIZING ENDOSCOPE CAP

CROSS-REFERENCE TO RELATED APPLICATIONS

This application is a division of U.S. application Ser. No. 16/334,341, filed Mar. 18, 2019, which is the National Stage of PCT International Application No. PCT/JP2017/037178, filed Oct. 13, 2017, which claims priority to Japanese Patent Application No. 2016-202919, filed Oct. 14, 2016, Japanese Patent Application No. 2017-020735, filed Feb. 7, 2017, and Japanese Patent Application No. 2017-166126, filed Aug. 30, 2017, and the contents of which are incorporated by reference.

FIELD

The technology herein relates to an endoscope cap and a method of sterilizing an endoscope cap.

BACKGROUND

An endoscope including a raising base at a distal end of a channel passing through the inside of an insertion portion has been used.

The raising base is used at the time of bending a treatment tool or the like that has passed through the channel and guiding the treatment tool in a desired direction.

An endoscope provided with a wall between a raising wire that moves a raising base and the raising base is disclosed (Japanese Patent Application Laid-Open Publication No. 8-56900).

In the endoscope disclosed in Japanese Patent Application Laid-Open Publication No. 8-56900, it takes time and effort for cleaning since a structure around the raising base is complicated.

In one aspect, an object of the present disclosure is to provide an endoscope cap with a raising base or the like, which is easily attached and detached to and from a distal end of an endoscope and facilitates cleaning of the endoscope by being detached.

An endoscope cap includes: a cover that is attachable and detachable to and from a distal end of an insertion portion of an endoscope including a lever which is rotatably provided at the distal end of the insertion portion of the endoscope and a rotating portion which rotates the lever; and a raising base that has a lever connection portion connected to the lever and is rotatably provided inside the cover, and is supplied in the state of being sealed in an individual packaging member.

In one aspect, it is possible to provide the endoscope cap with the raising base or the like, which is easily attached and detached to and from the distal end of the endoscope and facilitates the cleaning of the endoscope by being detached.

BRIEF DESCRIPTION OF DRAWINGS

FIG. 5 is a front view for describing a state where an endoscope cap is detached from the distal end of the insertion portion.

FIG. 6 is a back view illustrating the state where the endoscope cap is detached from the distal end of the insertion portion.

DETAILED DESCRIPTION OF NON-LIMITING EXAMPLE EMBODIMENTS

First Embodiment

Figure 1:
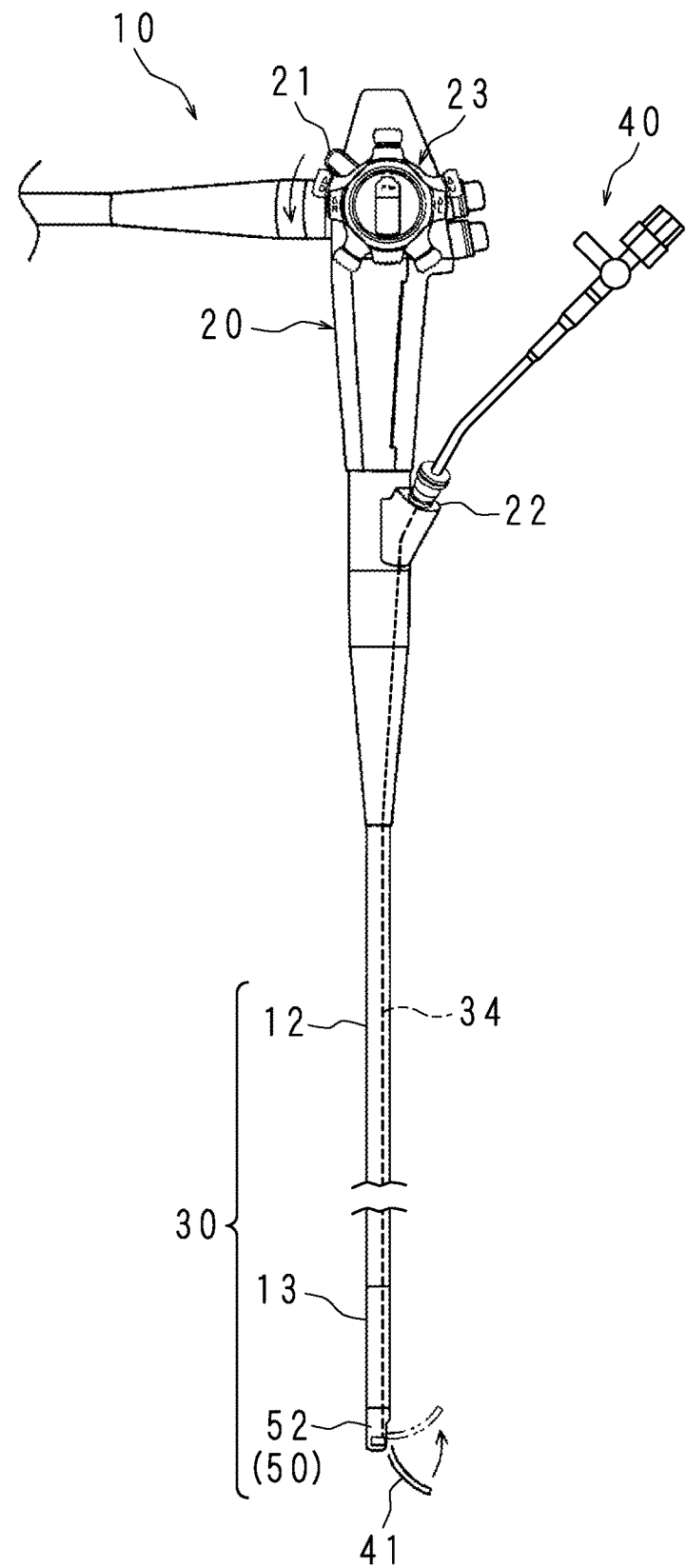
FIG. 1 is an exterior view of an endoscope.

FIG. 1 is an exterior view of an endoscope. An endoscope 10 of the present embodiment is a flexible scope for an upper gastrointestinal tract. The endoscope 10 has an operation unit 20 and an insertion portion 30. The operation unit 20 has a raising operation lever 21, a channel inlet 22, and a bending knob 23. The operation unit 20 is connected to a video processor (not illustrated), a light source device, a display device, and the like.

The insertion portion 30 is long and has one end connected to the operation unit 20. The insertion portion 30 includes a soft portion 12, a bending portion 13, and an endoscope cap 50 in this order from the operation unit 20 side. The soft portion 12 is soft. The bending portion 13 is bent according to an operation of the bending knob 23. The endoscope cap 50 covers a hard distal end portion 31 (see FIG. 2) continuous with the bending portion 13.

The endoscope cap 50 can be attached to and detached from the endoscope 10 according to the present embodiment through the distal end portion 31. The endoscope cap 50 has a cover 52 and a raising base 80 (see FIG. 2) which are exterior members. Detailed configurations of the endoscope cap 50 will be described later.

In the following description, a longitudinal direction of the insertion portion 30 is referred to as an insertion direction. Similarly, a side close to the operation unit 20 along the insertion direction is referred to as an operation unit side, and a side far from the operation unit 20 is referred to as a distal end side.

Figure 2:
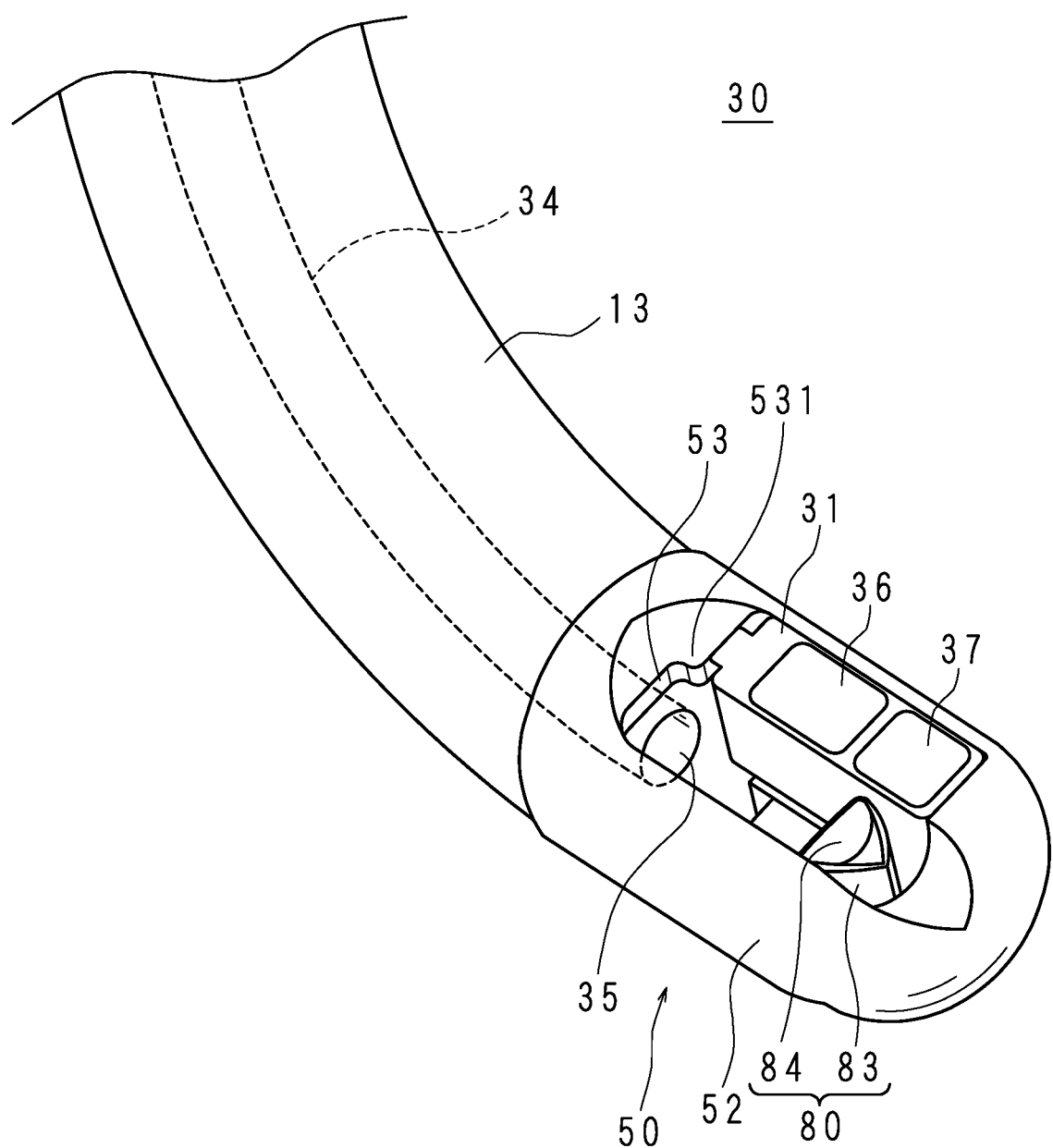
FIG. 2 is a perspective view of a distal end of an insertion portion.
Figure 3:
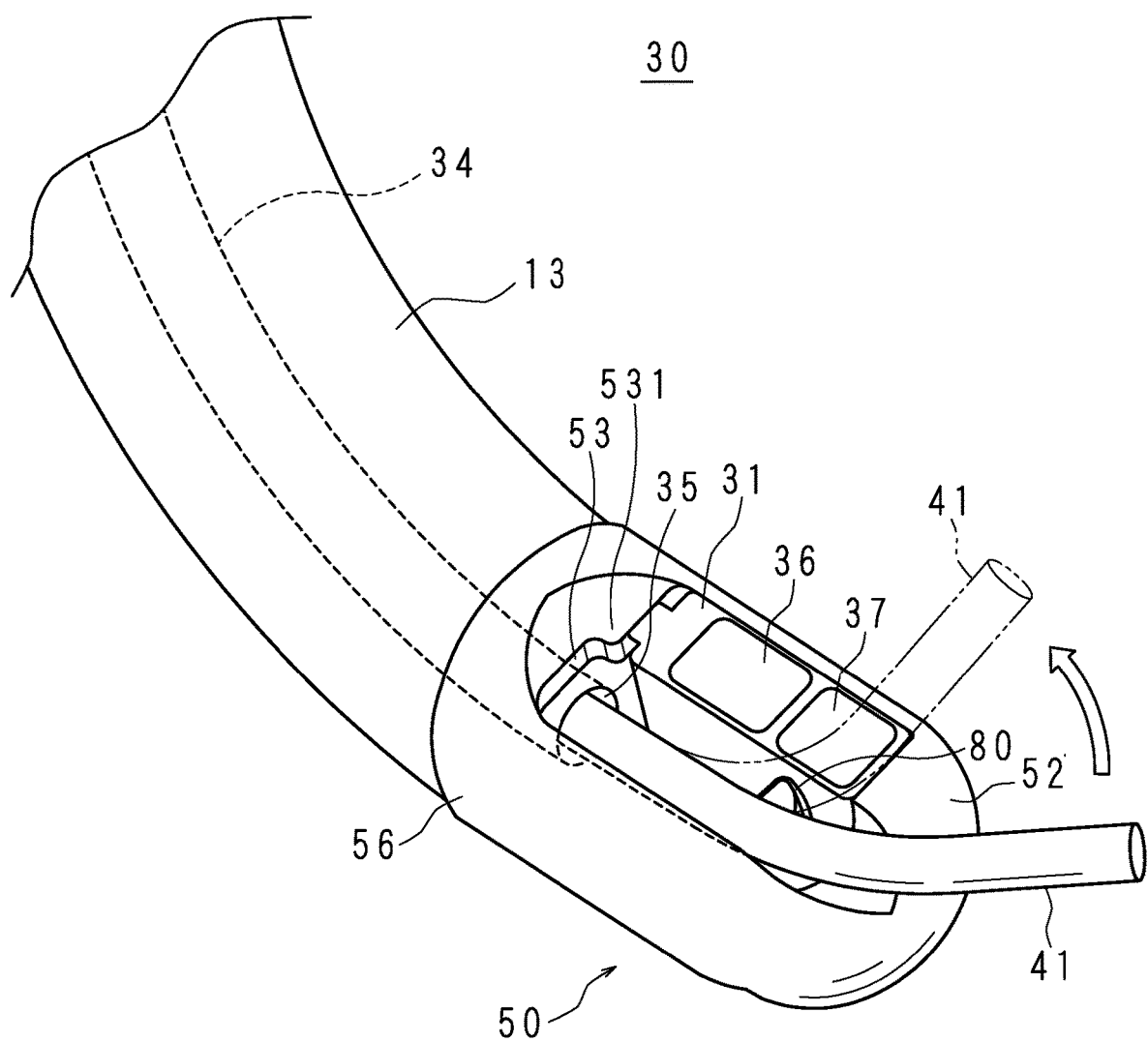
FIG. 3 is an explanatory view illustrating a state where a treatment tool distal end portion protrudes from the distal end of the insertion portion.

FIG. 2 is a perspective view of a distal end of the insertion portion 30. FIG. 3 is an explanatory view illustrating a state where a treatment tool distal end portion 41 protrudes from the distal end of the insertion portion 30. The configuration of the endoscope 10 according to the present embodiment will be described with reference to FIGS. 1 to 3.

The distal end portion 31 arranged at a distal end of the bending portion 13 has an observation window 36 and an illumination window 37 arrayed side by side on one side along the insertion direction. The illumination window 37 is arranged closer to the distal end side than the observation window 36. The distal end portion 31 has a channel outlet 35 on the operation unit side on the other side. A raising portion 83 is arranged on the distal end side of the channel outlet 35. The cover 52 covering the distal end portion 31 has a substantially rectangular window portion 53 in a portion corresponding to the observation window 36, the illumination window 37, and the raising portion 83. A side of the window portion 53 on the operation unit side is a one-step stair shape in which a side of the raising portion 83 is located on the operation unit side and a side of the observation window 36 is on the distal end side, and a stopper portion 531 is provided in the central part thereof.

The illumination window 37 performs irradiation with illumination light emitted from a light source device (not illustrated). It is possible to optically observe a range illuminated by the illumination light through the observation window 36. The endoscope 10 of the present embodiment is of a so-called side-view type in which a viewing direction in which optical observation is possible intersects the insertion direction. The endoscope 10 may be of a front oblique-view type in which the viewing direction is slightly inclined toward the distal end side or a rear oblique-view type in which the viewing direction is slightly inclined toward the operation unit side.

The channel inlet 22 and the channel outlet 35 are connected by a channel 34 passing through the inside of the soft portion 12 and the bending portion 13. As the treatment tool 40 is inserted from the channel inlet 22 from a side of the treatment tool distal end portion 41, the treatment tool distal end portion 41 can protrude from the channel outlet 35.

The treatment tool distal end portion 41 protrudes while loosely curving on the raising portion 83 as indicated by the solid line in FIG. 3. When the raising operation lever 21 is operated as indicated by the arrow in FIG. 1, a lever 60 (see FIG. 8) moves as will be described later, and the raising base 80 moves in conjunction with the lever 60. As the raising base 80 moves, the treatment tool distal end portion 41 on the raising base 80 is bent toward the operation unit 20 as indicated by the arrows and two-dot chain lines in FIGS. 1 and 3. The movement of the treatment tool distal end portion 41 is captured by an imaging device or the like (not illustrated) through the observation window 36, and is displayed on the display device (not illustrated).

The treatment tool 40 is a treatment tool such as a high-frequency knife, a forceps, and a contrast tube. Incidentally, the instrument to be inserted into the channel 34 is not limited to the instrument for treatment. For example, an instrument for observation such as an ultrasonic probe and a microscopic endoscope may be inserted into the channel 34 for use. In the following description, the instrument for observation is also referred to as the treatment tool 40.

In the following description, the movement of the raising base 80 as described above may be expressed as "the raising base 80 rises". In the following description, an operation in which the treatment tool distal end portion 41 is pushed by the raised raising base 80 and is bent is sometimes referred to as "the treatment tool 40 rises". It is possible to adjust the degree of the rise of the treatment tool 40 by the operation of the raising operation lever 21.

Figure 4:
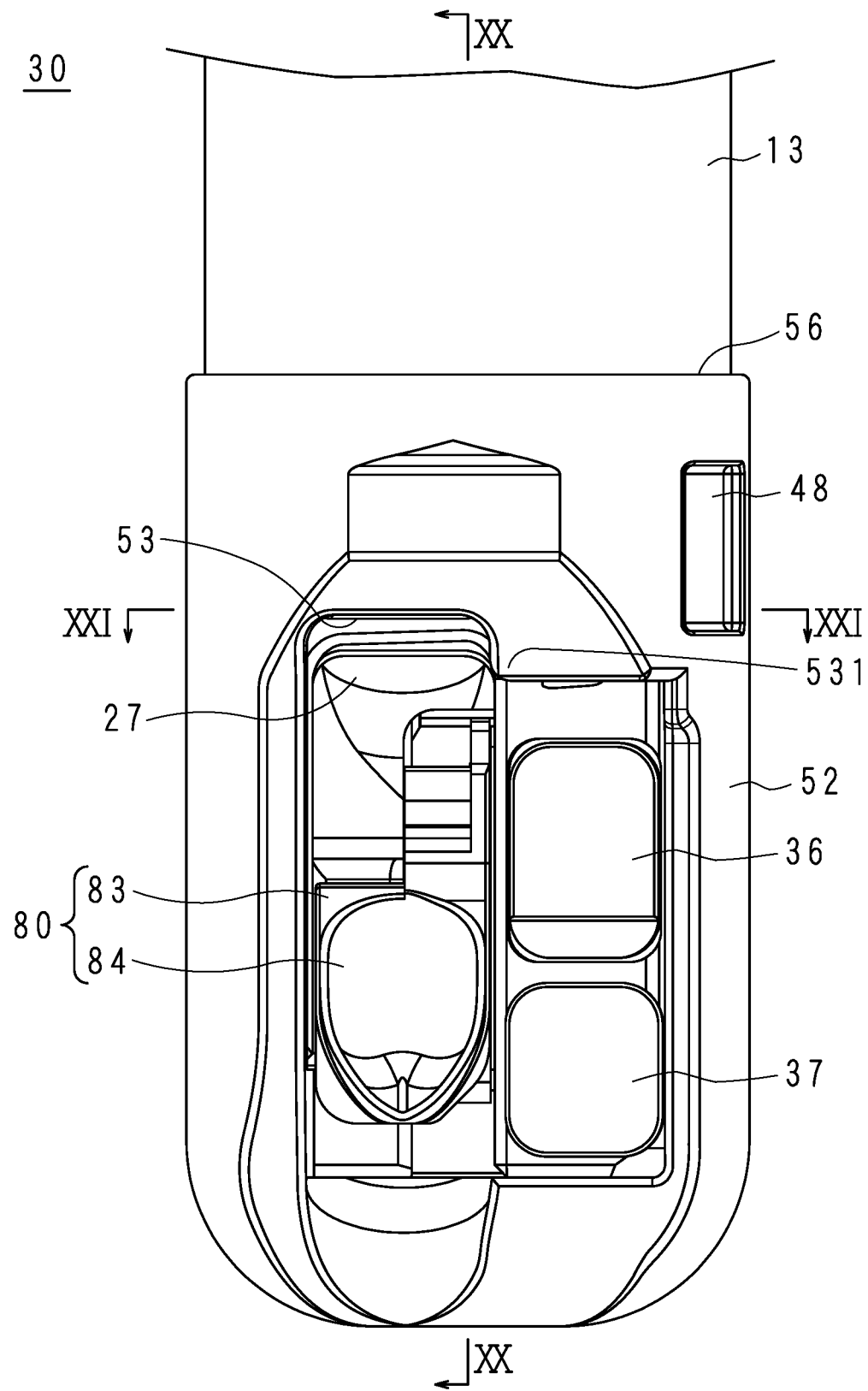
FIG. 4 is a front view of the distal end of the insertion portion.

FIG. 4 is a front view of the distal end of the insertion portion 30. The cover 52 has a rectangular concave portion 48 in the vicinity of an opening end portion 56. Each side of the concave portion 48 falls substantially vertically from the surface of the cover 52. The concave portion 48 is thinner than other portions of the cover 52 in the circumferential direction, and is a portion that is easily flexed when an external force is applied thereto by being pushed by a finger or the like. The concave portion 48 is an example of a flexible portion of the present embodiment.

FIG. 5 is a front view for describing a state where the endoscope cap 50 is detached from the distal end of the insertion portion 30. FIG. 6 is a back view illustrating a state where the endoscope cap 50 is detached from the distal end of the insertion portion 30. A user of the endoscope 10 holds the bending portion 13 with one hand and picks the cover 52 with two fingers of the other hand. At this time, when one of the two fingers pushes the concave portion 48, the other finger naturally pushes a region indicated by P in FIG. 6. The user can remove the endoscope cap 50 from the distal end of the insertion portion 30 as will be described later by pressing the cover 52 with the two fingers to slightly deform the cover 52 and then pull the cover 52 to the distal end side.

Figure 7:
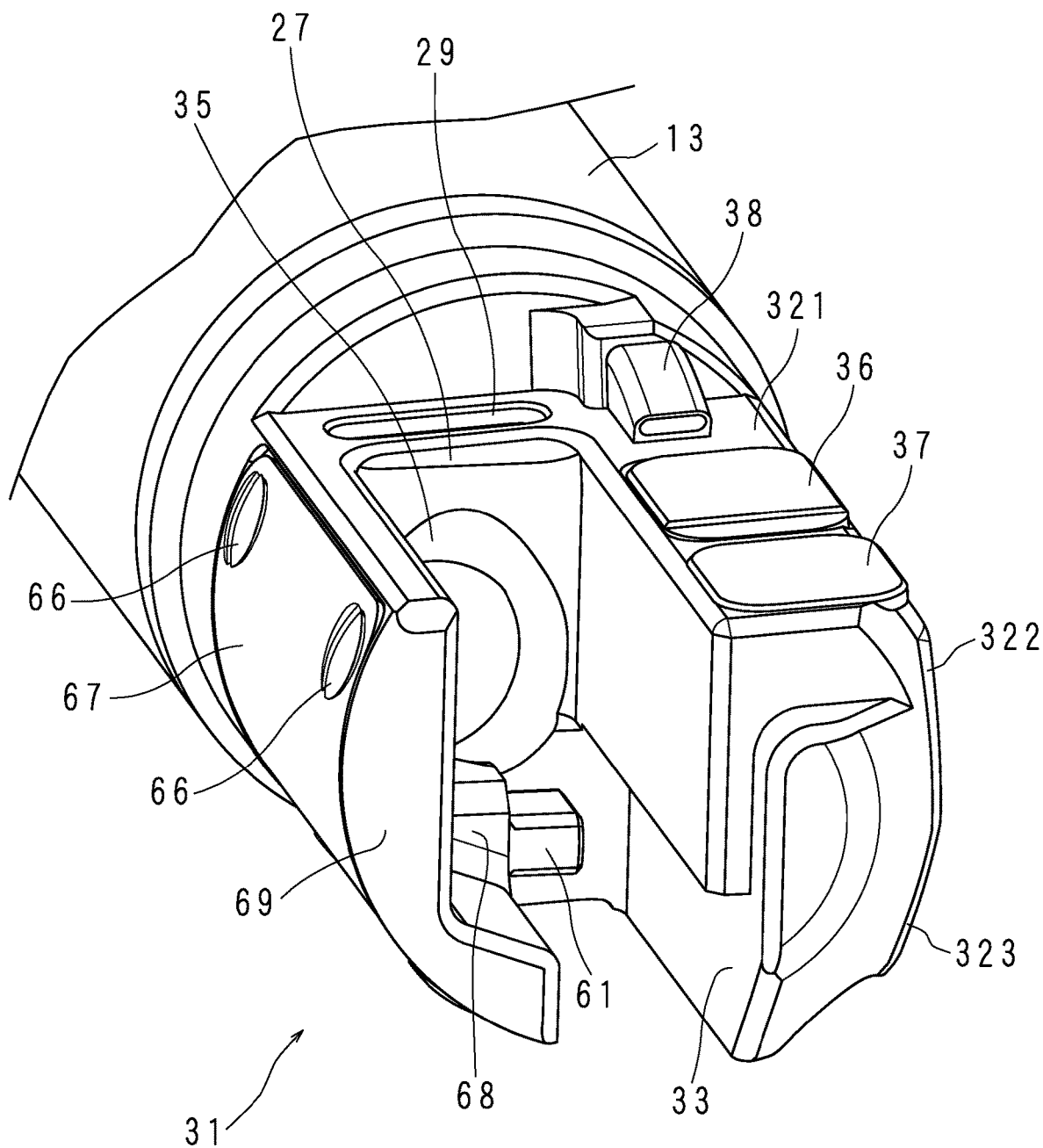
FIG. 7 is a perspective view of the distal end of the insertion portion from which the endoscope cap is detached.

FIG. 7 is a perspective view of the distal end of the insertion portion 30 from which the endoscope cap 50 is detached. The configuration of the distal end of the insertion portion 30 will be described with reference to FIGS. 5 to 7. The distal end portion 31 has a substantially cylindrical shape and is divided into an optical housing portion 33 and a lever chamber 69 by a groove provided from the distal end side toward the operation unit side at a position deviated from the center. The channel outlet 35 is open to a bottom of the groove. A curved portion 27 is provided in the vicinity of the channel outlet 35. A shape of the curved portion 27 will be described later.

The distal end portion 31 has a first flat surface portion 321 formed by cutting a part of a circumferential surface thereof into a flat shape. A third engagement portion 29 is provided on a portion of the first flat surface portion 321 along the bottom of the groove separating the optical housing portion 33 from the lever chamber 69. The third engagement portion 29 is an oval recess. The distal end portion 31 has a fourth engagement portion 28 (see FIG. 20) on the back side of the third engagement portion 29. The fourth engagement portion 28 is a rectangular recess.

The observation window 36 and the illumination window 37 are arranged on a side of the optical housing portion 33 of the first flat surface portion 321. A nozzle 38 that sprays water and air to the observation window 36 to clean the observation window 36 is provided on the operation unit side of the observation window 36. A second flat surface portion 322 and a third flat surface portion 323, formed by flatly cutting a part of the circumferential surface of the distal end portion 31, are formed on the outer side of the optical housing portion 33. The second flat surface portion 322 and the third flat surface portion 323 are continuous with an angle.

The lever chamber 69 is hollow and is covered with a rectangular thin plate-shaped lever chamber lid 67 along an outer circumferential surface of the distal end portion 31. The lever chamber lid 67 is fixed at four corners using a lid screw 66. The lid screw 66 is an example of a fixing member of the present embodiment. The lever chamber 69 has a support wall 68 on the optical housing portion 33 side. The raising base connection portion 61 protrudes from the support wall 68 toward the optical housing portion 33. The raising base connection portion 61 is an axis having a rectangular cross section. The raising base connection portion 61 will be described later.

Figure 8:
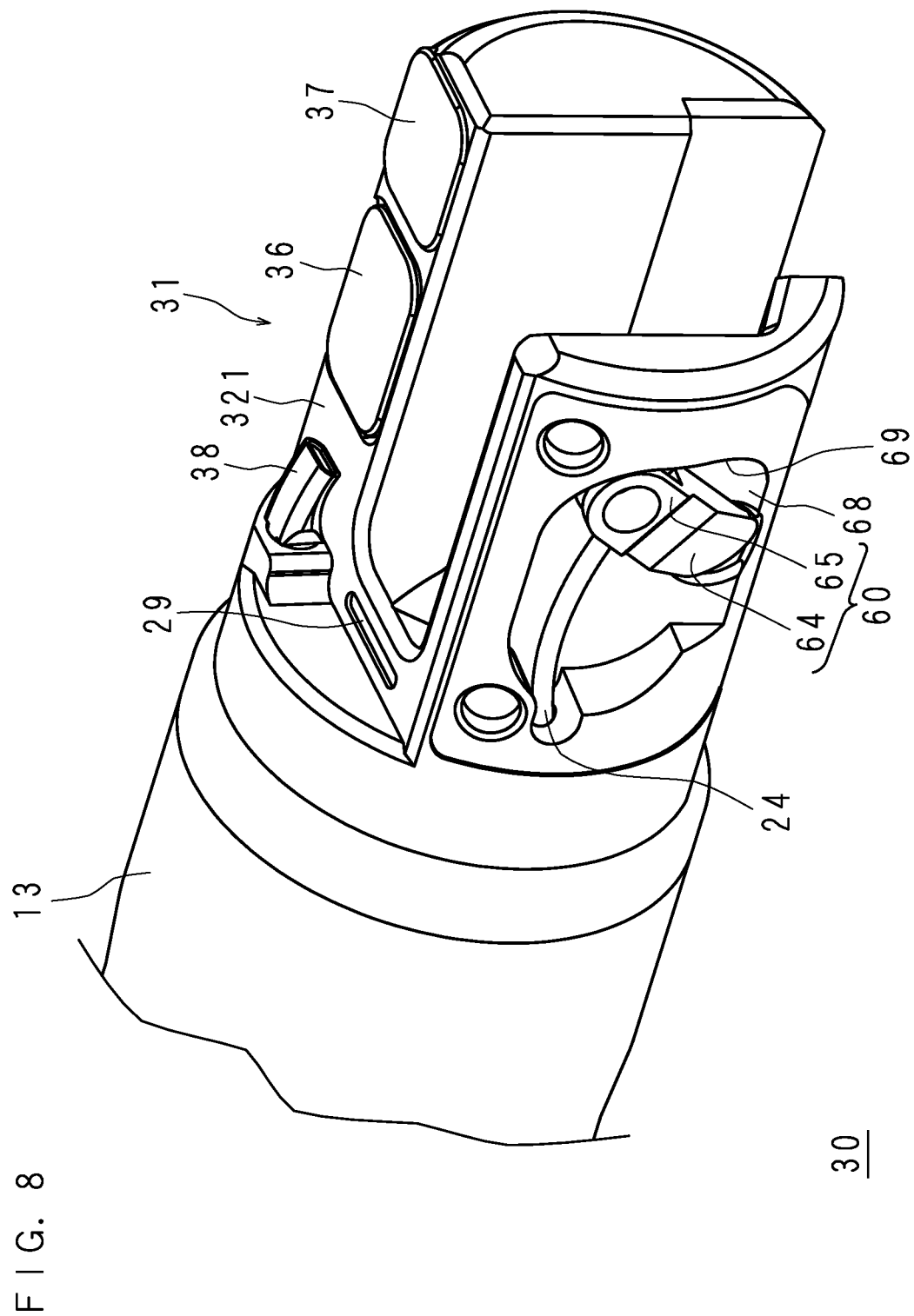
FIG. 8 is a perspective view of the distal end of the insertion portion with the endoscope cap and a lever chamber lid removed.

FIG. 8 is a perspective view of the distal end of the insertion portion 30 from which the endoscope cap 50 and the lever chamber lid 67 are detached. The lever 60 is provided inside the lever chamber 69. The lever 60 has a wire fixing portion 65 at one end and a lever shaft 63 (see FIG. 19) and the raising base connection portion 61 at the other end as will be described later. The lever 60 is rotatably supported by a hole provided in the support wall 68. Incidentally, the rotation means a rotational motion within a predetermined angle range.

The wire fixing portion 65 is connected to an end portion of the raising wire 24. The raising wire 24 is connected to the raising operation lever 21 (see FIG. 1) through the insertion portion 30. More specifically, the raising wire 24 is inserted through a guide pipe (not illustrated) having an inner diameter slightly larger than an outer diameter of the raising wire 24. The guide pipe (not illustrated) passes through the insertion portion 30 in a longitudinal direction. Thus, a distal end of the raising wire 24 moves forward and backward in conjunction with the operation of the raising operation lever 21. The raising wire 24 is an example of a rotating portion of the present embodiment. The raising wire 24 is remotely operated by the raising operation lever 21.

As the raising operation lever 21 moves, the raising wire 24 connected to the raising operation lever 21 is pulled toward the operation unit side. The lever 60 rotates about the lever shaft 63 as an axis as pulled by the raising wire 24.

Figure 9:
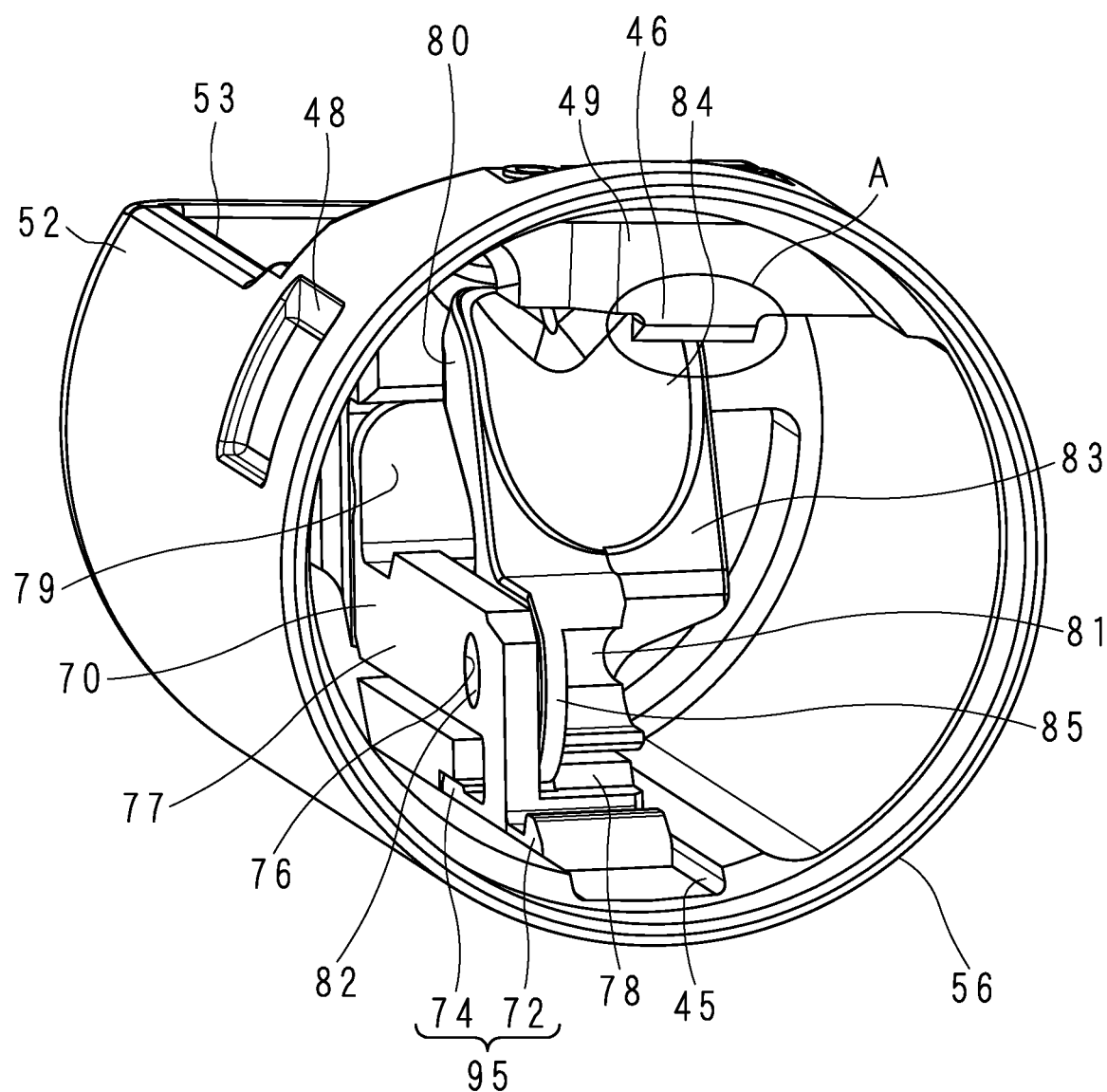
FIG. 9 is a perspective view of the endoscope cap as viewed from an attachment side with respect to the endoscope.
Figure 10:
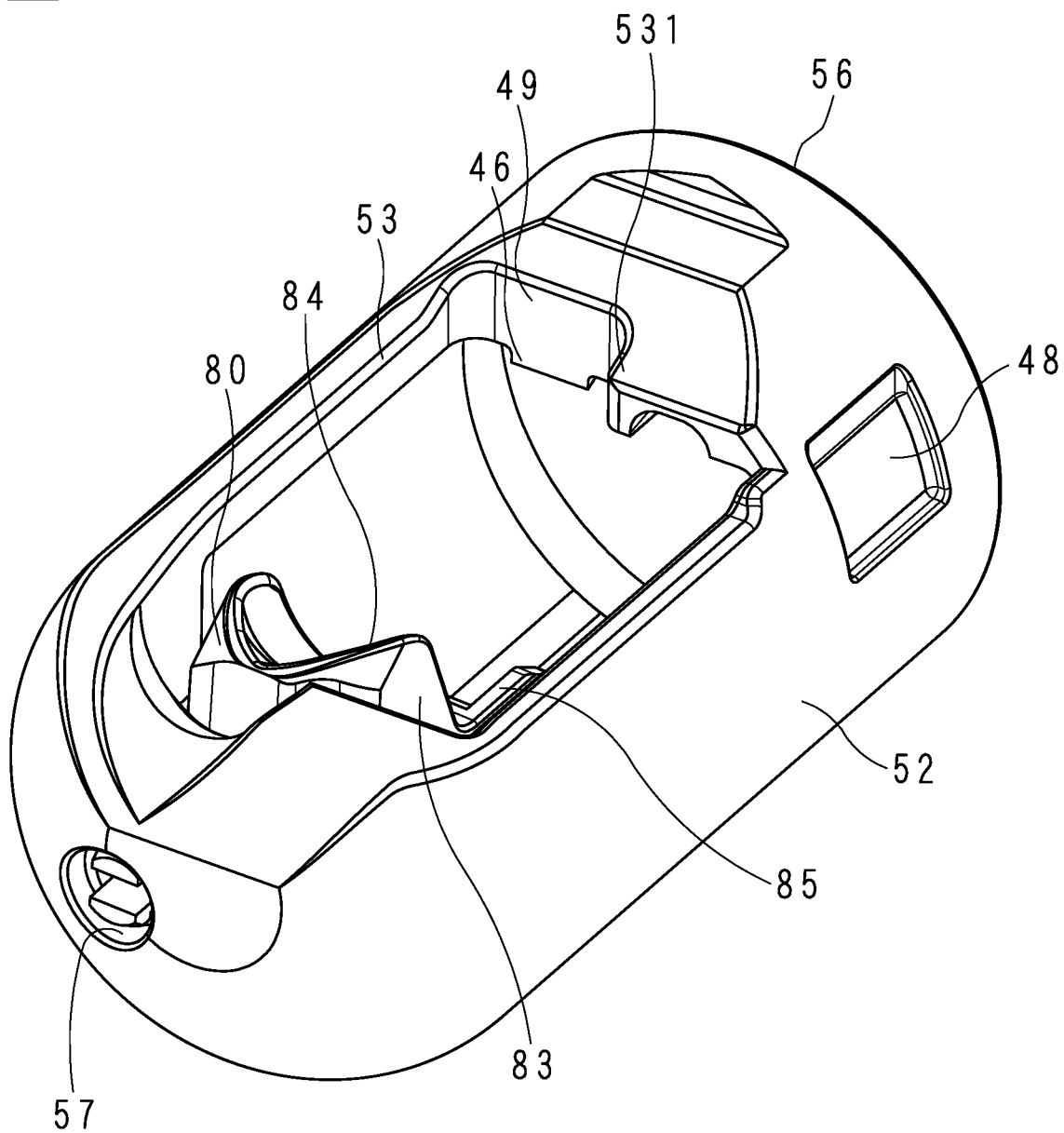
FIG. 10 is a perspective view of the endoscope cap as viewed from a bottom side of a cover.

FIG. 9 is a perspective view of the endoscope cap 50 as viewed from an attachment side with respect to the endoscope 10. FIG. 10 is a perspective view of the endoscope cap 50 as viewed from the bottom side of the cover 52. As described above, the endoscope cap 50 has the cover 52 and the raising base 80. The cover 52 is of a bottomed tube type having an opening portion at one end. As described above, the opening portion at one end of the cover 52 is referred to as the opening end portion 56.

As described above, the cover 52 has the window portion 53 in a tubular portion. The window portion 53 is open over substantially the entire length at one place on the circumferential surface of the cover 52. The cover 52 has a pedestal groove 45 extending from the opening end portion 56 toward the bottom, on an inner surface facing the window portion 53. The raising base 80 is attached to the inside of the cover 52 via the pedestal 70 fixed to the pedestal groove 45. The pedestal 70 will be described later.

The cover 52 has a plate-shaped protruding portion 49 that protrudes inward along an edge on the opening end portion 56 side of the window portion 53. A first engagement portion 46 is provided on a part of the distal end of the protruding portion 49 so as to protrude inward.

Figure 11:
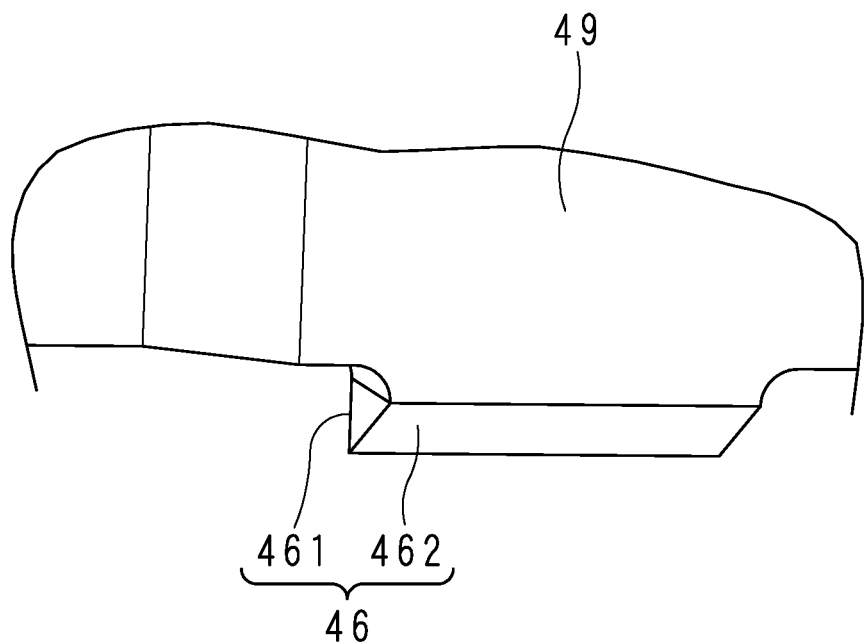
FIG. 11 is an enlarged perspective view of a first engagement portion.

FIG. 11 is an enlarged perspective view of the first engagement portion 46. FIG. 11 is an enlarged view of a part A in FIG. 9. A shape of the first engagement portion 46 will be described with reference to FIGS. 9 to 11. The first engagement portion 46 has a first wedge surface 461 on a bottom side and a second wedge surface 462 on the opening end portion 56 side. The first wedge surface 461 is a plane which is continuous with a surface of the protruding portion 49 on the bottom side and extends along an edge of the window portion 53.

The second wedge surface 462 is a plane which is inclined with respect to an axial direction of the tubular portion having the inside on the bottom side and the outside on the opening end portion side. When the first engagement portion 46 is cut by a surface parallel to the axis of the tubular portion, the first wedge surface 461 and the second wedge surface 462 are tapered into a wedge shape.

Figure 12:
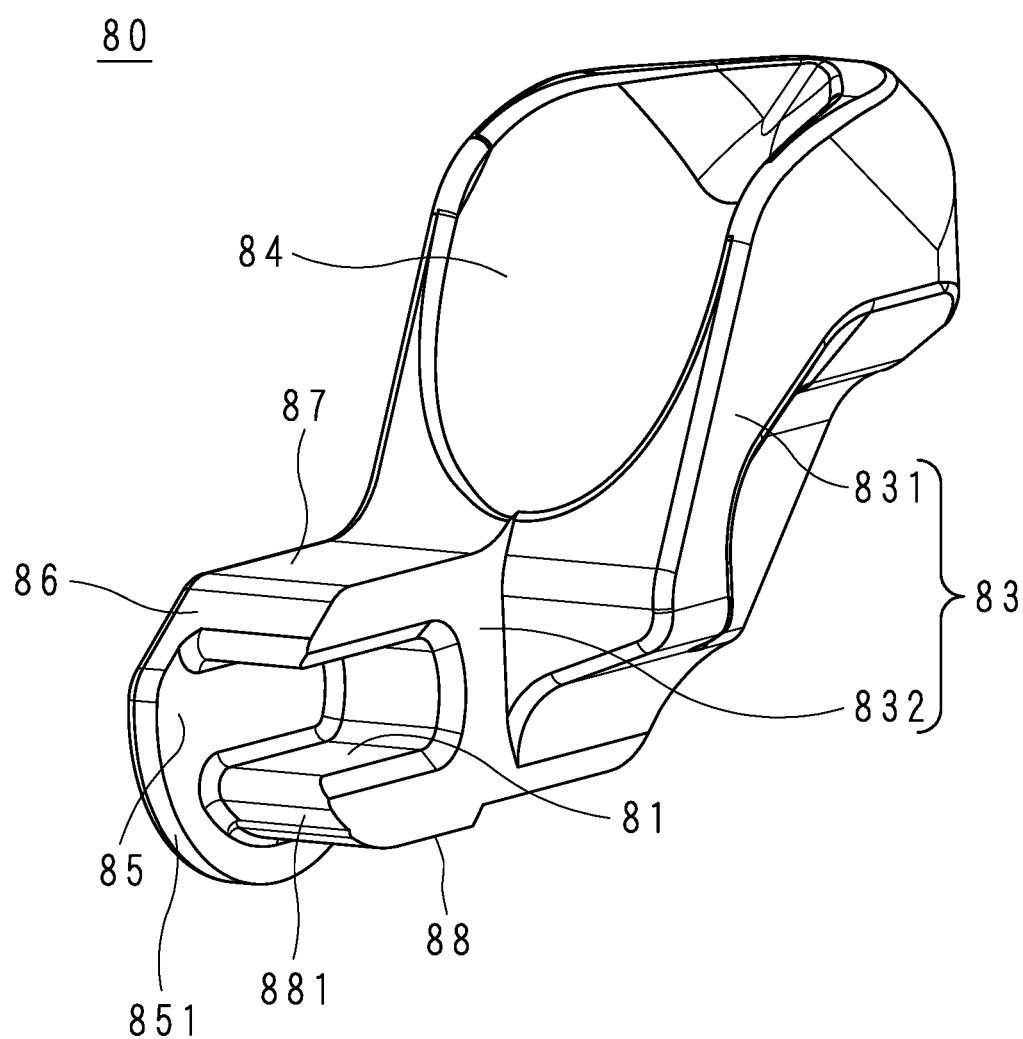
FIG. 12 is a perspective view of a raising base.
Figure 13:
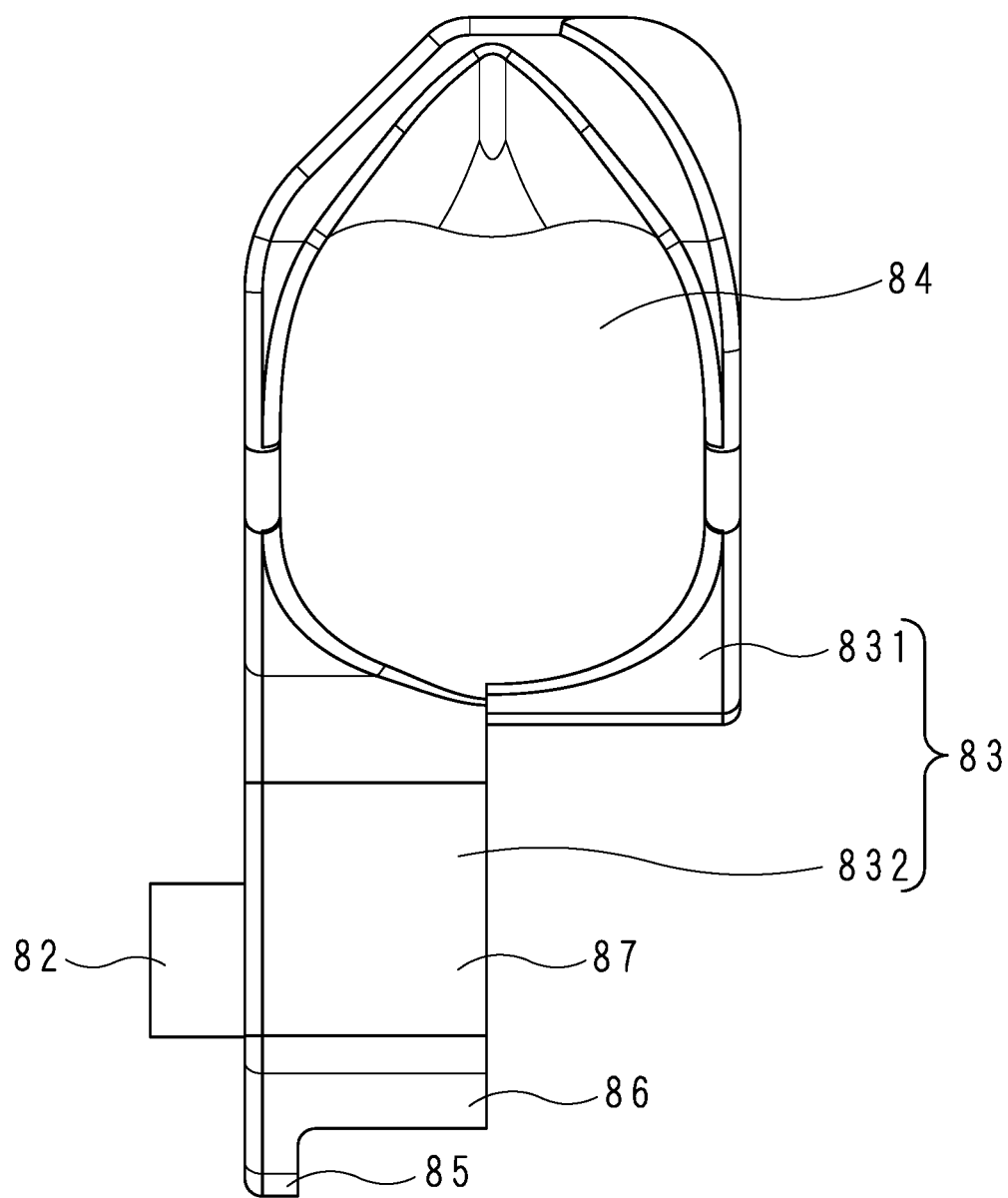
FIG. 13 is a front view of the raising base.
Figure 14:
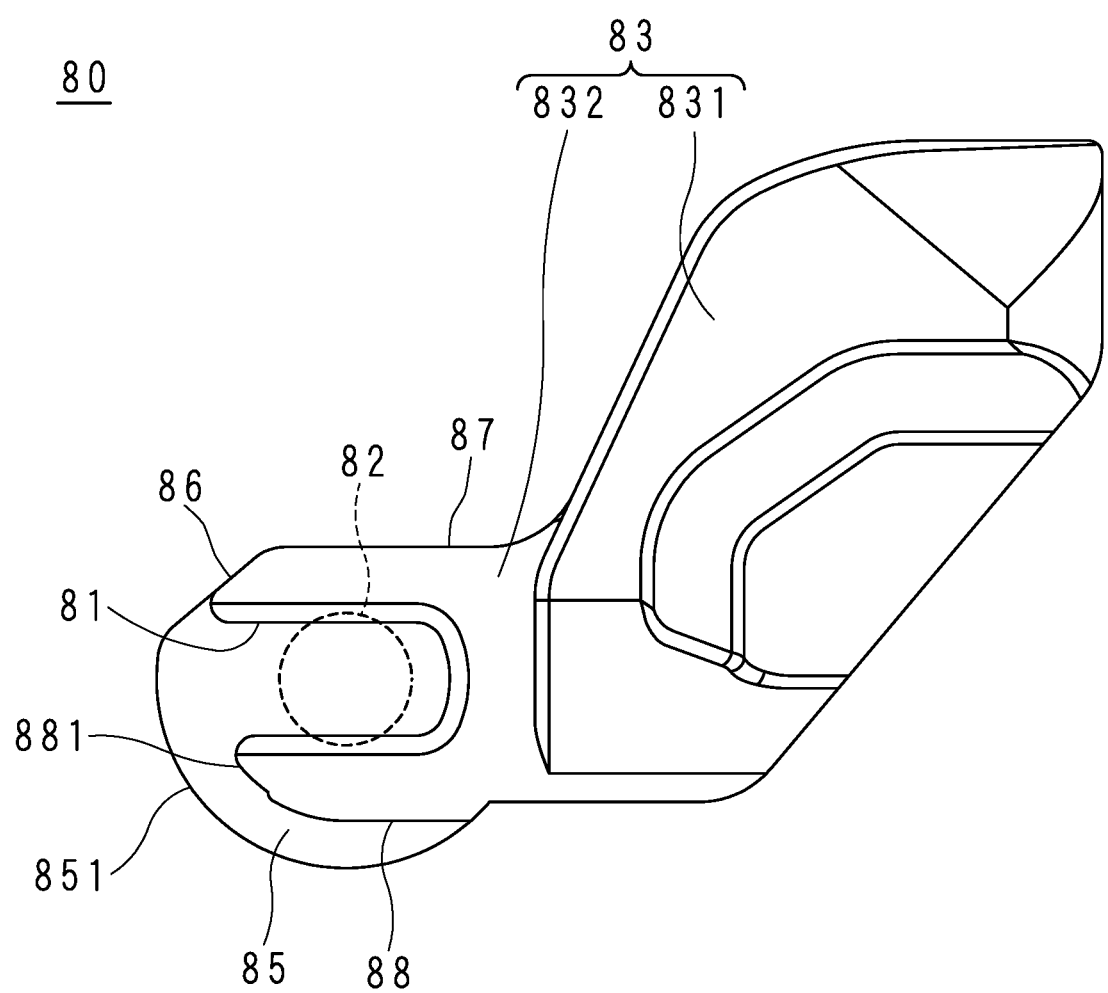
FIG. 14 is a side view of the raising base.

FIG. 12 is a perspective view of the raising base 80. FIG. 13 is a front view of the raising base 80. FIG. 14 is a side view of the raising base 80. The configuration of the raising base 80 will be described with reference to FIGS. 12 to 14.

The raising base 80 has a substantially L-shaped raising portion 83. The raising portion 83 has a first raising portion 831 having a spoon-shaped recessed portion 84 on one surface thereof and a second raising portion 832 protruding to the same side as a surface having the recessed portion 84 of the first raising portion 831 from an end of the first raising portion 831. A lever connection portion 81 is provided at an end portion of the second raising portion 832. The lever connection portion 81 is a U-shaped groove which is open toward the end portion of the second raising portion 832.

One side of the lever connection portion 81 is covered with a plate-shaped flange 85. A raising base shaft 82 protrudes from a surface opposite to the flange 85. That is, the raising base shaft 82 protrudes from one surface of the flange 85, and the raising portion 83 protrudes from the other surface of the flange 85 in a direction intersecting the central axis of the raising base shaft 82. The lever connection portion 81 is provided on a proximal end portion side of the raising portion 83.

The lever connection portion 81 is arranged so as to sandwich the central axis of the raising base shaft 82 as indicated by the broken line in FIG. 14. The flange 85 has a cylindrical surface 851 substantially coaxial with the raising base shaft 82.

The second raising portion 832 has a planar second flank surface 87 at a portion adjacent to the surface of the first raising portion 831 having the recessed portion 84. The second flank surface 87 is a flat surface parallel to a surface corresponding to two vertical lines of the U-shape of the lever connection portion 81.

The second raising portion 832 has a first flank surface 86 between the second flank surface 87 and an inlet of the lever connection portion 81. The first flank surface 86 is a flat surface arranged on the central axis side of the raising base shaft 82 with respect to an extension surface of the cylindrical surface 851 provided on the flange 85. An end of the first flank surface 86 on the flange 85 side is continuous with the cylindrical surface 851.

The second raising portion 832 has a stop surface 88 on the opposite side of the second flank surface 87 with the lever connection portion 81 interposed therebetween. The stop surface 88 is a flat surface parallel to the second flank surface 87. The stop surface 88 is arranged closer to the central axis side of the raising base shaft 82 than an extension surface of the cylindrical surface 851. The stop surface 88 is continuous with the inlet of the lever connection portion 81 via a substantially cylindrical-shaped rotary flank surface 881.

Figure 15:
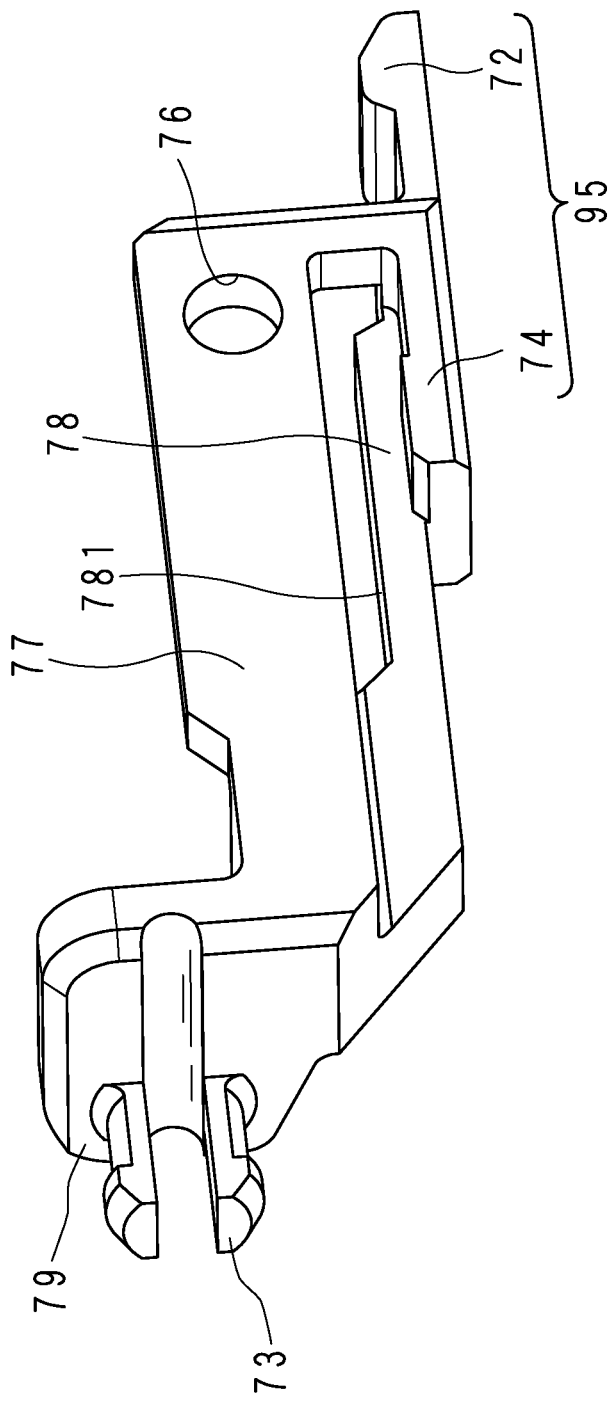
FIG. 15 is a perspective view of a pedestal.

FIG. 15 is a perspective view of the pedestal 70. A configuration of the pedestal 70 will be described with reference to FIG. 15.

The pedestal 70 has a rectangular plate-shaped base portion 95 and a substantially rectangular plate-shaped first wall 77 extending from a support leg rising from a central portion in the longitudinal direction of the base portion 95 along the longitudinal direction of the base portion 95.

Further, a substantially rectangular plate-shaped second wall 78 rises from the base portion 95 in parallel to the first wall 77. The first wall 77 and the second wall 78 are separated from each other in a width direction of the base portion 95. The second wall 78 has a second wall end surface 781 parallel to the base portion 95. The second wall end surface 781 is closer to the base portion 95 side than an edge of the first wall 77.

A rectangular plate-shaped third wall 79 that straddles the first wall 77 and the second wall 78 is connected to an end portion of the first wall 77. The third wall 79 is provided with a first fixing protrusion 73 on a surface opposite to the first wall 77. The first fixing protrusion 73 is a protrusion having a split groove. The first fixing protrusion 73 has a retainer which is slightly thick at an end portion thereof.

The base portion 95 has a thick portion 74 at one end in the longitudinal direction and a second engagement portion 72 which bulges in a substantially semicircular shape at the opposite end. The thick portion 74 opposes the first wall 77.

The first wall 77 has a raising base attachment hole 76 at the root thereof. The raising base shaft 82 of the raising base 80, which has been described with reference to FIGS. 12 to 14, is inserted into the raising base attachment hole 76 so that the raising base 80 and the pedestal 70 are rotatably assembled.

Figure 16:
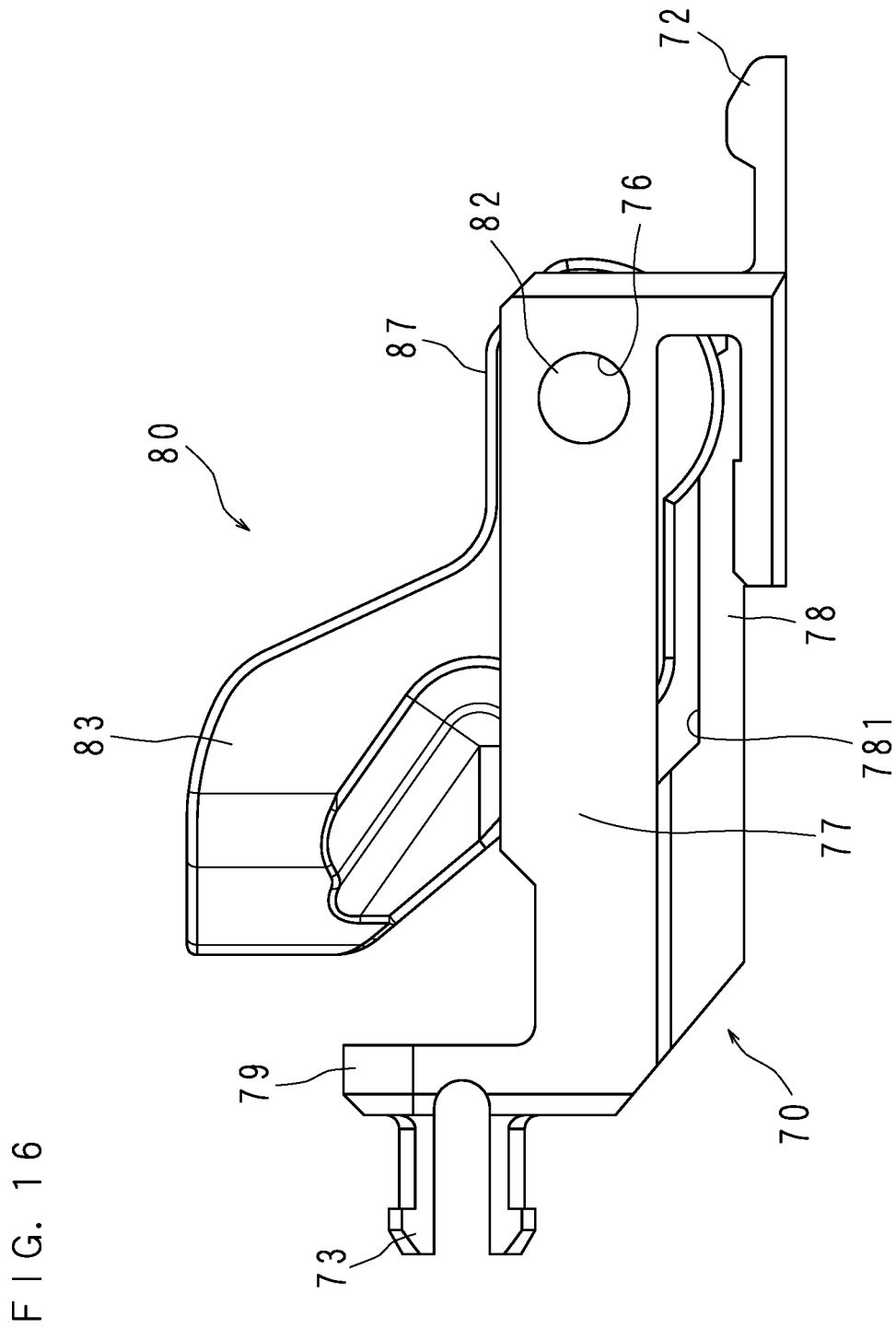
FIG. 16 is a front view in which the raising base and the pedestal are assembled.
Figure 17:
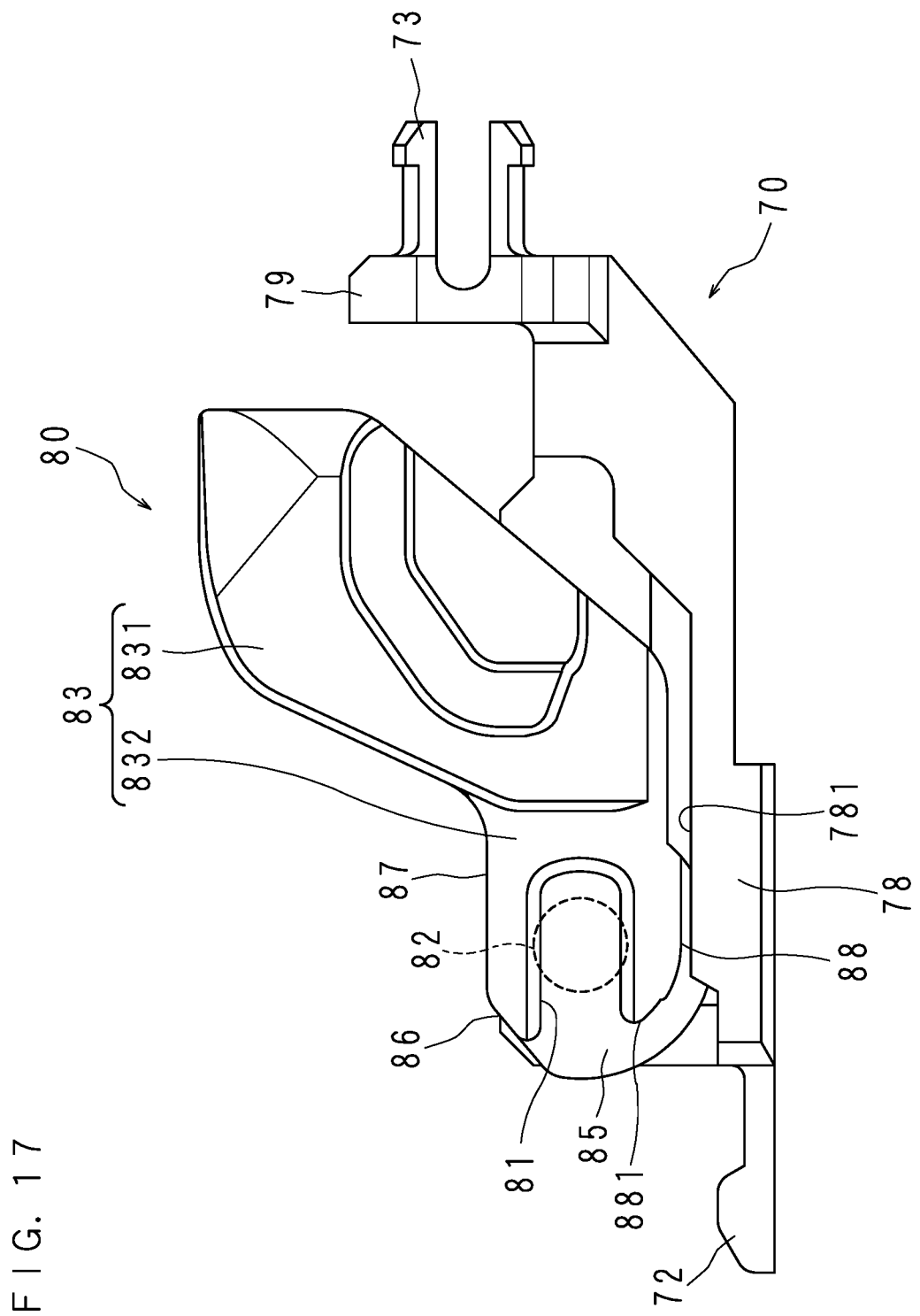
FIG. 17 is a back view in which the raising base and the pedestal are assembled.

FIG. 16 is a front view in which the raising base 80 and the pedestal 70 are assembled. FIG. 17 is a back view in which the raising base 80 and the pedestal 70 are assembled. A configuration in which the raising base 80 and the pedestal 70 are assembled will be described with reference to FIGS. 16 and 17.

As described above, the raising base shaft 82 is inserted into the raising base attachment hole 76. Since the raising base attachment hole 76 serves a function of a bearing, the raising base 80 is rotatable about the raising base shaft 82. The first wall 77 and the second wall 78 sandwich the flange 85. Since the flange 85 and the second wall 78 serve a function of a retainer, the raising base 80 is prevented from coming off the pedestal 70.

The stop surface 88 opposes the second wall end surface 781. When a force rotating clockwise in FIG. 17 about the raising base shaft 82 as an axis is applied to the raising base 80, the stop surface 88 comes into contact with the second wall 78 to prevent the raising base 80 from rotating. Meanwhile, the opening end portion 56 side of the stop surface 88 is continuous with the inlet of the lever connection portion 81 via the substantially cylindrical-shaped rotary flank surface 881, and thus, the raising base 80 can rotate counterclockwise in FIG. 17 about the raising base shaft 82 as the axis.

Returning to FIG. 9, the description will be continued. The pedestal 70 is inserted into the cover 52 from a side of the first fixing protrusion 73 in a state where the raising base 80 is rotatably attached to the raising base attachment hole 76. The base portion 95 of the pedestal 70 is fixed to the pedestal groove 45.

Figure 18:
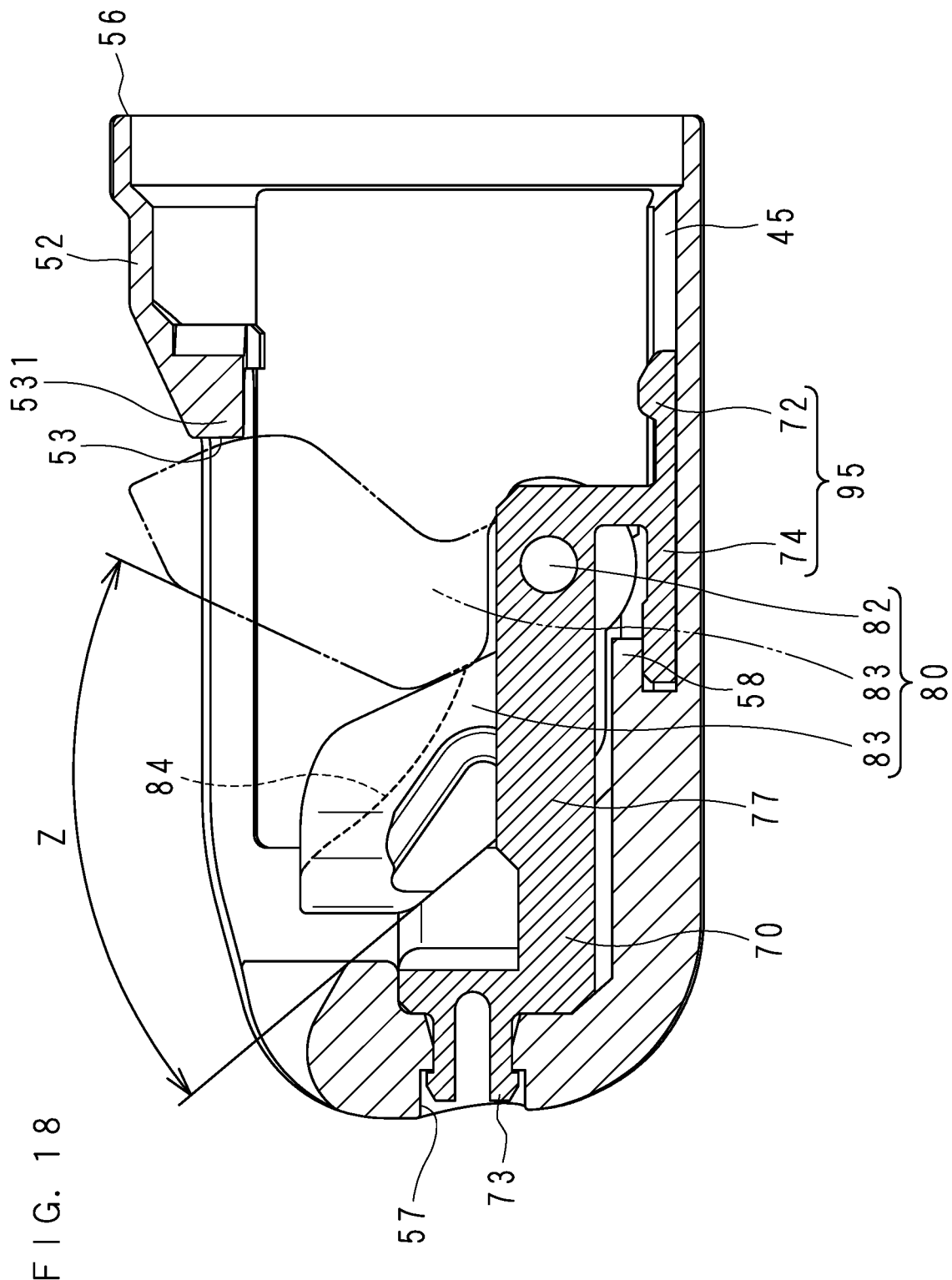
FIG. 18 is a cross-sectional view of the endoscope cap taken along line XVIII-XVIII of FIG. 5.

FIG. 18 is a cross-sectional view of the endoscope cap 50 taken along line XVIII-XVIII of FIG. 5. A XV-XV cross section is a cross section cutting the first wall 77 in a thickness direction along the longitudinal direction of the insertion portion 30. A configuration of the endoscope cap 50 will be described with reference to FIGS. 9 to 18.

As illustrated in FIG. 18, the cover 52 has a pedestal fixing hole 57 and a second fixing protrusion 58. The pedestal fixing hole 57 is a through-hole provided at the bottom of the cover 52. The second fixing protrusion 58 is a protrusion protruding from an end of the pedestal groove 45 toward the opening end portion 56 side.

The first fixing protrusion 73 and the thick portion 74, which have been described with reference to FIG. 15, are engaged with the pedestal fixing hole 57 and the second fixing protrusion 58, respectively, so that the cover 52 and the pedestal 70 are fixed inside the cover 52. The recessed portion 84 is arranged to oppose the window portion 53.

The raising base 80 can rotate about the raising base shaft 82 as the axis up to a position where an edge of the raising portion 83 comes into contact with the stopper portion 531 as indicated by the two-dot chain line in FIG. 18. In the following description, a rotatable angle of the raising base 80 is described as an angle Z.

Figure 19:
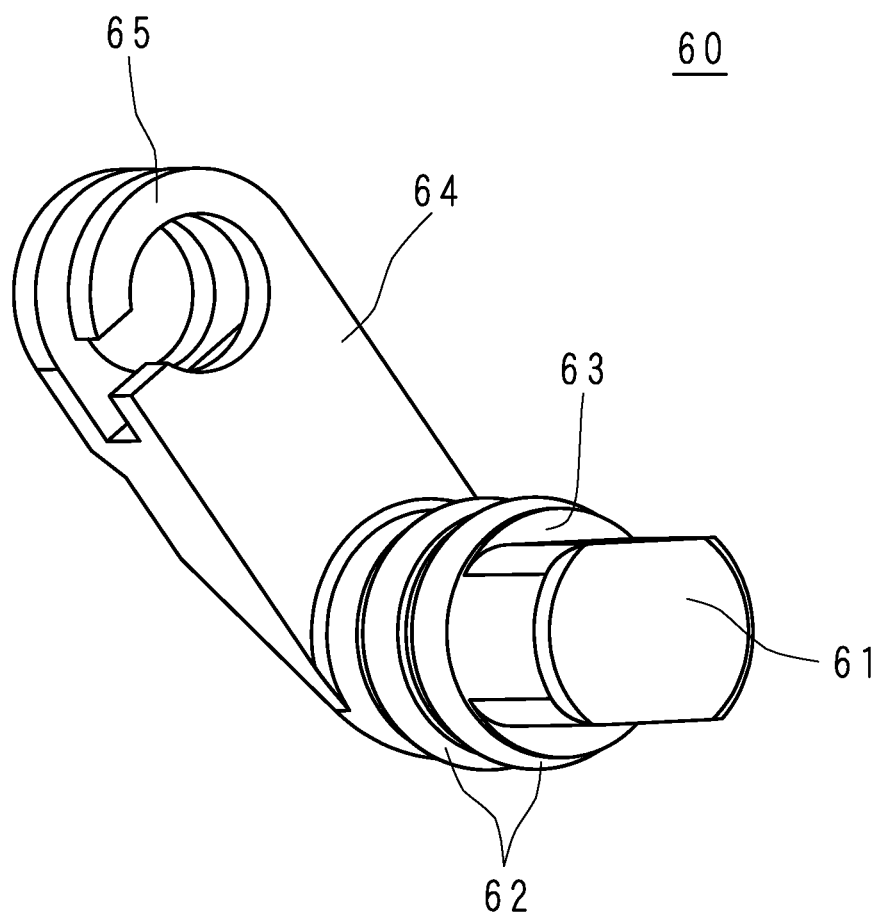
FIG. 19 is a perspective view of a lever.

FIG. 19 is a perspective view of the lever 60. The lever 60 has a lever shaft 63 at one end and a wire fixing portion 65 at the other end. The wire fixing portion 65 has a split groove. The raising base connection portion 61, which is the axis of the rectangular cross section, protrudes from one end surface of the lever shaft 63 in the same direction as the central axis of the lever shaft 63. In the following description, a plate-shaped portion connecting the lever shaft 63 and the wire fixing portion 65 is referred to as a rotating connection portion 64. The rotating connection portion 64 protrudes from the end portion of the lever shaft 63 on the opposite side of the raising base connection portion 61 in a direction intersecting the central axis of the lever shaft 63.

The rotating connection portion 64 rotates within the lever chamber 69 as illustrated in FIG. 8.

Two O-rings 62 are fixed to the lever shaft 63. Returning to FIG. 7, the description will be continued. The lever shaft 63 is inserted into a hole provided in the support wall 68 from the lever chamber 69 side, and the lever 60 is rotatably supported in a state where the raising base connection portion 61 faces the optical housing portion 33. The hollow lever chamber 69 is water-tightly sealed by the O-ring 62 and the lever chamber lid 67.

Figure 20:
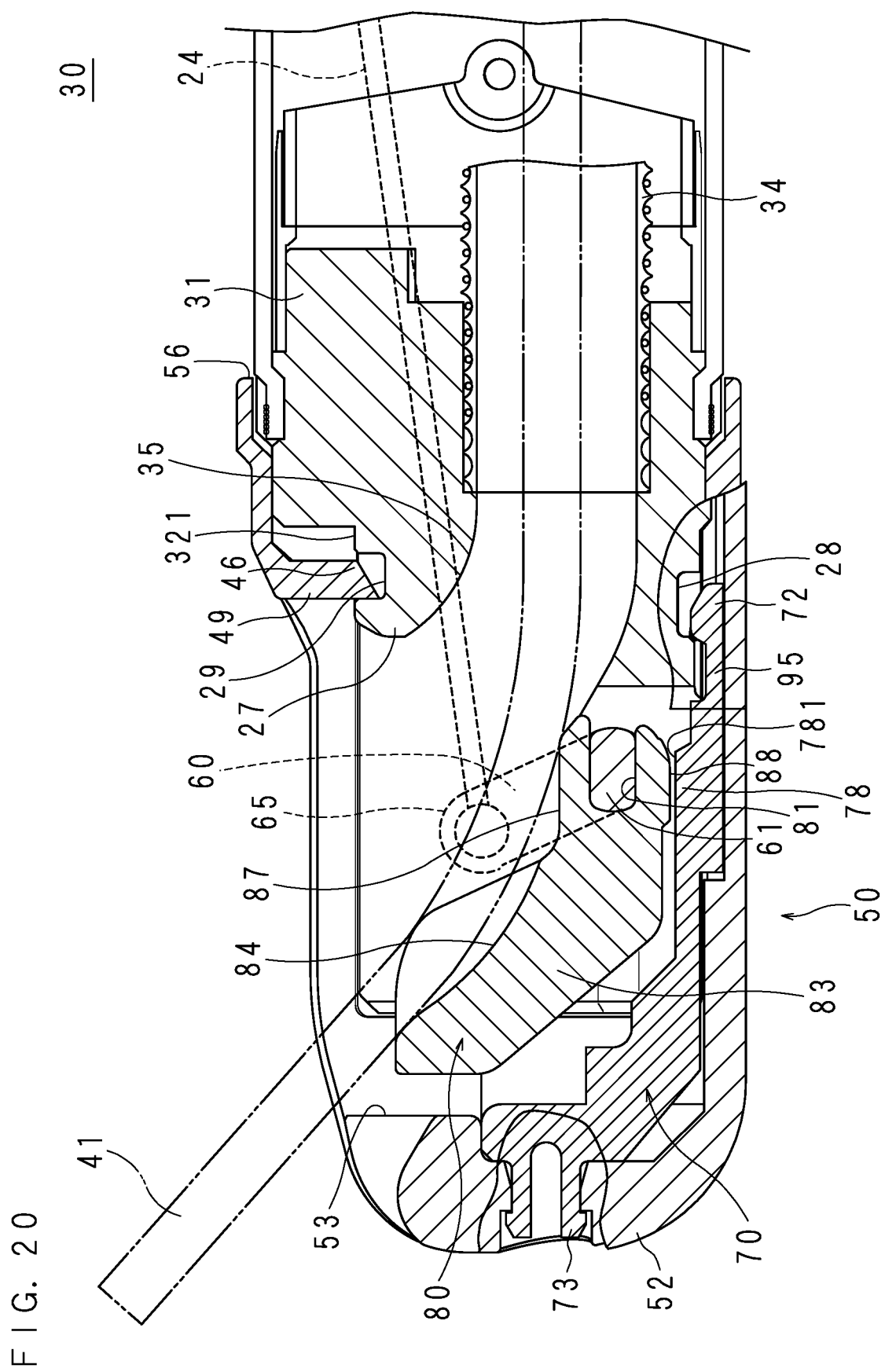
FIG. 20 is a cross-sectional view of the insertion portion taken along line XX-XX of FIG. 4.
Figure 21:
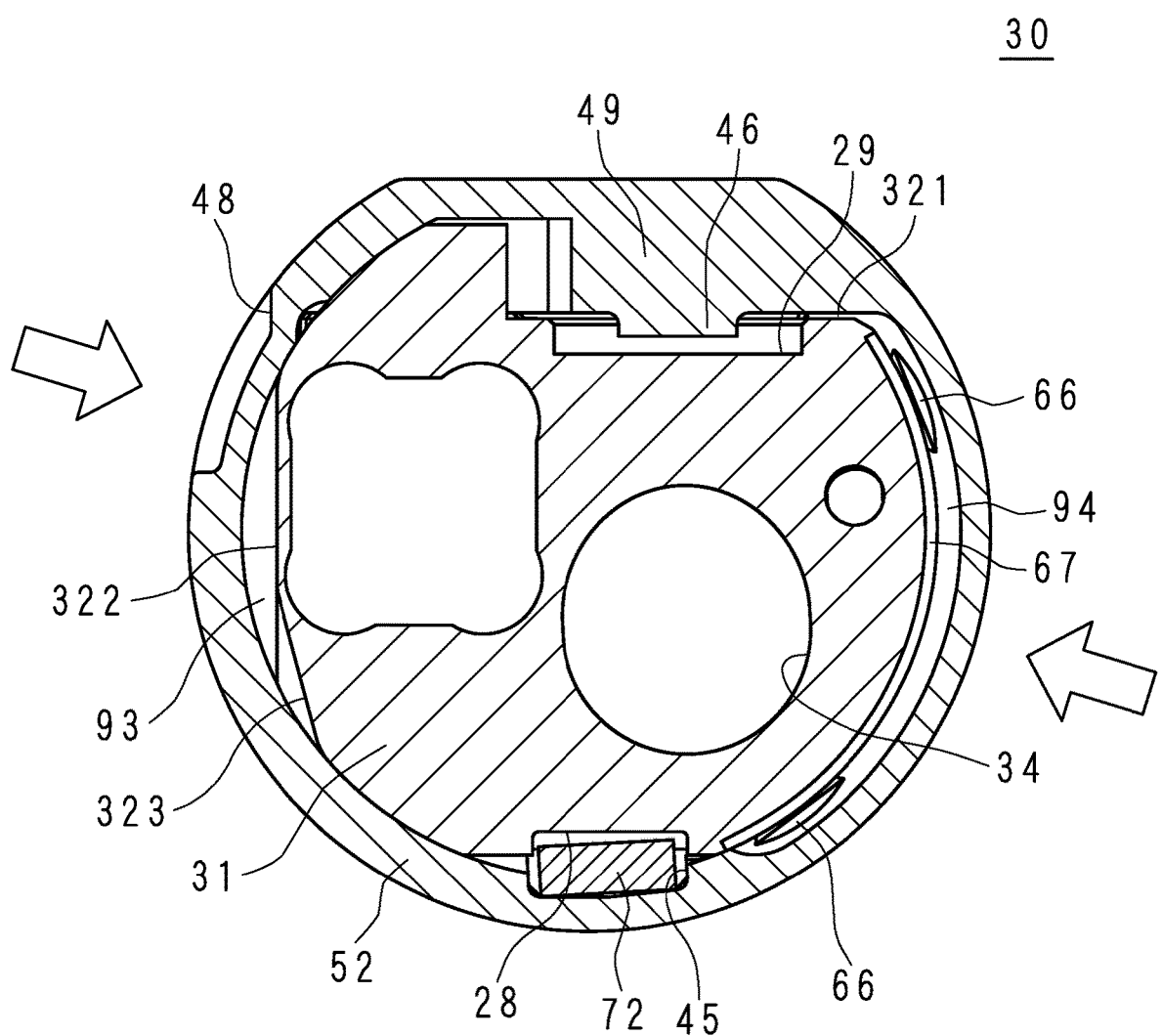
FIG. 21 is a cross-sectional view of the insertion portion taken along line XXI-XXI of FIG. 4.

FIG. 20 is a cross-sectional view of the insertion portion 30 taken along line XX-XX of FIG. 4. A XX-XX cross section is a cross section cutting the insertion portion 30 in the longitudinal direction at a position of the raising base connection portion 61. FIG. 21 is a cross-sectional view of the insertion portion 30 taken along line XXI-XXI of FIG. 4. A XXI-XXI cross section is a cross section cutting the longitudinal direction of the insertion portion 30 vertically at positions of the first engagement portion 46 and the second engagement portion 72. A configuration in which the endoscope cap 50 is fixed to the distal end of the insertion portion 30 will be described with reference to FIGS. 20 and 21.

The endoscope cap 50 has the opening end portion 56 facing the insertion portion 30 side. The first engagement portion 46 on an inner surface of the endoscope cap 50 is engaged with the third engagement portion 29 on the distal end portion 31. In the engagement portion, the first wedge surface 461 abuts on a surface of the third engagement portion 29 on the operation unit side.

Similarly, the second engagement portion 72 on the inner surface of the endoscope cap 50 is engaged with the fourth engagement portion 28 on the distal end portion 31. The endoscope cap 50 is fixed to the distal end portion 31 as the endoscope cap 50 is engaged with the distal end portion 31 at two opposing places on the inner surface.

As illustrated in FIG. 20, the first engagement portion 46 is arranged closer to the opening end portion 56 side than the second engagement portion 72. In addition, the engagement portions of the first engagement portion 46 and the third engagement portion 29 engage with each other as flat surfaces thereof abut on each other, whereas the second engagement portion 72 is engaged with the fourth engagement portion 28 on a rounded surface thereof. Therefore, the first engagement portion 46 is more firmly engaged with the distal end portion 31 than the second engagement portion 72.

The raising base connection portion 61, which is the axis of the rectangular cross section, is inserted into the lever connection portion 81 of the U-shaped groove type. As a result, the lever 60 is engaged with the raising base 80.

As illustrated in FIG. 21, an inner surface of the tubular portion of the cover 52 opposes the second flat surface portion 322 and the third flat surface portion 323 with a space therebetween, thereby forming a first cavity portion 93. The concave portion 48 is arranged at a position corresponding to the first cavity portion 93. The cover 52 is dented on the inner surface of the tubular portion to be thin on the opposite side of the concave portion 48. The inner surface of the thin portion of the cover 52 and the lever chamber lid 67 oppose each other with a space therebetween, thereby forming a second cavity portion 94. A head portion of the lid screw 66 is arranged inside the second cavity portion 94. That is, the second cavity portion 94 is a space for housing the head portion of the lid screw 66 which is the fixing member that fixes the lever chamber lid 67.

When detaching the endoscope cap 50, the user presses two places of the concave portion 48 and the opposite side thereof with fingers as indicated by the white arrows in FIG. 21. The cover 52 is deformed since the first cavity portion 93 and the second cavity portion 94 exist on the back side of portions to be pressed. Incidentally, the concave portion 48 is thinner than the other portion in the circumferential direction of the cover 52 as described above, and is a flexible portion that is easily flexed by being pushed with the finger or the like. Thus, the user can easily deform the endoscope cap 50.

Figure 22:
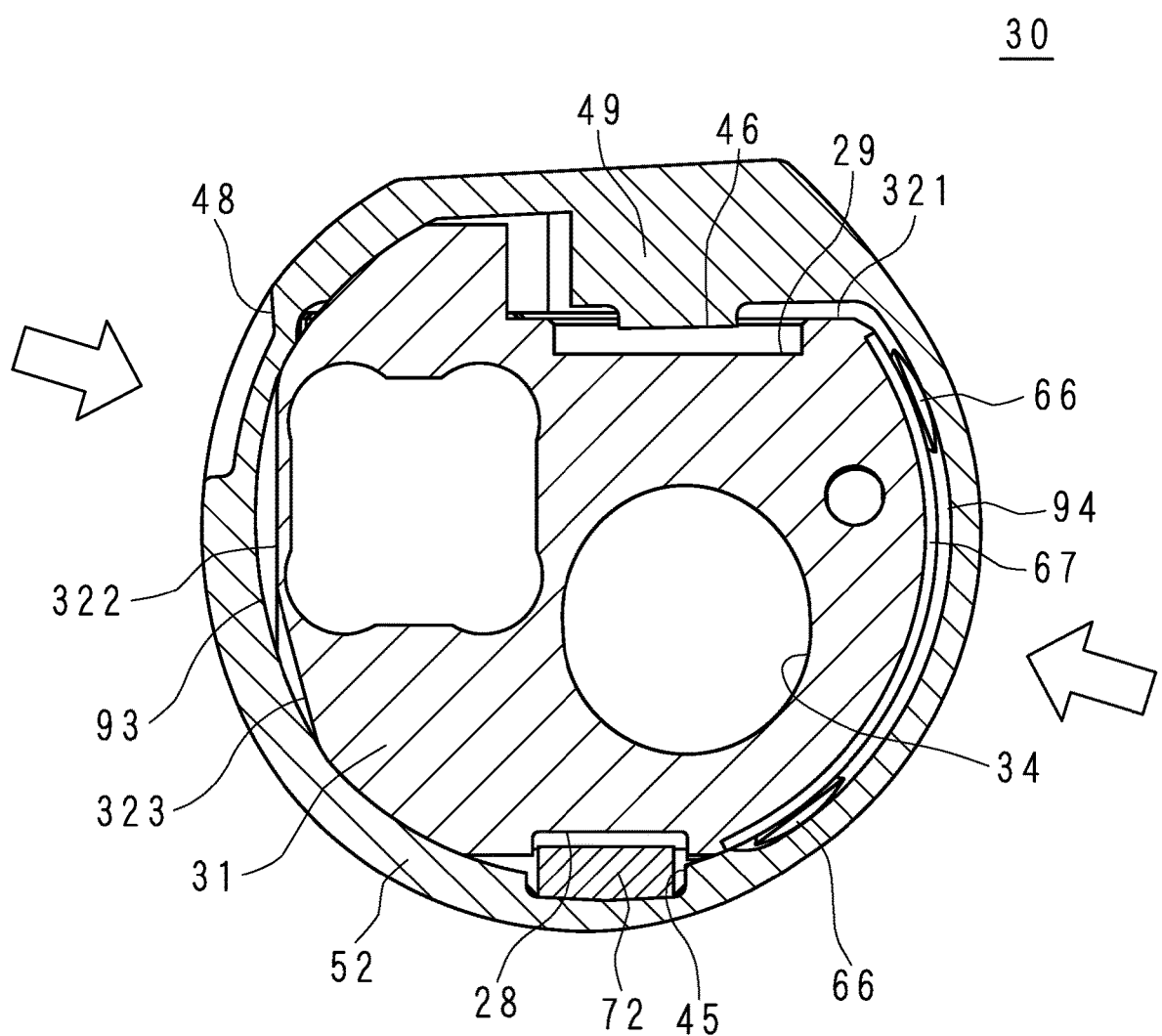
FIG. 22 is a cross-sectional view of the insertion portion deformed by pressing the cover.

FIG. 22 is a cross-sectional view of the insertion portion 30 deformed by pressing the cover 52. FIG. 22 illustrates the same cross section as FIG. 21. In the cover 52, the pressed portions move inward, and a portion between the pressed portions is deformed so as to bulge outward. The first engagement portion 46 and the second engagement portion 72 are arranged at the bulging position, and thus, move outward. Due to this deformation, the engagement between the first engagement portion 46 and the third engagement portion 29 and the engagement between the second engagement portion 72 and the fourth engagement portion 28 are released.

As the user pulls the endoscope cap 50 to the distal end side while pressing the endoscope cap 50, the engagement between the lever connection portion 81 and the raising base connection portion 61 is also released, and it is possible to remove the endoscope cap 50 from the distal end of the insertion portion 30. As illustrated in FIG. 4, the concave portion 48 has a side orthogonal to the insertion direction. Thus, the finger of the user is caught by the edge of the concave portion 48, and the endoscope cap 50 can be easily detached.

Incidentally, the user can attach the endoscope cap 50 to the insertion portion 30 by confirming that a direction of the lever connection portion 81 and a direction of the raising base connection portion 61 are aligned, and then, pushing the endoscope cap 50 into the distal end of the insertion portion 30. As illustrated in FIG. 11, the second wedge surface 462 of the first engagement portion 46 is inclined with respect to the longitudinal direction of the tubular portion of the cover 52, and thus, the first engagement portion 46 is hardly caught by the distal end portion 31 so that the attachment is easy.

As illustrated in FIG. 20, the tube-shaped channel 34 is connected to the channel outlet 35 provided at the distal end portion 31. The channel outlet 35 spreads in a trumpet shape toward the window portion 53. The curved portion 27 that gently protrudes toward the distal end side is provided in the vicinity of the third engagement portion 29 of the channel outlet 35, that is, on a peripheral edge portion on a side where the raising base 80 rises as viewed from the channel outlet 35.

Figure 23:
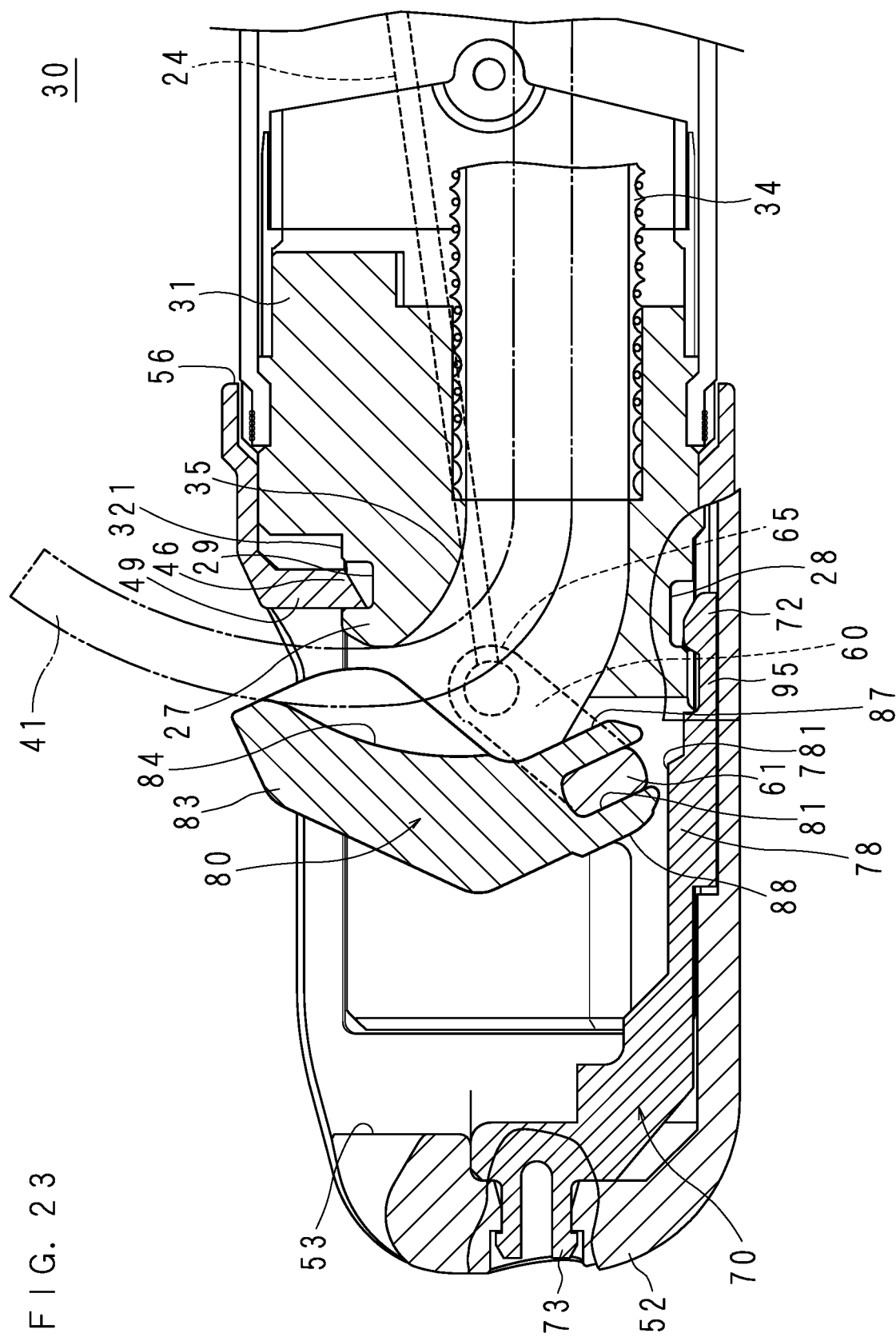
FIG. 23 is a cross-sectional view of the insertion portion with the raising base raised.

FIG. 23 is a cross-sectional view of the insertion portion 30 with the raising base 80 raised. FIG. 23 illustrates the same cross section as FIG. 20. A configuration for raising the raising base 80 will be described with reference to FIGS. 7, 8, 19, 20, and 21.

The lever shaft 63 is inserted through a through-hole provided in the support wall 68 from the lever chamber 69 side, and the raising base connection portion 61 protrudes to the opposite side of the support wall 68 as illustrated in FIG. 7. As described above, the lever chamber 69 is water-tightly sealed by the O-ring 62 and the lever chamber lid 67 (see FIG. 5). Therefore, body fluid or the like does not adhere to the inside of the lever chamber 69 and a path of the raising wire 24 during the use of the endoscope 10.

The raising base 80 is housed inside the cover 52 in the state illustrated in FIG. 20. The recessed portion 84 is arranged at a position where the treatment tool distal end portion 41 protruding from the channel outlet 35 can be gently curved upward in FIG. 20.

As described above, the lever 60 rotates about the lever shaft 63 as the axis as the user operates the raising operation lever 21. The raising base connection portion 61 rotates integrally with the lever shaft 63. Since the raising base connection portion 61 is connected to the lever connection portion 81, the raising base 80 also rotates to rise together with the lever 60. As a result, a distance between the raising base 80 and the window portion 53 changes.

FIG. 23 illustrates a state where the raising base 80 is rotated. The treatment tool distal end portion 41 protruding from the channel outlet 35 is raised as being pushed by the raising base 80. The treatment tool distal end portion 41 is pushed further into the operation unit side by the edge on the distal end side of the recessed portion 84 from the state of being pushed against the distal end of the curved portion 27. Therefore, it is possible to bend the treatment tool distal end portion 41 at an angle larger than the rotatable angle Z of the raising base 80 which has been described with reference to FIG. 18.

An overview of a method of using the endoscope 10 of the present embodiment will be described. The endoscope 10 is stored in a state where the endoscope cap 50 has been removed and cleaning or the like has been performed. The endoscope caps 50 are provided in the state of being enclosed in sterilization packs one by one, for example, in the state of being placed in a paper box in units of ten and then subjected to electron beam sterilization. The number of the endoscope caps 50 to be placed in the paper box is desirably a minimum sales unit, that is, a minimum unit to be sold to the user at one time.

Incidentally, materials of the cover 52, the pedestal 70 and the raising base 80, which are components of the endoscope cap 50, are desirably materials which are highly durable for electron beam sterilization such as polypropylene and polycarbonate of a radiation resistance grade. The cover 52 may be formed by integrating resin such as polycarbonate and rubber such as silicone rubber by insert-molding, adhesion, or the like. When rubber is partially used to make the cover 52 thin, it is possible to make the endoscope 10 slim.

The user takes out the endoscope cap 50 from the sterilization pack. The user attaches the endoscope cap 50 to the insertion portion 30 by confirming that the orientation of the lever connection portion 81 and the orientation of the raising base connection portion 61 are aligned, and then, pushing the endoscope cap 50 into the distal end of the insertion portion 30. As described above, the second wedge surface 462 of the first engagement portion 46 is inclined with respect to the longitudinal direction of the tubular portion of the cover 52, and thus, the first engagement portion 46 is hardly caught by the distal end portion 31 so that the attachment is easy.

When the first wedge surface 461 gets over a surface of the third engagement portion 29 on the operation unit side, the first engagement portion 46 elastically returns to be engaged with the third engagement portion 29. The first wedge surface 461 and the surface of the third engagement portion 29 on the operation unit side opposing each other are flat surfaces perpendicular to the insertion direction, and thus, are reliably engaged with each other. The user confirms that the endoscope cap 50 is firmly fixed to the distal end of the insertion portion 30 by lightly pulling the endoscope cap 50 or the like.

The user inserts the insertion portion 30 from a mouth of a person to be examined. The user guides the distal end of the insertion portion 30 to a target site while observing a captured image through the observation window 36. The user inserts the treatment tool 40 or the like from the channel inlet 22 in accordance with a purpose. After confirming that the treatment tool distal end portion 41 protrudes from the distal end of the insertion portion 30 and is positioned in the vicinity of the target site, the user operates the raising operation lever 21 to guide the treatment tool distal end portion 41 to the target site. After performing a necessary measure and the like, the user removes the treatment tool 40 from the channel 34. The user removes the endoscope 10 from the subject to be examined and ends the examination or treatment.

As described above, the cover 52 can be easily detached by pulling the cover 52 to the distal end side while pressing the cover 52 with the two fingers. The endoscope cap 50 of the present embodiment is a so-called single use, and is discarded after being used once.

Incidentally, it is difficult to consider a case where an external force enough to deform the cover 52 is applied simultaneously at two portions of the cover 52 when observation and treatment are performed using the endoscope 10 by a general method.

The user performs processing such as cleaning on the endoscope 10 after removing the endoscope cap 50 in preparation for the next use. The raising base 80 is not attached to the endoscope 10 after the endoscope cap 50 has been removed as illustrated in FIG. 7. The raising base connection portion 61 used for fixing the raising base 80 is exposed at the distal end portion 31 as illustrated in FIG. 7.

As described above, the endoscope 10 of the present embodiment does not need any special cleaning work or the like to clean the complicated structure in the vicinity of the raising base 80 and the raising wire 24. Therefore, it is possible to provide the endoscope 10 with the raising base which can be operated efficiently with a short processing time between cases. According to the present embodiment, easy cleaning of the endoscope 10 by detachably attaching the endoscope cap 50, and improvement of operability before and after an endoscopic examination procedure, that is, facilitating the operation of attaching and detaching the endoscope cap 50 to and from the endoscope 10 can be made compatible.

A slit or the like may be provided on an edge of the pedestal fixing hole 57, which has been described with reference to FIG. 18, such that the pedestal fixing hole 57 is broken and the first fixing protrusion 73 is removed from the pedestal fixing hole 57 when the endoscope cap 50 is removed from the distal end portion 31. The pedestal 70 and the raising base 80 remaining on the distal end portion 31 side can be easily removed and discarded by the user with hands. It is possible to provide the endoscope cap 50 which is disassembled simultaneously with detachment so as to prevent erroneous reuse of the user.

A slit or the like may be provided at the root of the first engagement portion 46 so that the first engagement portion 46 is broken when the endoscope cap 50 is removed from the distal end portion 31. A slit or the like may be provided at the root of the second engagement portion 72 so that the second engagement portion 72 is broken when the endoscope cap 50 is removed from the distal end portion 31. When the first engagement portion 46 or the second engagement portion 72 is broken, it becomes difficult to fix the endoscope cap 50 to the distal end portion 31, and thus, it is possible to provide the endoscope cap 50 which prevents the erroneous reuse of the user.

The stop surface 88 is not necessarily parallel to the surface corresponding to the two vertical lines of the U-shape of the lever connection portion 81. For example, when the stop surface 88 is inclined to the left downward direction in FIG. 20, the raising base 80 can rotate counter-clockwise from the state illustrated in FIG. 20. In this manner, it is possible to provide the endoscope 10 which can insert the treatment tool 40 without strongly bending the treatment tool distal end portion 41.

When raising the treatment tool 40 having a high rigidity, the raising portion 83 is pushed back by a force that tries to return the treatment tool 40 to a straight state. At this time, a force to twist the endoscope cap 50 in the counterclockwise direction in FIG. 23 is applied with the second engagement portion 72 as the axis.

Since the first engagement portion 46 is arranged closer to the opening end portion 56 side than the second engagement portion 72, and the first engagement portion 46 is more firmly engaged with the distal end portion 31 than the second engagement portion 72 as described above, the endoscope cap 50 is hardly removed from the insertion portion 30. Incidentally, it is possible to further make it difficult for the endoscope cap 50 to be removed from the insertion portion 30 by setting the protruding amount of the first engagement portion 46 to be larger than the protruding amount of the second engagement portion 72.

The endoscope 10 of the present embodiment is provided with the raising base 80 and is the side-view type, and thus, is suitable for diagnosis and treatment of duodenum and a pancreaticobiliary region. In particular, the endoscope 10 of the present embodiment is suitable when performing procedures such as endoscopic retrograde cholangio pancreatography (ERCP), endoscopic sphincterotomy (EST), and endoscopic biliary drainage (EBD). This is because the treatment tool 40 is guided inside duodenal papilla on a duodenal wall and a pancreatic duct and a common bile duct which are open to the duodenal papilla to perform treatment and the like in these procedures.

Incidentally, the side-view type endoscope 10 is sometimes referred to as a side-view endoscope. Similarly, the endoscope 10 suitable for diagnosis of the duodenum and pancreaticobiliary region is sometimes referred to as a duodenoscope.

According to the present embodiment, the pedestal 70 and the cover 52 are separate bodies, and thus, have simple shapes. Thus, it possible to produce the pedestal 70 and the cover 52 at low cost by, for example, injection-molding or the like.

Instead of the raising wire 24, a stretchable shape memory alloy (SMA) actuator may be used for the rotating portion. In this case, one end of the SMA actuator is fixed to the wire fixing portion 65, and the other end is fixed to the distal end portion 31. A heater is arranged around the SMA actuator. The heater is activated in conjunction with the movement of the raising operation lever 21.

When the heater is activated so that the SMA actuator shrinks, the lever 60 and the raising base 80 rotate. Any other linear actuator can be used for the rotating portion.

A rotary actuator such as a small motor may be used for the rotating portion. It is possible to rotate the lever 60 by arranging the small motor in the lever chamber 69 and connecting the motor shaft and the lever shaft 63.

When the actuator is used for the rotating portion, the raising base 80 can be operated using means which does not use a user's hand such as voice control.

The endoscope cap 50 may be provided in a state where the raising base 80 and the cover 52 or the pedestal 70 are provisionally fixed using a pressure-sensitive adhesive or the like with the lever connection portion 81 facing the side of the opening end portion 56. In this manner, it is possible to provide the endoscope cap 50 which can omit labor of confirming the orientation of the raising base 80 before attaching the endoscope cap 50 to the insertion portion 30 and be easily used.

The user may select and use the endoscope cap 50 having a specification corresponding to a procedure from a plurality of types of the endoscope caps 50 having different specifications. For example, the endoscope cap 50 provided with a stopper that narrowly limits a rotatable range of the raising base 80 may be provided. When using expensive and precise instruments, for example, an ultrasonic probe, a microscopic endoscope, and the like in combination, it is possible to prevent damage to the instruments due to excessive bending by narrowing the rotatable range.

When the recessed portion 84 has a shape conforming to an outer shape of the treatment tool distal end portion 41, the treatment tool 40 is less likely to shake in the lateral direction at the time of being raised, and tends to be easily operated. A plurality of types of the endoscope caps 50 having the raising bases 80 with different shapes of the recessed portions 84 may be provided. For example, when using the endoscope cap 50 provided with the recessed portion 84 having a shape that is easy to hold the slim treatment tool 40, it is easy to precisely operate the slim treatment tool 40 such as a guide wire.

In this manner, it is possible to provide the endoscope 10 which enables the user to select and use the endoscope cap 50 suitable for an application.

The endoscope 10 may be a so-called ultrasonic endoscope including an ultrasonic transducer at a distal end thereof. In this case, the endoscope cap 50 desirably has a hole through which the ultrasonic transducer is inserted, at a bottom thereof. The endoscope 10 may be an endoscope for a lower gastrointestinal tract. The endoscope 10 may be a so-called rigid scope provided with the rigid insertion portion 30. The endoscope 10 may be a so-called industrial endoscope used for an examination of an engine, piping, and the like.

The endoscope cap 50 may be reusable. In this case, the user visually inspects the endoscope cap 50 detached from the insertion portion 30, and performs processing such as cleaning for the reuse when there is no damage. Since the opening end portion 56 of the endoscope cap 50 is widely open, the processing such as cleaning can be easily performed as compared with the state of being attached to the insertion portion 30. Since the endoscope cap 50 is small, it is also easy to place the endoscope cap 50 in the sterilization pack, for example, and perform autoclave sterilization or the like.

The endoscope 10 may be provided with a fixing mechanism to fix the raising operation lever 21 at an arbitrary angle. The user can release fingers from the raising operation lever 21 after raising the treatment tool distal end portion 41 to a desired angle and focus on an operation of the bending knob 23 and the like.

Incidentally, positions of the first engagement portion 46 and the second engagement portion 72 are not limited to the above-described positions. For example, the engagement portion between the distal end portion 31 and the endoscope cap 50 may be provided at positions corresponding to the left and right sides of FIG. 4. The user can remove the endoscope cap 50 by pulling the endoscope cap 50 while pushing the operation unit side of the window portion 53 and the opposite side with the insertion portion 30 interposed therebetween with fingers.

Second Embodiment

The present embodiment relates to the endoscope 10 in which a shape of the first engagement portion 46 is different from that in the first embodiment. Descriptions regarding common parts with the first embodiment will be omitted.

Figure 24:
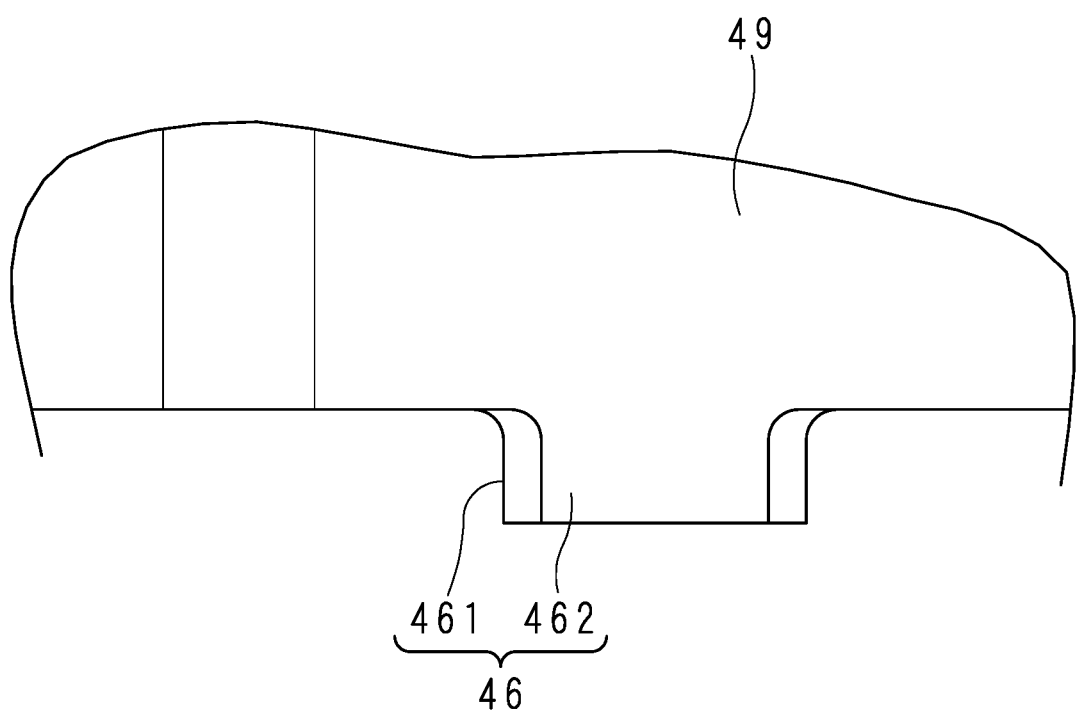
FIG. 24 is an enlarged view of a first engagement portion of a second embodiment as viewed from an opening end portion side.
Figure 25:
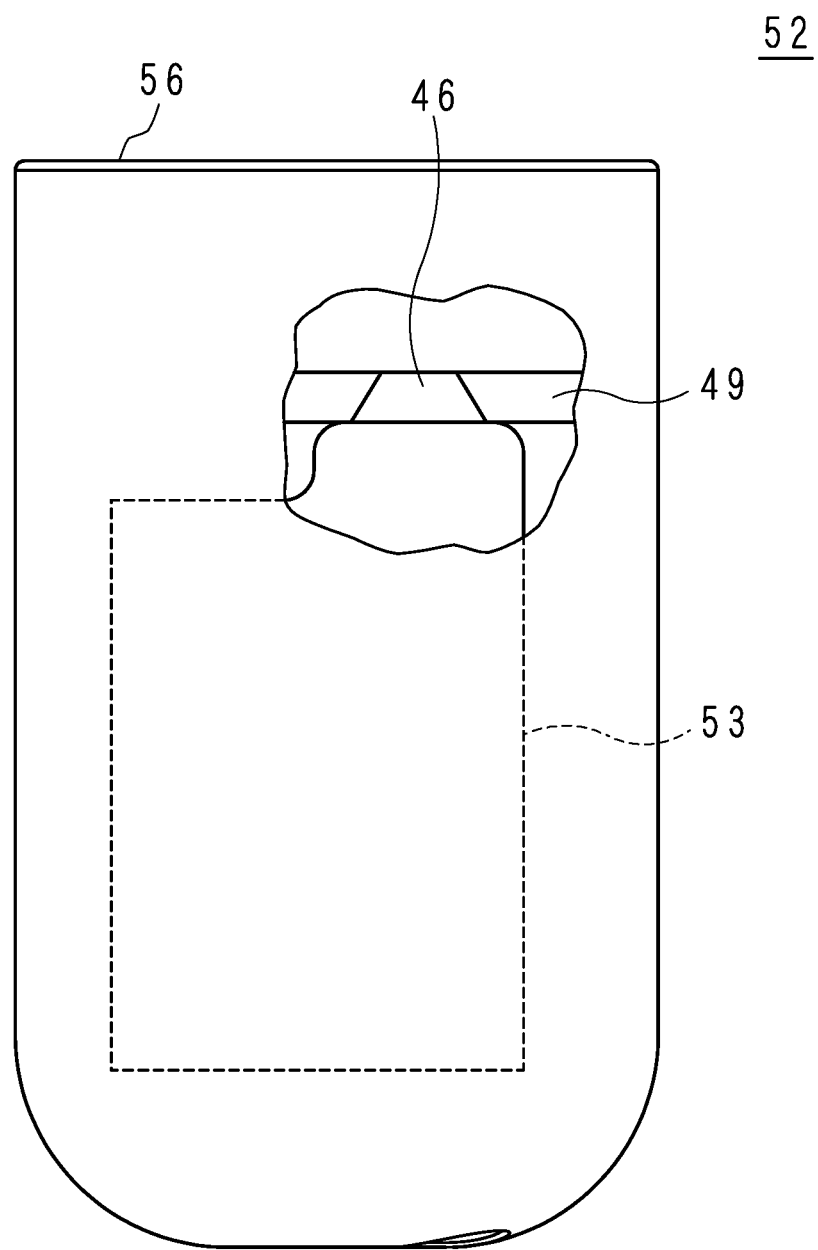
FIG. 25 is a back view of a cover of the second embodiment.

FIG. 24 is an enlarged view of the first engagement portion 46 of a second embodiment as viewed from the opening end portion 56 side. FIG. 25 is a back view of the cover 52 according to the second embodiment. In FIG. 25, a tubular portion is broken at a portion facing the first engagement portion 46 to illustrate the first engagement portion 46.

In the present embodiment, the first engagement portion 46 is a wedge shape whose dimension along a circumferential direction of the tubular portion becomes narrower from the distal end side of the endoscope 10 toward the operation unit side, and distal end is a flat surface. A lower surface of the first engagement portion 46 in FIG. 24 is a plane perpendicular to the paper surface of FIG. 24. According to the present embodiment, it is possible to provide the endoscope 10 which enables a user to easily attach the endoscope cap 50 to the insertion portion 30.

Incidentally, the first engagement portion 46 may have a wedge shape whose left and right surfaces in FIG. 25 intersect each other and which is pointed on the opening end portion 56 side.

Third Embodiment

The present embodiment relates to the endoscope 10 in which a shape of the first engagement portion 46 is different from those in the first and second embodiments. Descriptions regarding common parts with the second embodiment will be omitted.

Figure 26:
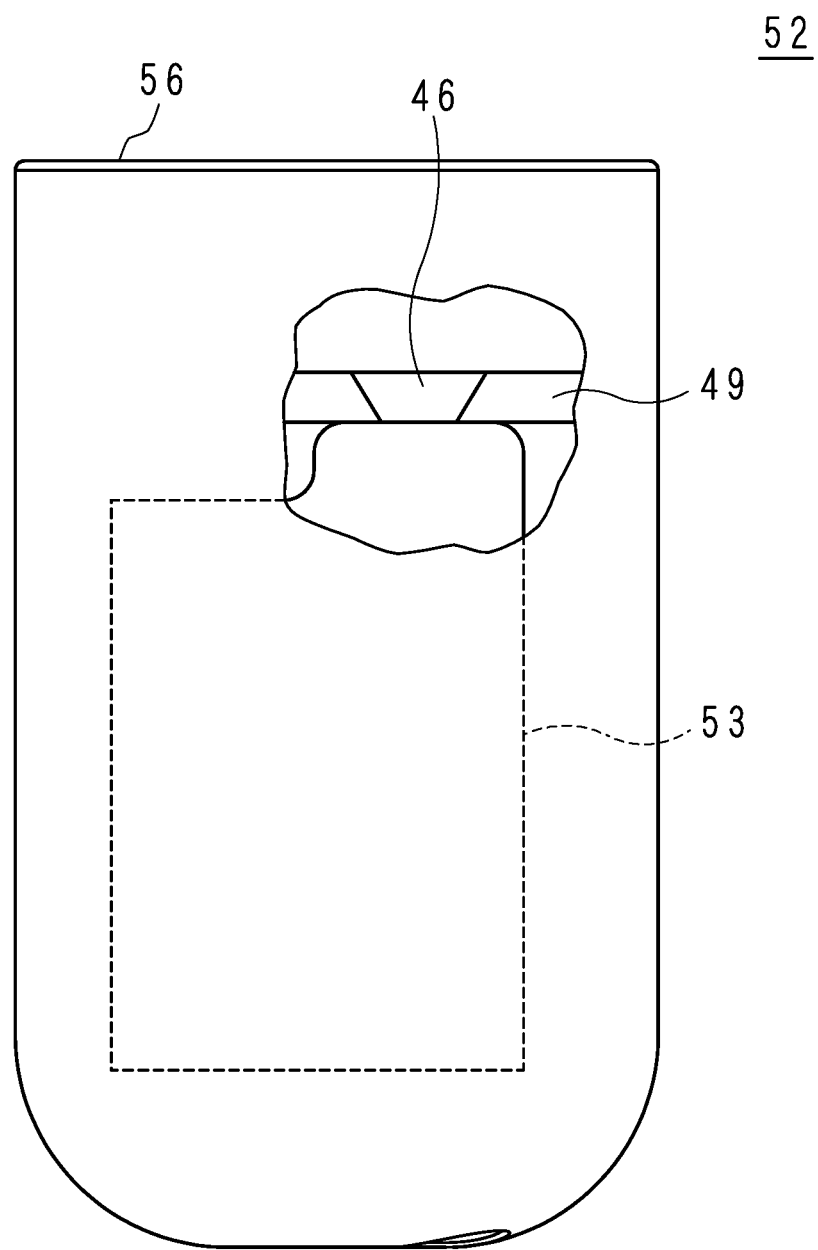
FIG. 26 is a back view of a cover of a third embodiment.

FIG. 26 is a back view of the cover 52 according to a third embodiment. Even in FIG. 26, a tubular portion is broken at a portion facing the first engagement portion 46 to illustrate the first engagement portion 46.

In the present embodiment, the first engagement portion 46 is a wedge shape whose dimension along a circumferential direction of the tubular portion becomes narrower from the operation unit side of the endoscope 10 toward the distal end side, and distal end is a flat surface. According to the present embodiment, it is possible to provide the endoscope 10 which enables a user to easily remove the endoscope cap 50 from the insertion portion 30 after use.

Fourth Embodiment

The present embodiment relates to the endoscope 10 in which a shape of the first engagement portion 46 is different from those in all the first to third embodiments. Descriptions regarding common parts with the first embodiment will be omitted.

Figure 27:
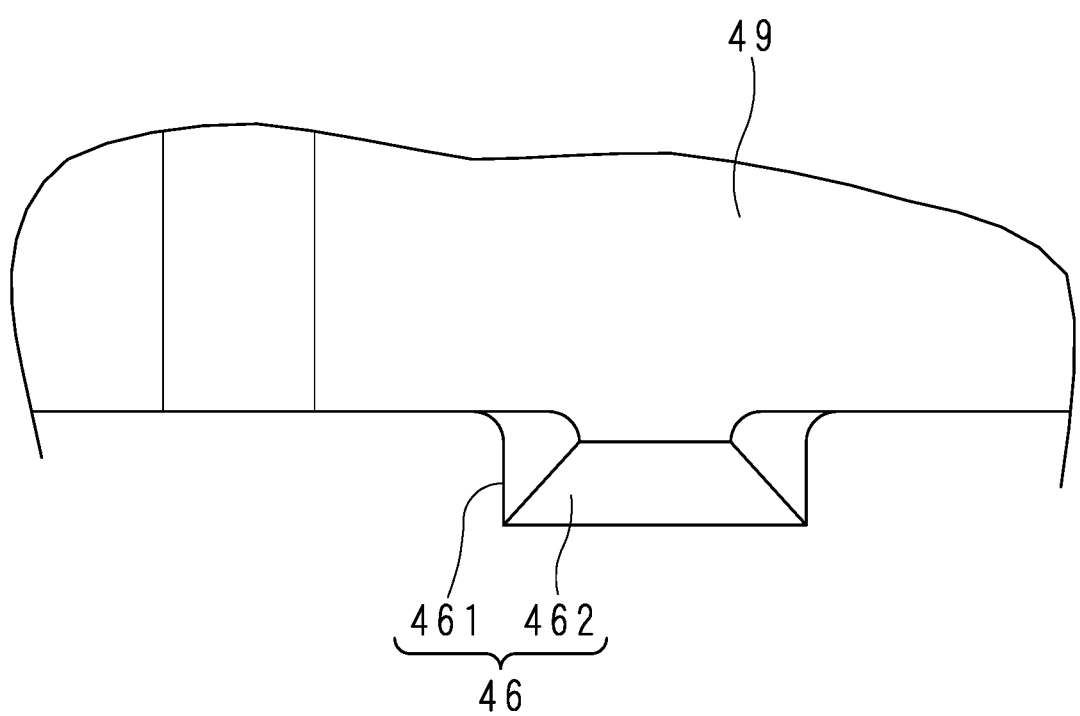
FIG. 27 is an enlarged view as viewed from an opening end portion side of a first engagement portion of a fourth embodiment.

FIG. 27 is an enlarged view of the first engagement portion 46 of a fourth embodiment as viewed from the opening end portion 56 side. The first engagement portion 46 has a first wedge surface 461 on a bottom side and a second wedge surface 462 on the opening end portion 56 side. The first wedge surface 461 is a plane which is continuous with a surface of the protruding portion 49 on the bottom side and extends along an edge of the window portion 53.

The second wedge surface 462 is a plane which is inclined with respect to an axial direction of the tubular portion having the inside on the bottom side and the outside on the opening end portion side. When the first engagement portion 46 is cut by a surface parallel to the axis of the tubular portion, the first wedge surface 461 and the second wedge surface 462 are tapered into a wedge shape.

The first engagement portion 46 is a wedge shape whose dimension along a circumferential direction of the tubular portion becomes narrower from the distal end side of the endoscope 10 toward the operation unit side. According to the present embodiment, it is possible to provide the endoscope 10 which enables a user to easily attach the endoscope cap 50 to the insertion portion 30.

Fifth Embodiment

The present embodiment relates to the endoscope 10 having the first engagement portion 46 that is easily removed from the distal end portion 31 when the cover 52 is deformed by pressing. Descriptions regarding common parts with the first embodiment will be omitted.

Figure 28:
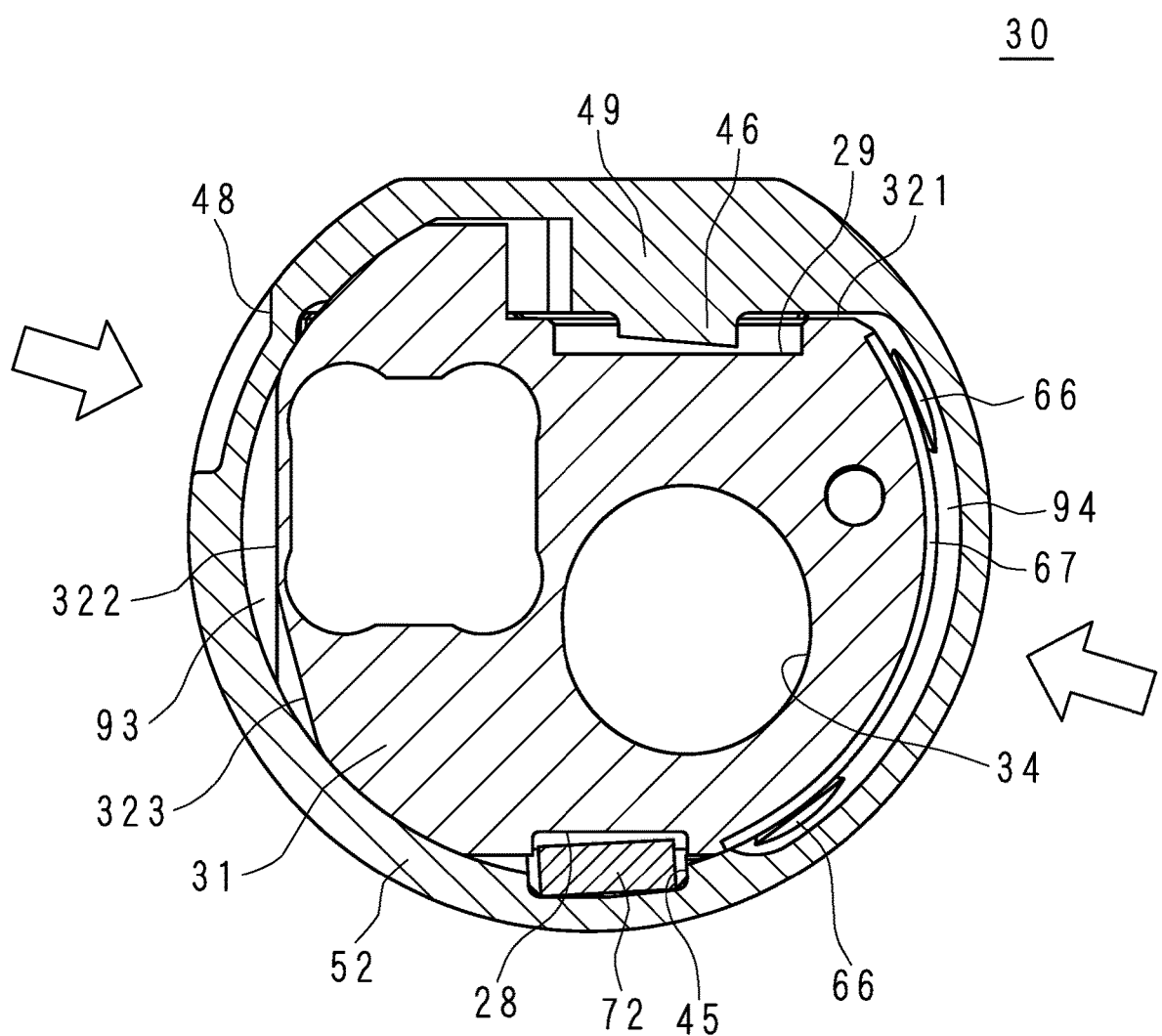
FIG. 28 is a cross-sectional view of an insertion portion of a fifth embodiment.

FIG. 28 is a cross-sectional view of the insertion portion 30 of a fifth embodiment. FIG. 28 is a cross-sectional view of the insertion portion 30 taken at the same position as line XXI-XXI in FIG. 4.

The first engagement portion 46 protrudes from a part of the protruding portion 49 and is engaged with the groove-shaped third engagement portion 29. In FIG. 28, a distal end of the first engagement portion 46 is inclined downward to the right with respect to an edge of the third engagement portion 29.

Figure 29:
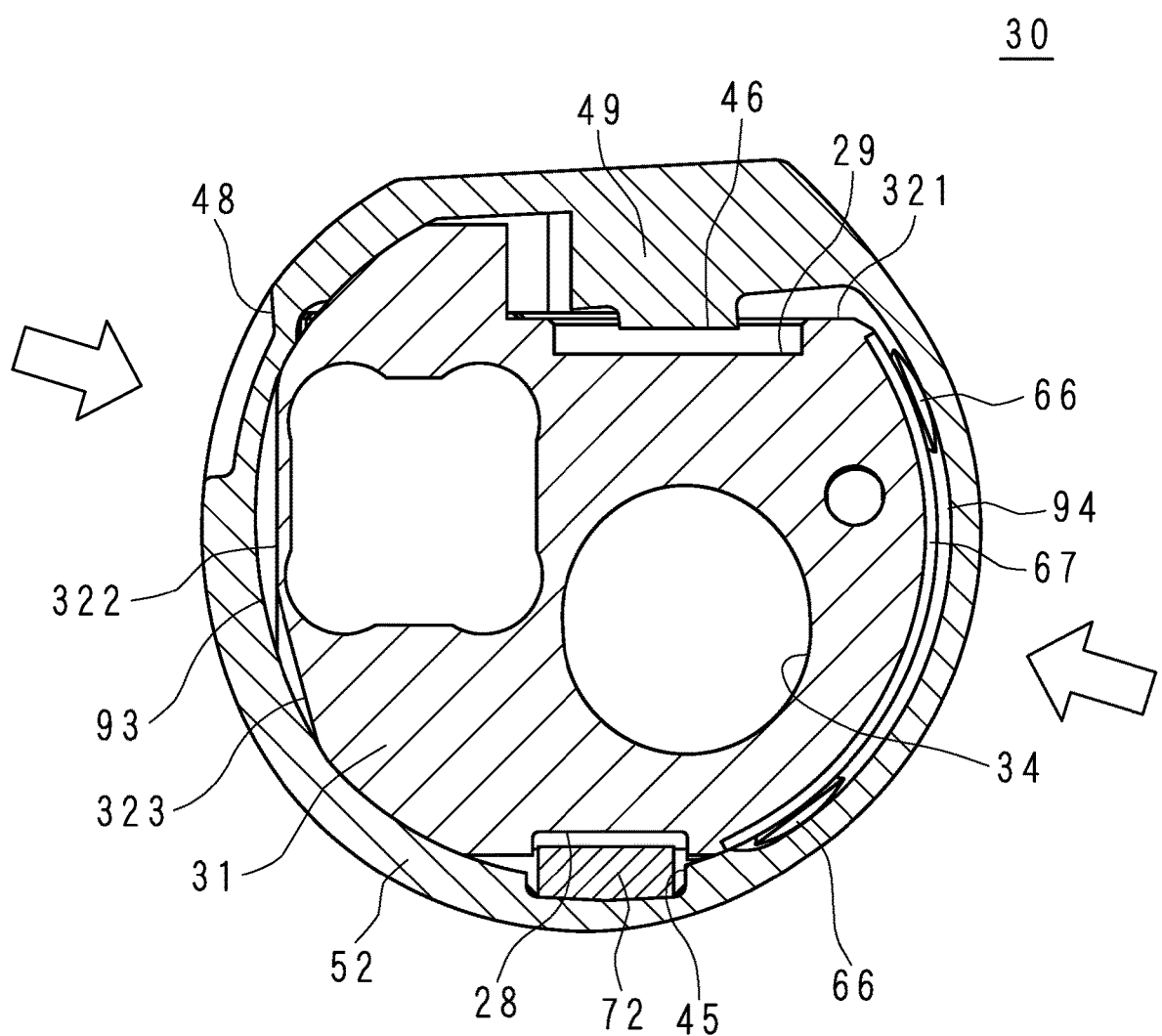
FIG. 29 is a cross-sectional view of an insertion portion deformed by pressing a cover of the fifth embodiment.

A user presses two places of the concave portion 48 and the opposite side thereof with fingers as indicated by the white arrows in FIG. 28. FIG. 29 is a cross-sectional view of the insertion portion 30 deformed by pressing the cover 52 of the fifth embodiment. FIG. 29 illustrates the same cross section as FIG. 28. The cover 52 is deformed mainly at a thin portion, and each of the first engagement portion 46 and the second engagement portion 72 moves outward. Due to the deformation of the cover 52, a lower side of the first engagement portion 46 becomes parallel to the edge of the third engagement portion 29.

According to the present embodiment, it is possible to provide the endoscope 10 in which the engagement between the first engagement portion 46 and the third engagement portion 29 can be released with a minimum deformation amount thus required and the endoscope cap 50 can be removed from the distal end of the insertion portion 30

Incidentally, a shape of the lower side of the first engagement portion 46 can be appropriately set according to the deformation of the entire cover 52 when pressed.

Sixth Embodiment

The present embodiment relates to the endoscope 10 including the raising base connection portion 61 whose distal end side is narrower than the operation unit side along the insertion direction. Descriptions regarding common parts with the first embodiment will be omitted.

Figure 30:
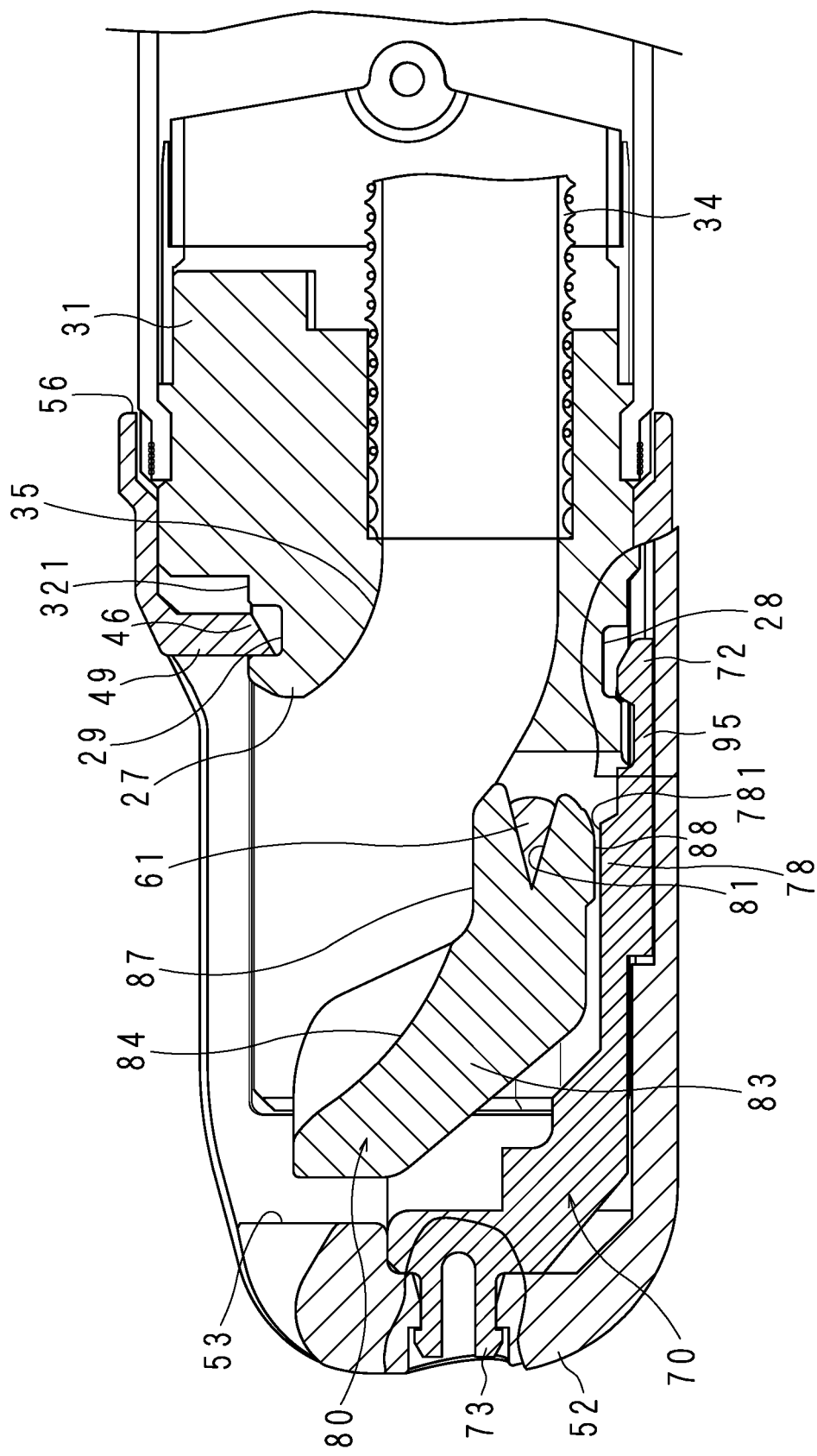
FIG. 30 is a cross-sectional view of an insertion portion of a sixth embodiment.

FIG. 30 is a cross-sectional view of the insertion portion 30 according to a sixth embodiment. FIG. 30 is a cross-sectional view taken along a longitudinal direction of the insertion portion 30 at a position of the raising base connection portion 61 similarly to FIG. 20. As illustrated in FIG. 30, the raising base connection portion 61 has a wedge shape that is thinner on the distal end side than the operation unit side. In addition, the lever connection portion 81 has a V-shape that is expanded on the operation unit side.

According to the present embodiment, an inlet of the lever connection portion 81 is widened, and a distal end of the raising base connection portion 61 is thin, and thus, the distal end of the raising base connection portion 61 easily enters the lever connection portion 81 even from a state where the raising base 80 is somewhat rotated. As a user pushes the endoscope cap 50 to a distal end of the insertion portion 30, the raising base connection portion 61 enters the back of the lever connection portion 81, and the raising base 80 is guided in a correct direction.

The raising base connection portion 61 and the lever connection portion 81 can adopt arbitrary shapes capable of being engaged with each other.

Seventh Embodiment

The present embodiment relates to the endoscope 10 in which the first engagement portion 46 has a plate shape. Descriptions regarding common parts with the first embodiment will be omitted.

Figure 31:
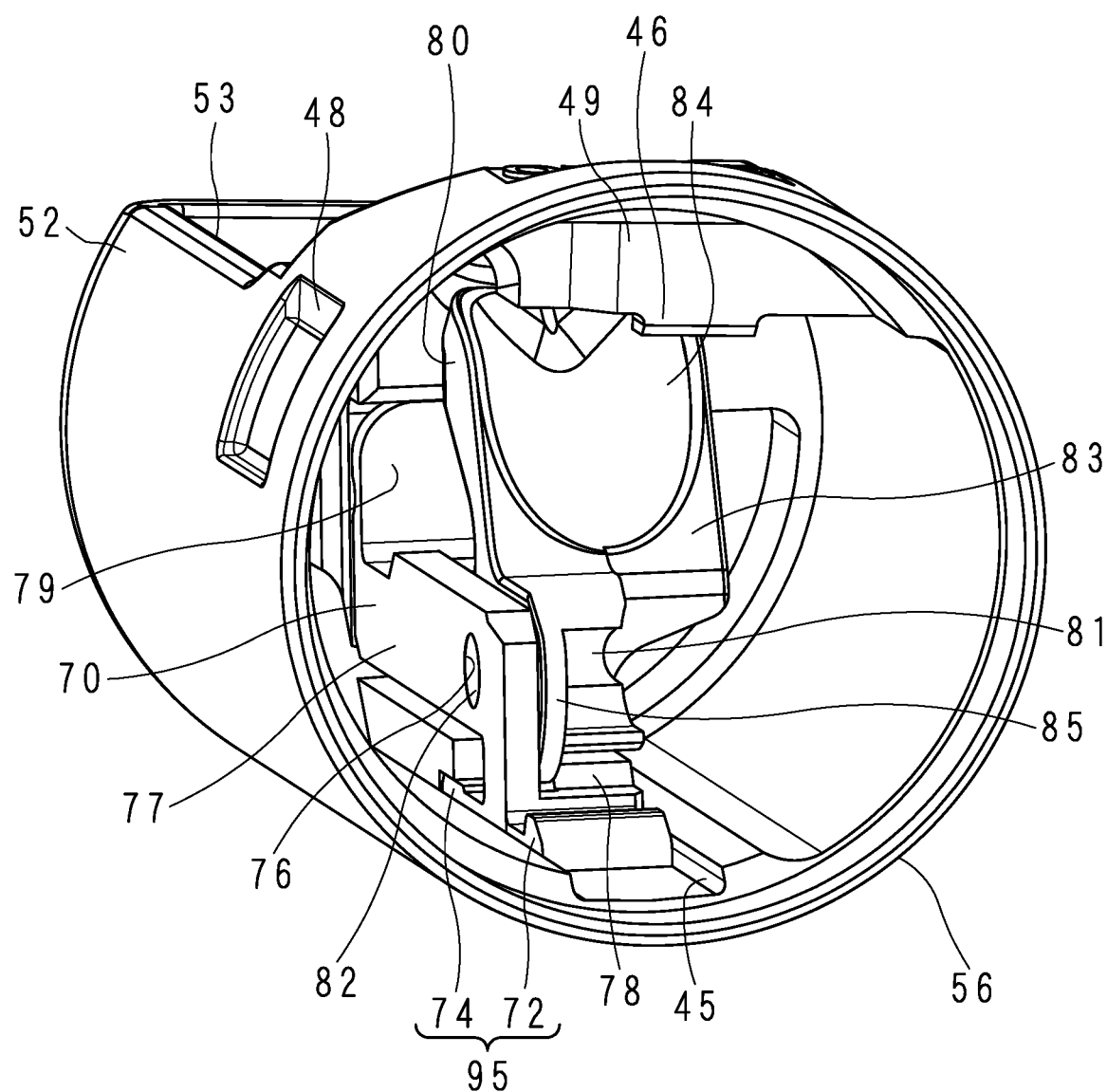
FIG. 31 is a perspective view of an endoscope cap of a seventh embodiment as viewed from an attachment side with respect to the endoscope.

FIG. 31 is a perspective view of the endoscope cap 50 according to a seventh embodiment viewed from the attachment side with respect to the endoscope 10. The cover 52 has a plate-shaped protruding portion 49 that protrudes inward along an edge on the opening end portion 56 side of the window portion 53. The plate-shaped first engagement portion 46 further protrudes from a part of a distal end of the protruding portion 49. The protruding portion 49 and the first engagement portion 46 are flush along an edge of the window portion 53.

Figure 32:
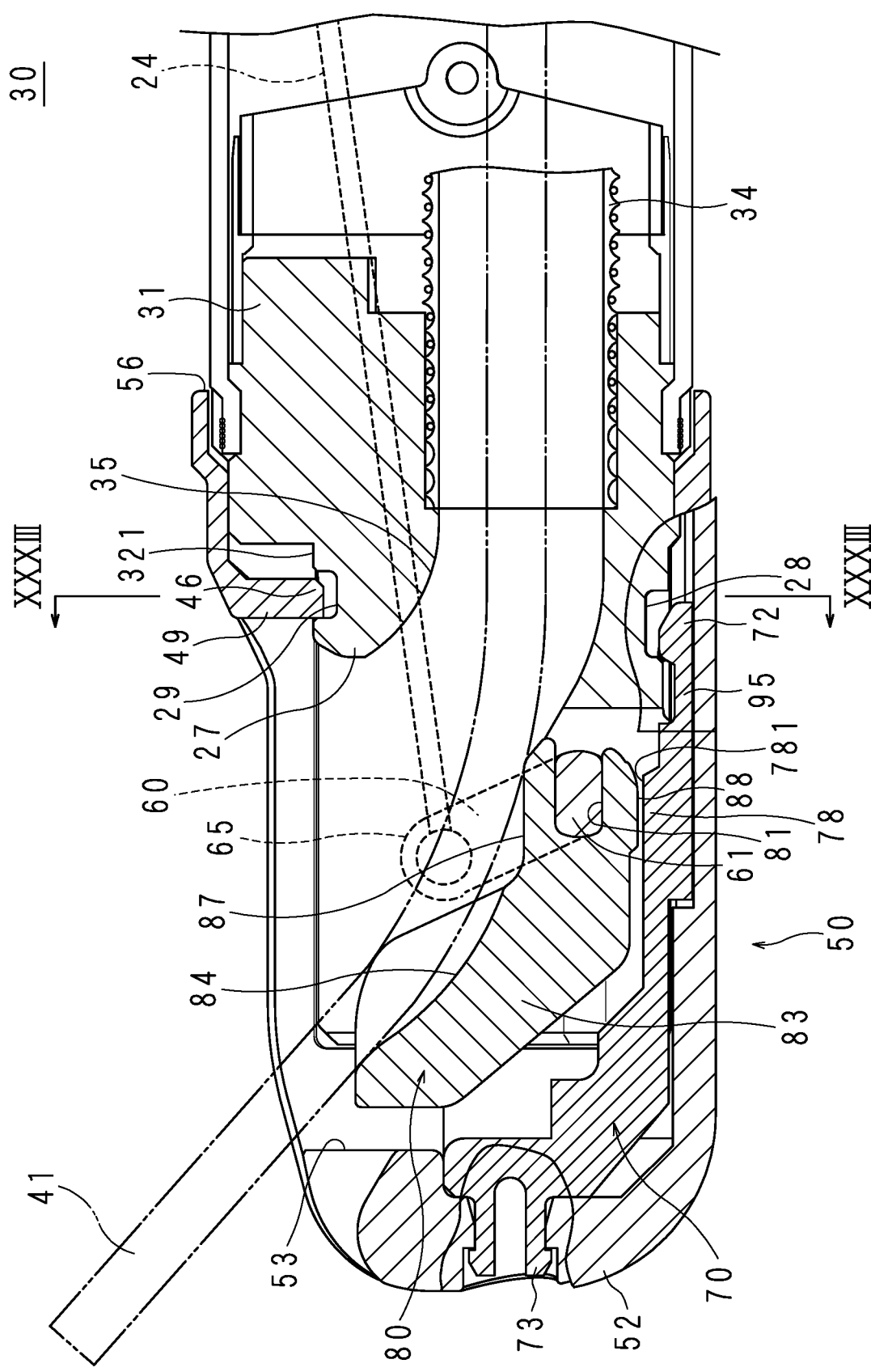
FIG. 32 is a cross-sectional view of an insertion portion of the seventh embodiment.
Figure 33:
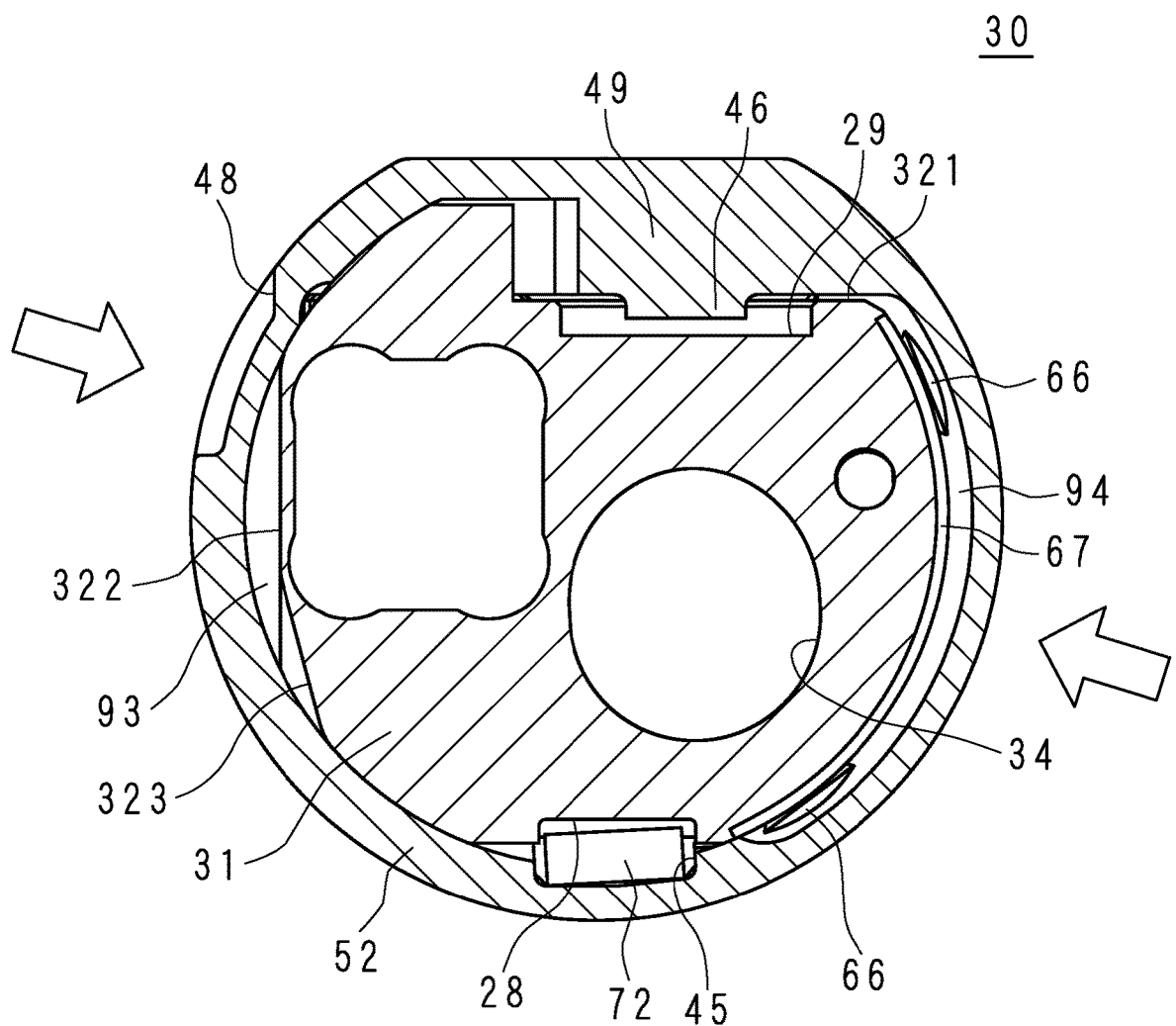
FIG. 33 is a cross-sectional view of the insertion portion taken along line XXXIII-XXXIII of FIG. 32.
Figure 34:
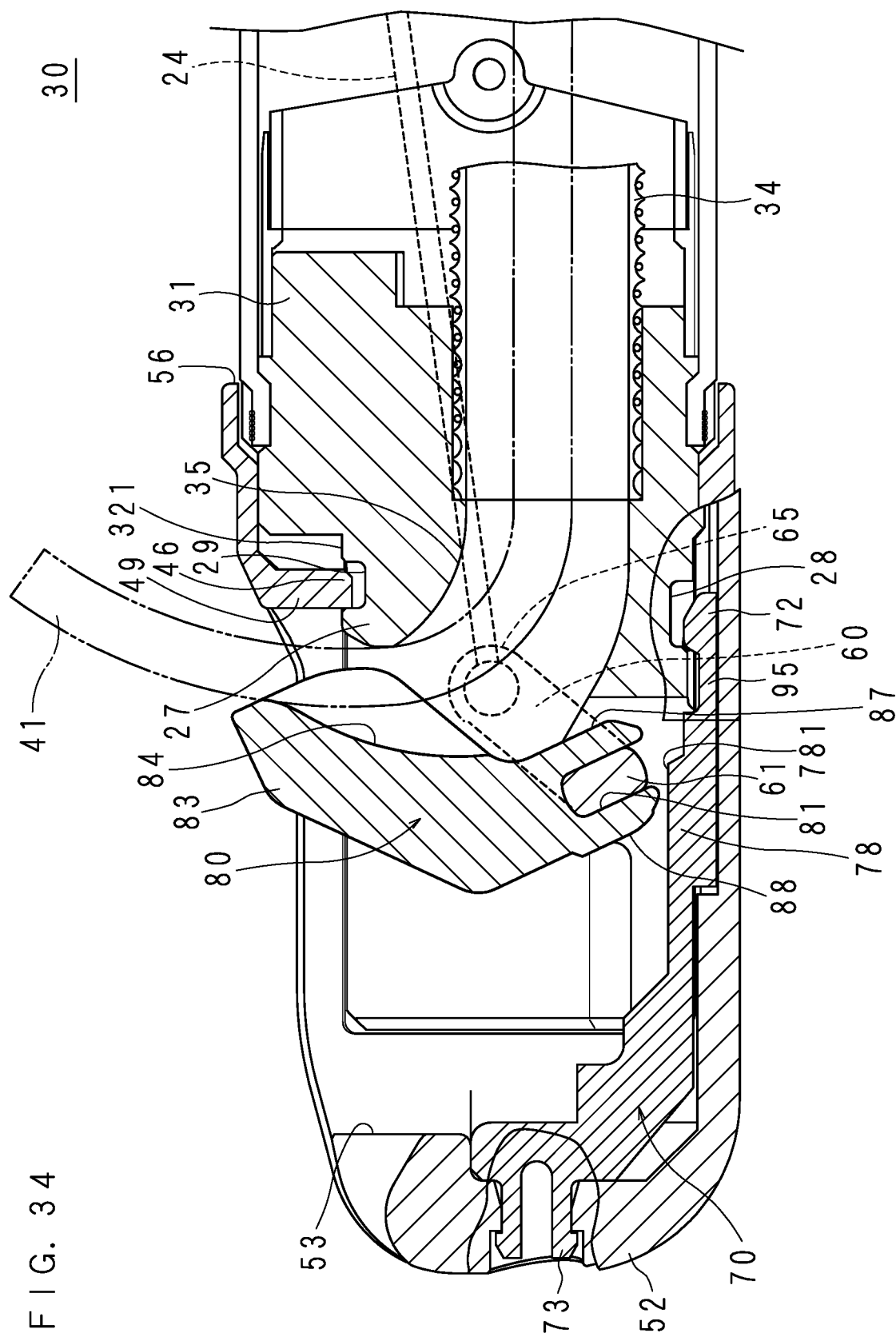
FIG. 34 is a cross-sectional view of the insertion portion with a raising base of the seventh embodiment raised.

FIG. 32 is a cross-sectional view of an insertion portion of the seventh embodiment. FIG. 32 is a cross section cutting the insertion portion 30 in the longitudinal direction at a position of the raising base connection portion 61 similarly to FIG. 20. FIG. 33 is a cross-sectional view of the insertion portion taken along line XXXIII-XXXIII of FIG. 32. A XXXIII-XXXIII cross section is a cross section that passes through an edge of the fourth engagement portion 28 on the operation unit side and the third engagement portion 29 and is perpendicular to the longitudinal direction of the insertion portion 30. A configuration in which the endoscope cap 50 is attached to and detached from the distal end of the insertion portion 30 will be described with reference to FIGS. 19 and 20.

Since the first engagement portion 46 has the plate shape, the first engagement portion 46 is hardly deformed even when an external force is applied to the endoscope cap 50 during use of the endoscope 10 or the like. Thus, the endoscope cap 50 is hardly removed from the endoscope 10 when a user does not intend to remove the endoscope cap 50.

A user presses two places of the concave portion 48 and the opposite side thereof with fingers as indicated by the white arrows in FIG. 33. Since the first cavity portion 93 and the second cavity portion 94 exist on the back side of portions to be pressed, the cover 52 is deformed into a substantially elliptical shape with a pressing direction as a short axis and a direction orthogonal to the pressing direction as a long axis.

The first engagement portion 46 and the second engagement portion 72 described above are provided in the vicinity of a portion which becomes the long axis of the deformed cover 52. As the endoscope cap 50 is deformed, each of the first engagement portion 46 and the second engagement portion 72 moves outward, and the engagement with each of the third engagement portion 29 and the fourth engagement portion 28 is released. Incidentally, the concave portion 48 is thinner than the other portion in the circumferential direction of the cover 52 as described above, and is a flexible portion that is easily flexed by being pushed with the finger or the like. Thus, the user can easily deform the endoscope cap 50.

As the user pulls the endoscope cap 50 to the distal end side while pressing the endoscope cap 50, the engagement between the lever connection portion 81 and the raising base connection portion 61 is also released, and it is possible to remove the endoscope cap 50 from the distal end of the insertion portion 30. As illustrated in FIG. 4, the concave portion 48 has a side orthogonal to the insertion direction. Thus, the finger of the user is caught by the edge of the concave portion 48, and the endoscope cap 50 can be easily detached.

Incidentally, the user can attach the endoscope cap 50 to the insertion portion 30 by confirming that a direction of the lever connection portion 81 and a direction of the raising base connection portion 61 are aligned, and then, pushing the endoscope cap 50 into the distal end of the insertion portion 30. As illustrated in FIG. 32, an end portion of the first engagement portion 46 on the opening end portion 56 side is chamfered, and thus, the first engagement portion 46 is hardly caught by the distal end portion 31 so that the attachment is easy.

Eighth Embodiment

The present embodiment relates to the endoscope 10 in which the third engagement portion 29 is a protrusion. Descriptions regarding common parts with the seventh embodiment will be omitted.

Figure 35:
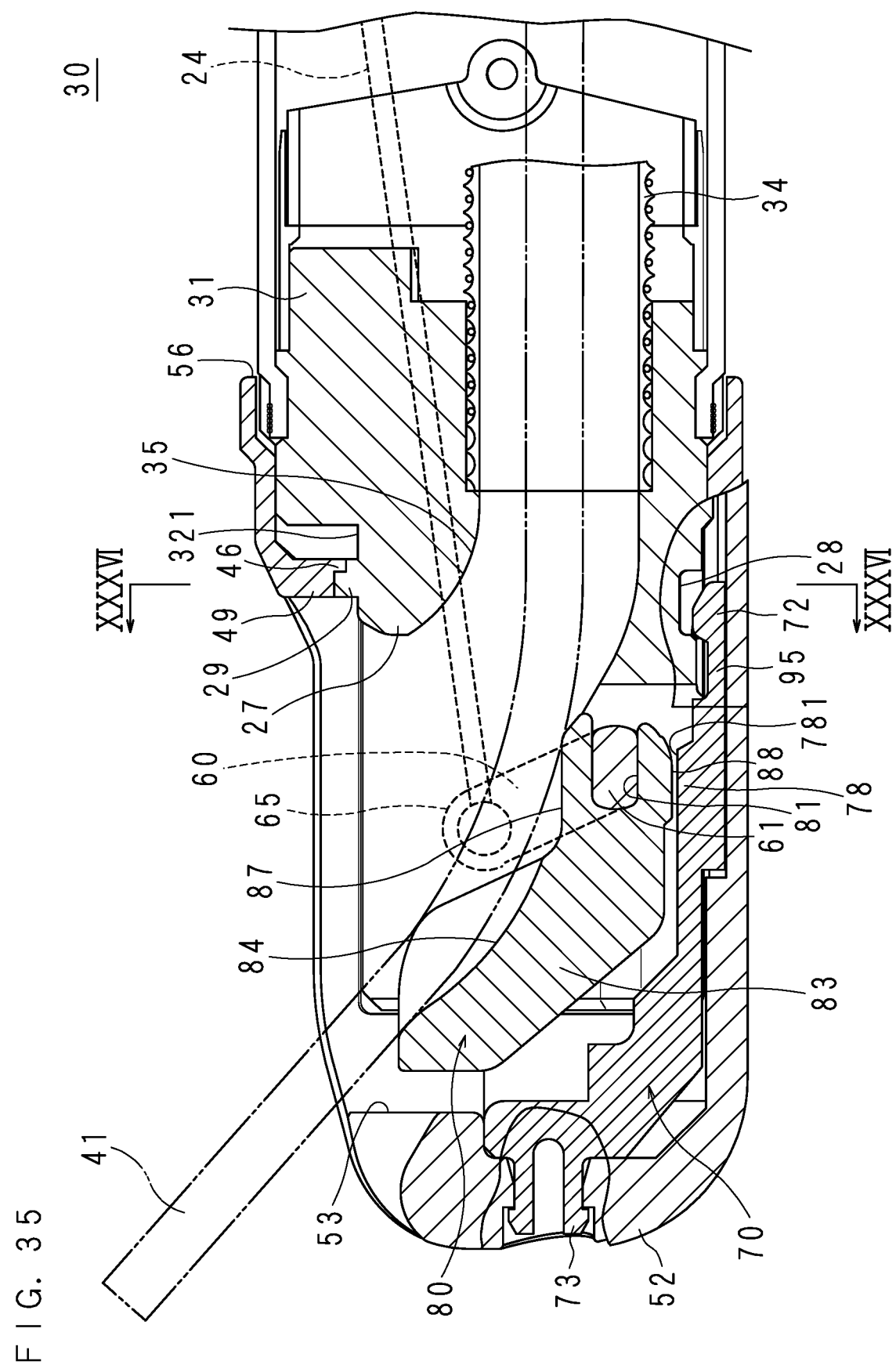
FIG. 35 is a cross-sectional view of an insertion portion of an eighth embodiment.
Figure 36:
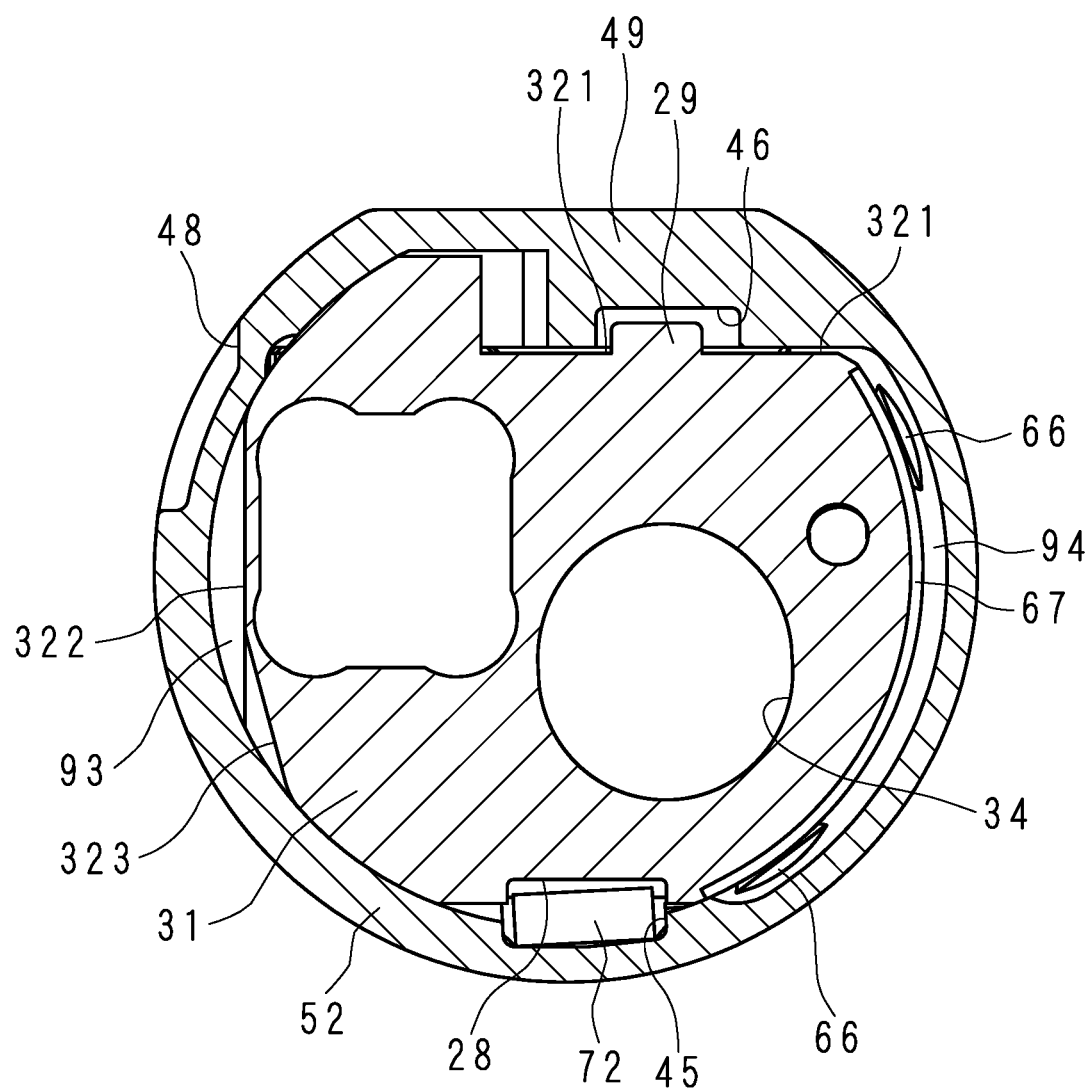
FIG. 36 is a cross-sectional view of the insertion portion taken along line XXXVI-XXXVI of FIG. 35.

FIG. 35 is a cross-sectional view of the insertion portion 30 according to an eighth embodiment. FIG. 35 is a cross section cutting the insertion portion 30 in the longitudinal direction at a position of the raising base connection portion 61 similarly to FIG. 20. FIG. 36 is a cross-sectional view of the insertion portion 30 taken along line XXXVI-XXXVI of FIG. 35.

The third engagement portion 29 is the protrusion protruding from the first flat surface portion 321. The first engagement portion 46 is a recess provided on the window portion 53 side of the protruding portion 49. The first engagement portion 46 is engaged with the third engagement portion 29 of the distal end portion 31. In addition, the second engagement portion 72 is engaged with the fourth engagement portion 28 similarly to the first embodiment. The endoscope cap 50 is fixed to a distal end of the insertion portion 30 as the endoscope cap 50 is engaged with the distal end portion 31 at two opposing places on an inner surface.

The first engagement portion 46 and the third engagement portion 29 can adopt arbitrary shapes capable of being engaged with each other. The second engagement portion 72 and the fourth engagement portion 28 can also adopt arbitrary shapes capable of being engaged with each other.

Ninth Embodiment

The present embodiment relates to the endoscope 10 including the raising base connection portion 61 whose distal end side is narrower than the operation unit side along the insertion direction. Descriptions regarding common parts with the seventh embodiment will be omitted.

Figure 37:
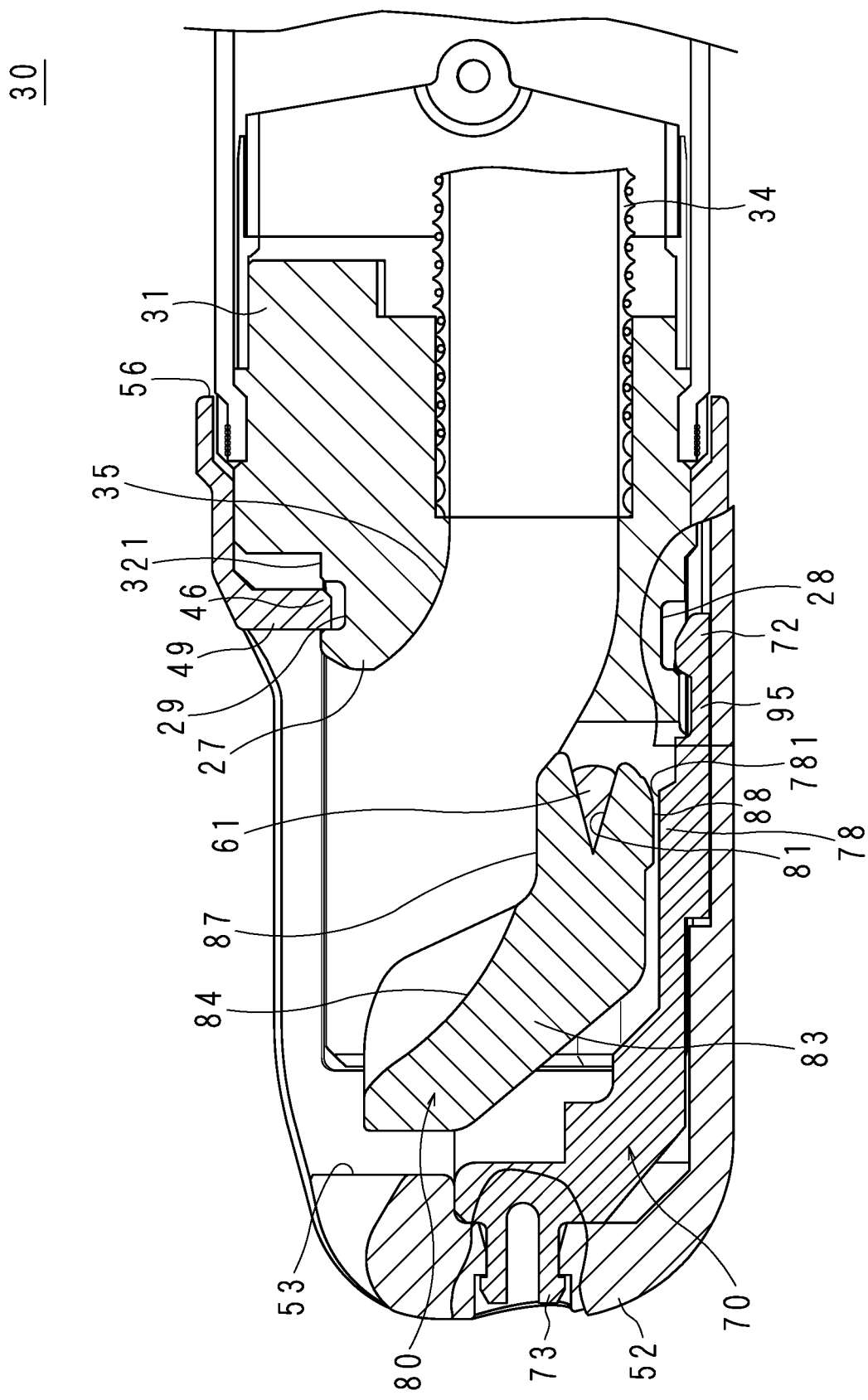
FIG. 37 is a cross-sectional view of an insertion portion of a ninth embodiment.

FIG. 37 is a cross-sectional view of the insertion portion 30 according to a ninth embodiment. FIG. 37 is a cross section cutting the insertion portion 30 in the longitudinal direction at a position of the raising base connection portion 61 similarly to FIG. 20. As illustrated in FIG. 37, the raising base connection portion 61 has a wedge shape that is thinner on the distal end side than the operation unit side. In addition, the lever connection portion 81 has a V-shape that is expanded on the operation unit side.

According to the present embodiment, an inlet of the lever connection portion 81 is widened, and a distal end of the raising base connection portion 61 is thin, and thus, it is possible to provide the endoscope 10 in which it is easy to engage the lever connection portion 81 with the raising base connection portion 61 even from a state where the raising base 80 is somewhat rotated.

The raising base connection portion 61 and the lever connection portion 81 can adopt arbitrary shapes capable of being engaged with each other.

Tenth Embodiment

The present embodiment relates to the endoscope 10 having indicators in vicinity of a distal end of the insertion portion 30 and on the endoscope cap 50. Descriptions regarding common parts with the first embodiment will be omitted.

Figure 38:
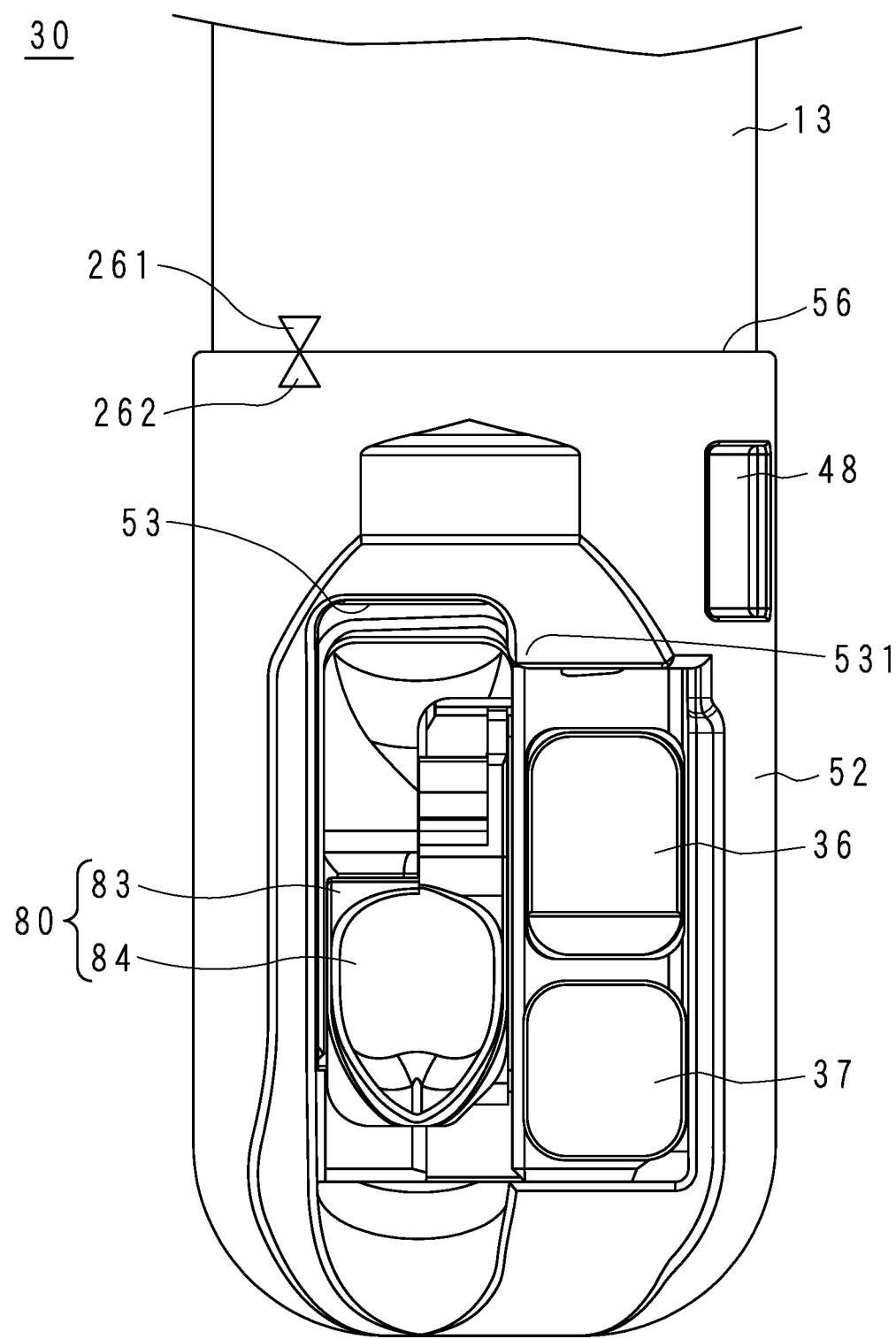
FIG. 38 is a front view of a distal end of an insertion portion of a tenth embodiment.

FIG. 38 is a front view of the distal end of the insertion portion 30 according to a tenth embodiment. The insertion portion 30 has the first indicator 261. The first indicator 261 is formed on a surface of a soft tube covering a surface of the bending portion 13 by printing, laser processing, or the like.

The cover 52 has a second indicator 262 in the vicinity of the opening end portion 56. The second indicator 262 is a recess or a protrusion integrally formed on a surface of the cover 52. The second indicator 262 may be formed on the surface of the cover 52 by printing, laser processing, or the like. The second indicator 262 may be formed at the opening end portion 56 or in the vicinity thereof by cutting or the like.

According to the present embodiment, the user using the endoscope 10 pushes the endoscope cap 50 into the distal end of the insertion portion 30 in the state where the first indicator 261 and the second indicator 262 are aligned in the circumferential direction, and thus, can quickly attach the endoscope cap 50 in the correct orientation. Further, the user visually confirms that the first indicator 261 and the second indicator 262 are in close contact with each other as illustrated in FIG. 38, and thus, can confirm that the endoscope cap 50 has been pushed into a predetermined position.

Shapes, sizes, and the like of the first indicator 261 and the second indicator 262 are arbitrary.

Eleventh Embodiment

The present embodiment relates to the endoscope 10 using a shape of the endoscope cap 50 itself instead of the second indicator 262. Descriptions regarding common parts with the tenth embodiment will be omitted.

Figure 39:
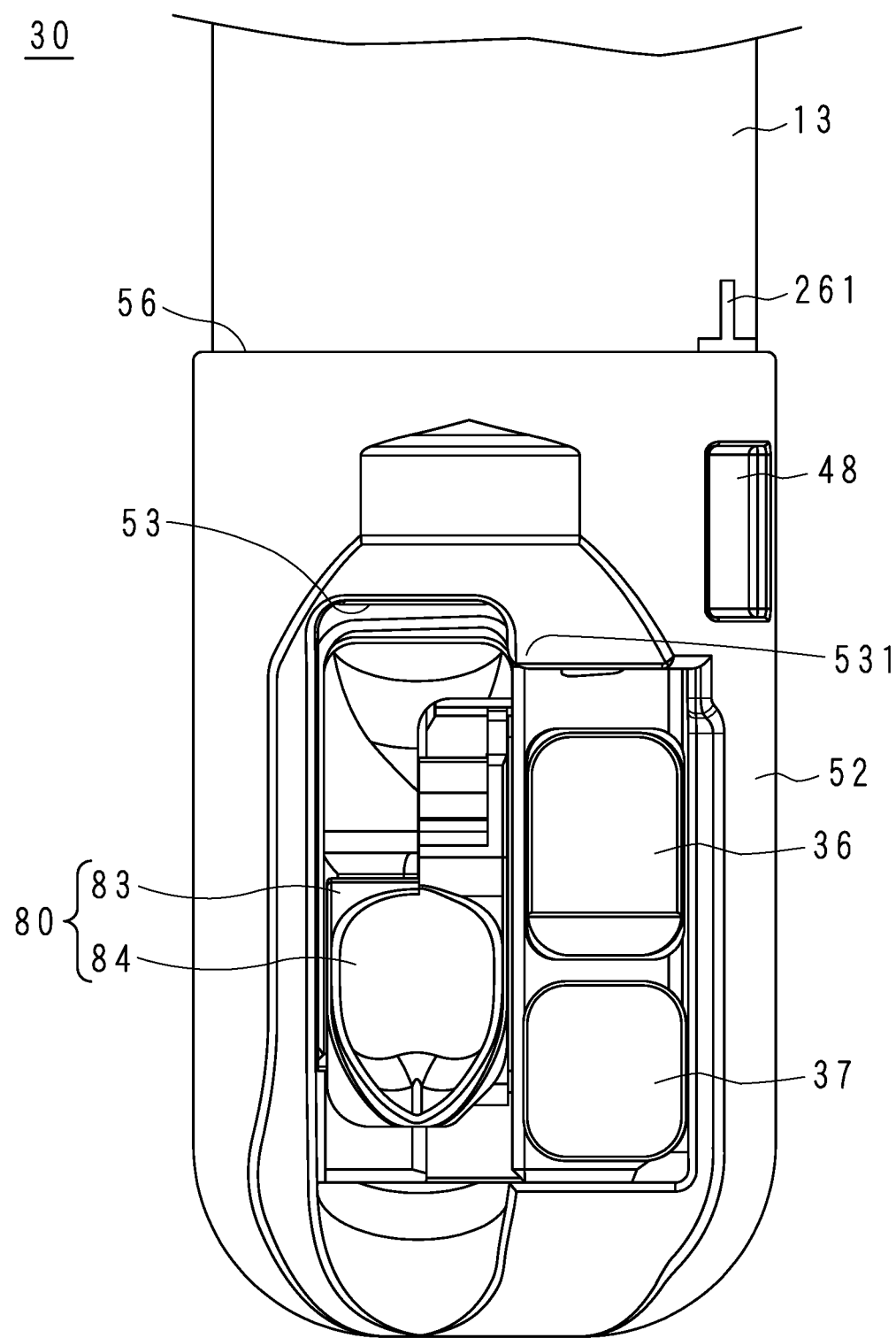
FIG. 39 is a front view of a distal end of an insertion portion of an eleventh embodiment.

FIG. 39 is a front view of the distal end of the insertion portion 30 according to an eleventh embodiment. The insertion portion 30 has the first indicator 261.

In the present embodiment, the concave portion 48 provided on a surface of the cover 52 is used instead of the second indicator 262 of the tenth embodiment. That is, the concave portion 48 serves the function of the second indicator 262.

According to the present embodiment, the user using the endoscope 10 pushes the endoscope cap 50 into the distal end of the insertion portion 30 in the state where the first indicator 261 and the concave portion 48 are aligned in the circumferential direction, and thus, can quickly attach the endoscope cap 50 in the correct orientation. Further, the user visually confirms that the opening end portion 56 and the first indicator 261 are in close contact with each other as illustrated in FIG. 39, and thus, can confirm that the endoscope cap 50 has been pushed into a predetermined position.

A shape, a size, and the like of the first indicator 261 are arbitrary. An arbitrary part of the cover 52, such as an edge of the window portion 53, can be used instead of the second indicator 262.

Twelfth Embodiment

The present embodiment relates to a procedure of packaging and sterilizing the endoscope cap 50. Descriptions regarding common parts with the first embodiment will be omitted.

Figure 40:
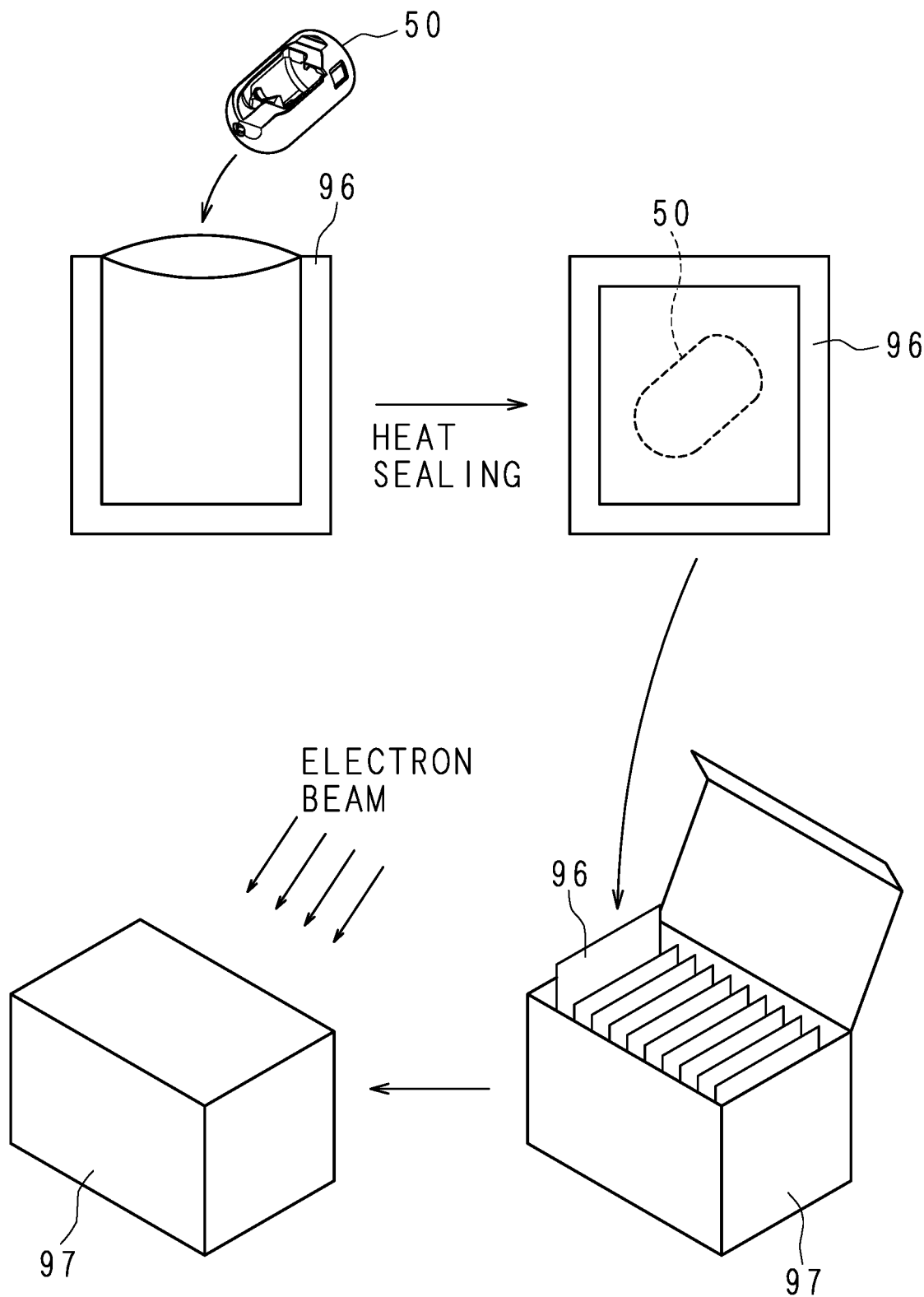
FIG. 40 is an explanatory view for describing a process of packaging and sterilizing a cap of a twelfth embodiment.

FIG. 40 is an explanatory view for describing a process of packaging and sterilizing the cap of a twelfth embodiment. The endoscope cap 50 is desirably produced in a clean room or in a hygienic room conforming to the clean room. This is because a sterilization effect in a subsequent sterilization process is lowered when a foreign matter including protein or lipid adheres.

The endoscope cap 50 may be cleaned by cleaning with a detergent and hot water or the like to be set to a clean state after completion of assembling. In this case, the endoscope cap 50 is subjected to sufficient dryings before proceeding to a subsequent process such that no water droplet or the like remain.

The endoscope cap 50 is placed one by one in an individual packaging member 96 obtained by forming a sheet for electron beam sterilization in a bag shape. An opening portion of the individual packaging member 96 is sealed by heat sealing. The individual packaging member 96 in which the endoscope cap 50 is enclosed is placed in a packaging box 97.

The packaging box 97 closed with a lid after placing a predetermined number of the individual packaging members 96 containing endoscope caps 50 therein is sterilized by electron beam sterilization. The electron beam sterilization can be carried out at room temperature in several tens of minutes, and thus, is suitable for sterilization of the endoscope cap 50 made of resin parts manufactured by injection-molding. The endoscope cap 50 is supplied to the user in the unit of the packaging box 97.

The user takes out the individual packaging member 96 in which the endoscope cap 50 is enclosed from the packaging box 97. The user takes out the endoscope cap 50 from the individual packaging member 96 and attaches the endoscope cap 50 to the distal end of the insertion portion 30. Since the endoscope caps 50 are enclosed in the individual packaging members 96 one by one, the user can keep the endoscope cap 50 in the clean state until the time immediately before use.

Instead of the electron beam sterilization, gamma ray sterilization may be used. Arbitrary radiation sterilization other than electron beam sterilization and gamma ray sterilization may be used. The gamma ray sterilization can be carried out at room temperature in several hours. Although the gamma ray sterilization takes more time than the electron beam sterilization, the permeability of gamma rays is larger than that of electron beams, and thus, a large number of the packaging boxes 97 can be collectively sterilized, for example, after being placed in a shipping box made of cardboard. It is possible to reduce the labor of taking the packaging box and placing the packaging box in a sterilization device by performing the sterilization for each shipping box.

The individual packaging member 96 may be formed for gas sterilization or high-pressure steam sterilization. The endoscope cap 50 enclosed in the individual packaging member 96 may be supplied to the user in an unsterilized state. The gas sterilization and high-pressure steam sterilization can be carried out in many medical institutions. The user can sterilize the endoscope cap 50 using the gas sterilization or high-pressure steam sterilization within a medical institution on a day before a day of use, on the day of use, or the like.

For example, as an indicator illustrating a sterilized state is enclosed together with the endoscope cap 50 in the individual packaging member 96, the user can confirm that the sterilization process has been completed and use the endoscope cap 50 with comfort.

In any case, the endoscope cap 50 is produced using a material suitable for each sterilizing means. For example, the endoscope cap 50 is produced using a resin material or the like of a radiation resistance grade in the case of using the electron beam sterilization or gamma ray sterilization. When the gas sterilization is used, the endoscope cap 50 is produced using a resin material or the like of a grade that is durable against a sterilizing gas. When the high-pressure steam sterilization is performed, the endoscope cap 50 is produced using a resin material or the like of a heat resistance grade.

Technical features (constitutional requirements) described in the respective embodiments can be combined with each other, and new technical features can be formed with the combination.

The embodiments disclosed herein are exemplary in all respects, and it should be considered that the embodiments are not restrictive. The scope of the present disclosure is defined not by the above-described meaning but by claims, and intends to include all modifications within meaning and a scope equal to claims.

Regarding the embodiments including the first to twelfth embodiments, the following appendixes are additionally disclosed.

(Appendix 1)

An endoscope cap attachable and detachable to and from an endoscope including a lever rotatably provided at a distal end of an insertion portion of the endoscope and a rotating portion which rotates the lever, the endoscope cap including:

a bottomed tubular cover which has an opening end portion and is attachable and detachable to and from the distal end of the insertion portion of the endoscope through the opening end portion;

a wedge-shaped first engagement portion which protrudes inward from an inner surface of a tubular portion of the cover; and a raising base which has a lever connection portion connected to the lever and is provided rotatably inside the cover.

(Appendix 2)

The endoscope cap according to Appendix 1, in which the first engagement portion is a wedge shape having a first wedge surface arranged on a side of a bottom of the cover and a second wedge surface arranged on a side of the opening end portion, and the second wedge surface is inclined with respect to a longitudinal direction of the tubular portion of the cover.

(Appendix 3)

The endoscope cap according to Appendix 2, in which the first wedge surface is a flat surface parallel to the bottom of the cover.

(Appendix 4)

The endoscope cap according to any one of Appendixes 1 to 3, in which the cover has a window portion which is open to the tubular portion, and the first wedge surface is a surface continuous with an edge of the window portion on the opening end portion side.

(Appendix 5)

The endoscope cap according to any one of Appendixes 1 to 4, in which the first engagement portion is a wedge shape that becomes thinner from the bottom side of the cover toward the opening end portion side.

(Appendix 6)

The endoscope cap according to any one of Appendixes 1 to 5, further including a second engagement portion opposing the first engagement portion.

(Appendix 7)

An endoscope including:

a rotatable raising base connection portion exposed on a surface of a distal end of an insertion portion;

an endoscope cap including a bottomed tubular cover which has an opening end portion and is attachable and detachable to and from the distal end of the insertion portion through the opening end portion, a wedge-shaped first engagement portion which protrudes inward from an inner surface of a tubular portion of the cover, and a raising base which has a lever connection portion connected to the raising base connection portion and is provided rotatably inside the cover;

a third engagement portion provided in the insertion portion and engaged with the first engagement portion; and a cavity portion formed between the inner surface of the tubular portion of the cover and the insertion portion.

(Appendix 8)

A method of detaching an endoscope cap, including:

gripping an insertion portion of an endoscope having a rotatable raising base connection portion exposed on a surface of the insertion portion;

pressing the endoscope cap at two opposing places on an outside of the tubular portion of the cover, the endoscope cap including a bottomed tubular cover that has an opening end portion, is attachable and detachable to and from a distal end of the insertion portion of the endoscope through the opening end portion, and has a cavity portion against the distal end of the insertion portion of the endoscope when attached, a wedge-shaped first engagement portion that protrudes inward from an inner surface of a tubular portion of the cover, and a raising base that has a lever connection portion connected to the raising base connection portion and is provided rotatably inside the cover; and pulling the endoscope cap toward a distal end side along an insertion direction (Appendix 9)

An endoscope cap attachable and detachable to and from an endoscope including a lever rotatably provided at a distal end of an insertion portion of the endoscope and a rotating portion which rotates the lever, the endoscope cap including:

a bottomed tubular cover which has an opening end portion and is attachable and detachable to and from the distal end of the insertion portion of the endoscope through the opening end portion;

a first engagement portion which is provided on an inner surface of a tubular portion of the cover; and a raising base which has a lever connection portion connected to the lever and is provided rotatably inside the cover.

(Appendix 10)

The endoscope cap according to Appendix 9, in which the first engagement portion is a protrusion protruding inside the cover.

(Appendix 11)

The endoscope cap according to Appendix 10, in which
the cover has a window portion which is open to the tubular portion, and
the protrusion is provided closer to a side of the opening end portion than the window portion.

(Appendix 12)

The endoscope cap according to Appendix 11, in which the protrusion is provided on an edge of the window portion on the opening end portion side.

(Appendix 13)

The endoscope cap according to any one of Appendixes 10 to 12, in which
the insertion portion of the endoscope has a third engagement portion having a concave shape at a distal end, and
the first engagement portion is engaged with the third engagement portion.

(Appendix 14)

The endoscope cap according to any one of Appendixes 10 to 13, further including a second engagement portion opposing the first engagement portion.

(Appendix 15)

The endoscope cap according to Appendix 14, further including
a pedestal which is fixed to the inside of the cover and has a raising base attachment hole rotatably supporting the raising base,
in which the second engagement portion is a protrusion provided on the pedestal.

(Appendix 16)

The endoscope cap according to Appendix 15, in which the first engagement portion has a larger protruding amount than the second engagement portion.

(Appendix 17)

The endoscope cap according to any one of Appendixes 14 to 16, in which the first engagement portion is provided closer to the opening end portion side than the second engagement portion.

(Appendix 18)

The endoscope cap according to any one of Appendixes 15 to 17, in which
the insertion portion of the endoscope has a fourth engagement portion having a concave shape at a distal end, and
the second engagement portion is engaged with the fourth engagement portion.

(Appendix 19)

The endoscope cap according to any one of Appendixes 13 to 18, further including
a cavity portion formed between the inner surface of the tubular portion of the cover and the insertion portion when the insertion portion is inserted into the cover,
in which the first engagement portion is disengaged from the third engagement portion as the cover is pressed from an outside of the cavity portion.

(Appendix 20)

The endoscope cap according to Appendix 9, in which the first engagement portion is a concave portion provided in the inner surface of the cover.

(Appendix 21)

An endoscope including:
a rotatable raising base connection portion exposed on a surface of a distal end of an insertion portion;
an endoscope cap including a bottomed tubular cover which has an opening end portion and is attachable and detachable to and from the distal end of the insertion portion through the opening end portion, a first engagement portion which is provided on an inner surface of a tubular portion of the cover, and a raising base which has a lever connection portion connected to the raising base connection portion and is provided rotatably inside the cover;
a third engagement portion provided in the insertion portion and engaged with the first engagement portion; and
a cavity portion formed between the inner surface of the tubular portion of the cover and the insertion portion.

(Appendix 22)

The endoscope according to Appendix 21, in which
the first engagement portion is disengaged from the third engagement portion as the cover is pressed from an outside of the cavity portion.

(Appendix 23)

The endoscope according to Appendix 21 or 22, in which
the raising base connection portion protrudes from a hollow lever chamber which protrudes in an insertion direction from a part of the distal end of the insertion portion,
the lever chamber is covered with a plate-shaped lever chamber lid, and
the cavity portion is provided between the lever chamber lid and the cover.

(Appendix 24)

The endoscope according to Appendix 23, further including
a fixing member that fixes the lever chamber lid,
in which the fixing member has a head portion protruding to a surface of the lever chamber lid, and
the head portion is arranged in the cavity portion.

(Appendix 25)

The endoscope according to any one of Appendixes 21 to 24, in which the cavity portion is provided at two places opposing each other with the insertion direction therebetween.

(Appendix 26)

The endoscope according to any one of Appendixes 21 to 25, in which the raising base connection portion is thinner along the insertion direction on a side of the distal end than on an operation unit side.

(Appendix 27)

The endoscope according to any one of Appendixes 21 to 26, further including
a first indicator at the distal end of the insertion portion,
in which the endoscope cap has a second indicator corresponding to the first indicator.

(Appendix 28)

A method of detaching an endoscope cap, including:
gripping an insertion portion of an endoscope having a rotatable raising base connection portion exposed on a surface of the insertion portion;
pressing the endoscope cap at two opposing places on an outside of the tubular portion of the cover, the endoscope cap including a bottomed tubular cover that has an opening end portion, is attachable and detachable to and from a distal end of the insertion portion of the endoscope through the opening end portion, and has a cavity portion against the distal end of the insertion portion of the endoscope when attached, a first engagement portion that is provided on an inner surface of a tubular portion of the cover, and a raising base that has a lever connection portion connected to the raising base connection portion and is provided rotatably inside the cover; and pulling the endoscope cap toward a distal end side along an insertion direction.

What is claimed is:

1. A method of sterilizing an endoscope cap, comprising:
enclosing an endoscope cap in an individual packaging member, the endoscope cap including a bottomed tubular cover that is attachable and detachable to and from a distal end of an insertion portion of an endoscope including a lever which is rotatably provided at the distal end of the insertion portion of the endoscope and a rotating portion which rotates the lever, and a raising base that has a lever connection portion connected to the lever and is rotatably provided inside the bottomed tubular cover, the lever connection part is connected to the lever by attaching the bottomed tubular cover to the distal end of the insertion portion of the endoscope, and is disengaged from the lever by removing the bottomed tubular cover from the distal end of the insertion portion of the endoscope, and the raising base rotatably provided inside the bottomed tubular cover;

placing a plurality of the individual packaging members in a packaging box; and performing a sterilization process from an outside of the packaging box.

2. The method of sterilizing the endoscope cap according to claim 1, wherein the sterilization process is performed using a gas or radioactive ray.

\* \* \* \* \*